US010463664B2

(12) United States Patent
Tavis et al.

(10) Patent No.: US 10,463,664 B2
(45) Date of Patent: Nov. 5, 2019

(54) INHIBITORS OF HSV NUCLEOTIDYL TRANSFERASES AND USES THEREFOR

(71) Applicant: Saint Louis University, St. Louis, MO (US)

(72) Inventors: John Edwin Tavis, Kirkwood, MO (US); Lynda Anne Morrison, Webster Groves, MO (US); Marvin J. Meyers, Wentzville, MO (US)

(73) Assignee: Saint Louis University, St. Louis, MO (US)

( * ) Notice: Subject to any disclaimer, the term of this patent is extended or adjusted under 35 U.S.C. 154(b) by 0 days.

(21) Appl. No.: 15/038,515

(22) PCT Filed: Nov. 25, 2014

(86) PCT No.: PCT/US2014/067407
§ 371 (c)(1),
(2) Date: May 23, 2016

(87) PCT Pub. No.: WO2015/077774
PCT Pub. Date: May 28, 2015

(65) Prior Publication Data
US 2016/0296521 A1 Oct. 13, 2016

Related U.S. Application Data

(60) Provisional application No. 62/020,169, filed on Jul. 2, 2014, provisional application No. 61/908,251, filed on Nov. 25, 2013.

(51) Int. Cl.
| | | |
|---|---|---|
| *A61K 31/122* | (2006.01) | |
| *A61K 31/506* | (2006.01) | |
| *A61K 45/06* | (2006.01) | |
| *A61K 31/4418* | (2006.01) | |
| *A61K 31/352* | (2006.01) | |
| *A61K 31/4196* | (2006.01) | |
| *A61K 31/4245* | (2006.01) | |
| *A61K 31/4375* | (2006.01) | |
| *A61K 31/4433* | (2006.01) | |
| *A61K 31/4704* | (2006.01) | |
| *C07D 413/12* | (2006.01) | |
| *C07D 471/04* | (2006.01) | |
| *A61K 31/047* | (2006.01) | |
| *A61K 31/045* | (2006.01) | |

(52) U.S. Cl.
CPC .......... *A61K 31/506* (2013.01); *A61K 31/122* (2013.01); *A61K 31/352* (2013.01); *A61K 31/4196* (2013.01); *A61K 31/4245* (2013.01); *A61K 31/4375* (2013.01); *A61K 31/4418* (2013.01); *A61K 31/4433* (2013.01); *A61K 31/4704* (2013.01); *A61K 45/06* (2013.01); *C07D 413/12* (2013.01); *C07D 471/04* (2013.01)

(58) Field of Classification Search
CPC ... A61K 31/122; A61K 31/047; A61K 31/045
See application file for complete search history.

(56) References Cited

U.S. PATENT DOCUMENTS

2005/0037033 A1* 2/2005 Camus-Bablon .... A61K 9/0034
424/400

FOREIGN PATENT DOCUMENTS

| WO | WO 2006/095178 | 9/2006 |
|---|---|---|
| WO | WO 2007/065007 | 6/2007 |
| WO | WO 2012/106509 | 8/2012 |
| WO | WO 2012/154904 | 11/2012 |

OTHER PUBLICATIONS

Hogue et al. Retrovirology, 2009, vol. 6 No. 9, pp. 1-17.*
Partial Supplementary European Search Report issued in European Application No. 14864015.4, dated Jun. 19, 2017.
Reardon et al., "Herpes simplex virus type 1 DNA polymerase—Mechanism of inhibition by acyclovir triphosphate," *The Journal of Biological Chemistry*, 264(13):7405-7411, 1989.
Tavis et al., "Inhibitors of nucleotidyltransferase superfamily enzymes suppress herpes simplex virus replication," *Antimicrobial Agents and Chemotherapy*, 58(12):7451-7461 , 2014.
Aoki et al., "Antiviral effect of oryzacystatin, a proteinase inhibitor in rice, against herpes simplex virus type 1 in vitro and in vivo," *Antimicrob Agents Chemother.*, 39:846-849, 1995.
Billamboz et al., "Magnesium chelating 2-hydroxyisoquinoline-1,3(2H,4H)-diones, as inhibitors of HIV-1 integrase and/or the HIV-1 reverse transcriptase ribonuclease H domain: discovery of a novel selective inhibitor of the ribonuclease H function," J. Med. Chem., 54:1812-1824, 2011.
Chung et al., "Synthesis, activity, and structural analysis of novel α-hydroxytropolone inhibitors of human immunodeficiency virus reverse transcriptase-associated ribonuclease H," *J. Med. Chem.*, 54:4462-4473, 2011.
Fuji et al., "Derivatives of 5-nitro-furan-2-carboxylic acid carbamoylmethyl ester inhibit RNase H activity associated with HIV-1 reverse transcriptase," *J. Med. Chem.*, 52:1380-1387, 2009.
Hanauske-Abel et al., "Drug-induced reactivation of apoptosis abrogates HIV-1 infection," *PloS One*, 8:e74414, 2013.
Higaki et al., "Effect of oral valaciclovir on herpetic keratitis," *Cornea*, 25(10 Suppl 1):S64-67, 2006.
Himmel et al., "HIV-1 reverse transcriptase structure with RNase H inhibitor dihydrov benzoyl naphthyl hydrazone bound at a novel site," *ACS Chem. Biol.*, 1:702-712, 2006.
Himmel et al., "Structure of HIV-1 reverse transcriptase with the inhibitor beta-Thujaplicinol bound at the RNase H active site," *Structure*, 17:1625-1635, 2009.
Hu et al., "β-thujaplicinol inhibits hepatitis B virus replication by blocking the viral ribonuclease H activity," *Antiviral Research*, 99:221-229, 2013.

(Continued)

*Primary Examiner* — Samira J Jean-Louis
(74) *Attorney, Agent, or Firm* — Parker Highlander PLLC

(57) ABSTRACT

The present invention involves identification of inhibitors of herpesvirus nucleic acid metabolism. Also provided are methods of treatment using agents identified.

15 Claims, 27 Drawing Sheets

Specification includes a Sequence Listing.

(56) References Cited

OTHER PUBLICATIONS

Kirschberg et al., "RNase H active site inhibitors of human immunodeficiency virus type 1 reverse transcriptase: design, biochemical activity, and structural information," *J. Med. Chem.*, 52:5781-5784, 2009.

Klarmann et al., "Uncovering the complexities of retroviral ribonuclease H reveals its potential as a therapeutic target," *AIDS Rev*, 4:183-194, 2002.

PCT International Preliminary Report on Patentability issued in International Application No. PCT/US2014/067407, dated Jun. 9, 2016.

PCT International Search Report and Written Opinion issued in International Application No. PCT/US2014/067407, dated Mar. 27, 2015.

Semenova et al., "Preferential inhibition of the magnesium-dependent strand transfer reaction of HIV-1 integrase by alpha-hydroxytropolones,"*Mol. Pharmacol.*, 69:1454-1460, 2006.

Su et al., "Structural basis for the inhibition of RNase H activity of HIV-1 reverse transcriptase by RNase H active site-directed inhibitors," *J. Virol.*, 84:7625-7633, 2010.

Tavis et al., "The hepatitis B virus ribonuclease H is sensitive to inhibitors of the human immunodeficiency virus ribonuclease H and integrase enzymes," *PLoS Pathogens*, 9:e1003125, 2013.

Williams et al., "Potent and selective HIV-1 ribonuclease H inhibitors based on a 1-hydroxy-1,8-naphthyridin-2(1H)-one scaffold," *Bioorg. Med. Chem. Lett.*, 20:6754-6757, 2010.

* cited by examiner

Hydroxylated Tropolones
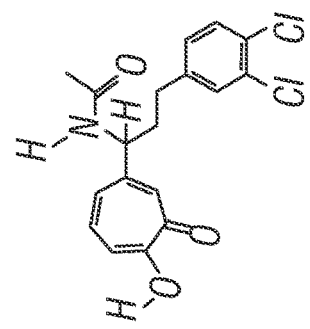
46. Beta Thujaplicinol
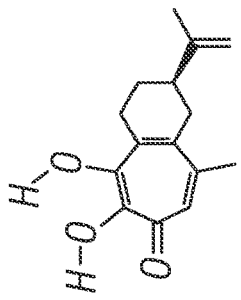
47. Beta Thujaplicin
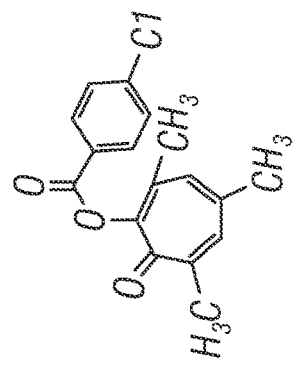
48. Gamma thujaplicin
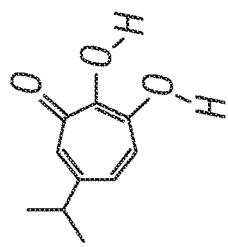
55. NSC 282885
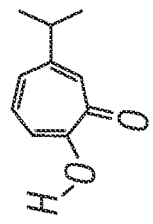
56. Manicol
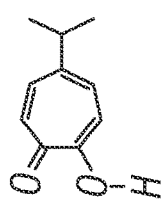
59. Chembridge 5945310
FIG. 1

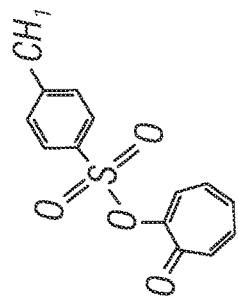
61. Chembridge 5940946
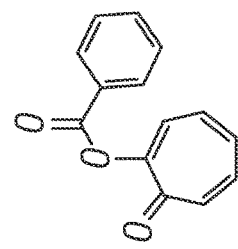
62. Chembridge 5946384
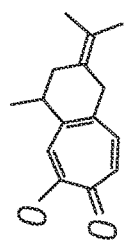
49. Nootkatin
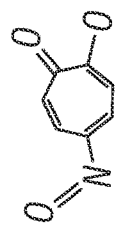
50. 5-nitrosotropolone
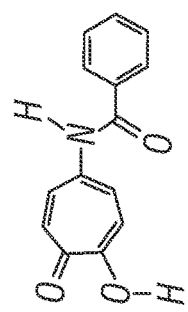
52. NSC 79555
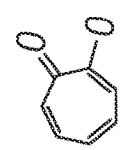
53. Tropolone
*FIG. 1 (Cont'd)*

*N-hydroxyisoquinolinediones*
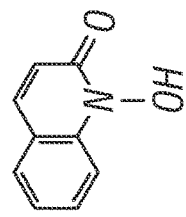
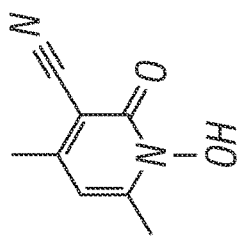
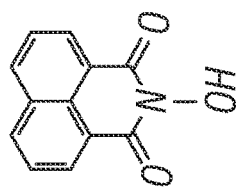
43. Sigma PH008969
44. Labotest 12243782
45. TCI America H1040
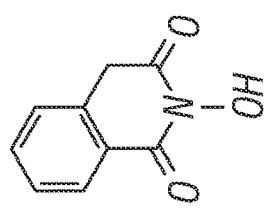
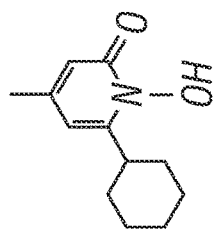
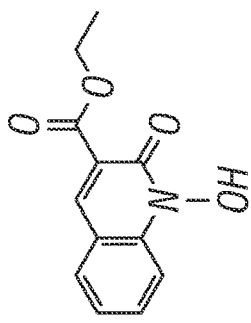
1. FCHC 2456
41. Ciclopirox
42. Labotest 7254325 1
*FIG. 1 (Cont'd)*

Hydroxyxanthenones
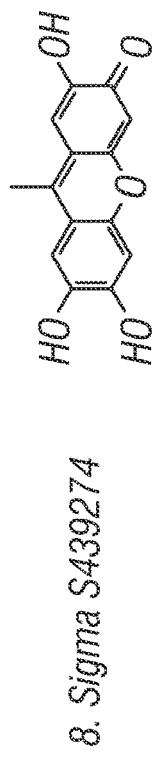
8. Sigma S439274
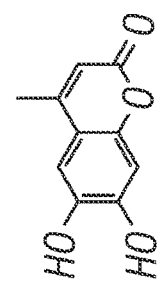
34. Idofine D-009
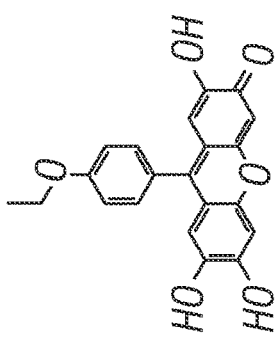
30. Chembridge 7248520
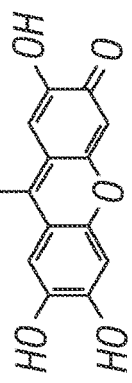
35. TCI America D1118
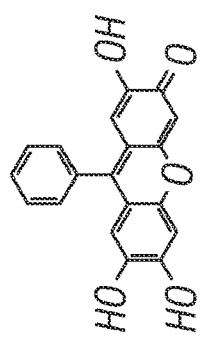
31. Chembridge 5104346
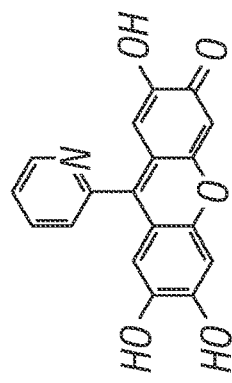
39. Asinex BAS0223612
FIG. 1 (Cont'd)

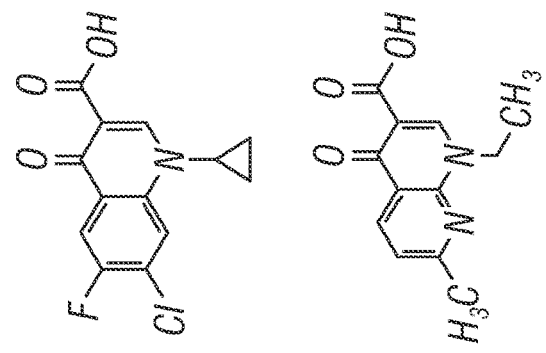
66. Sigma PHR1174
70. Sigma N8878
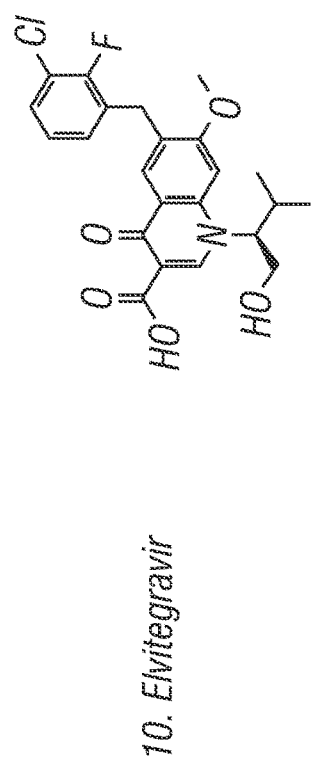
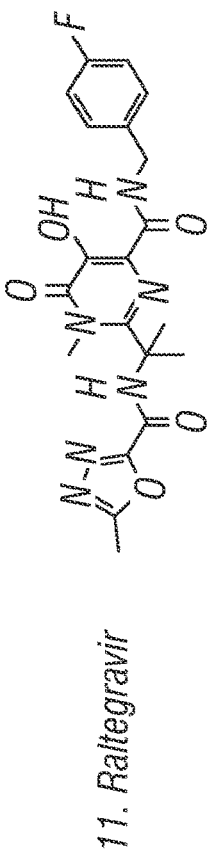
Elvitegravir, Raltegravir, and Derivatives
10. Elvitegravir
11. Raltegravir
FIG. 1 (Cont'd)

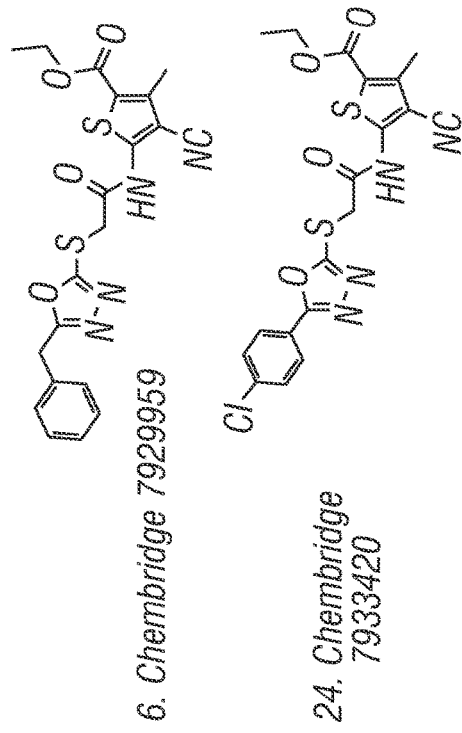
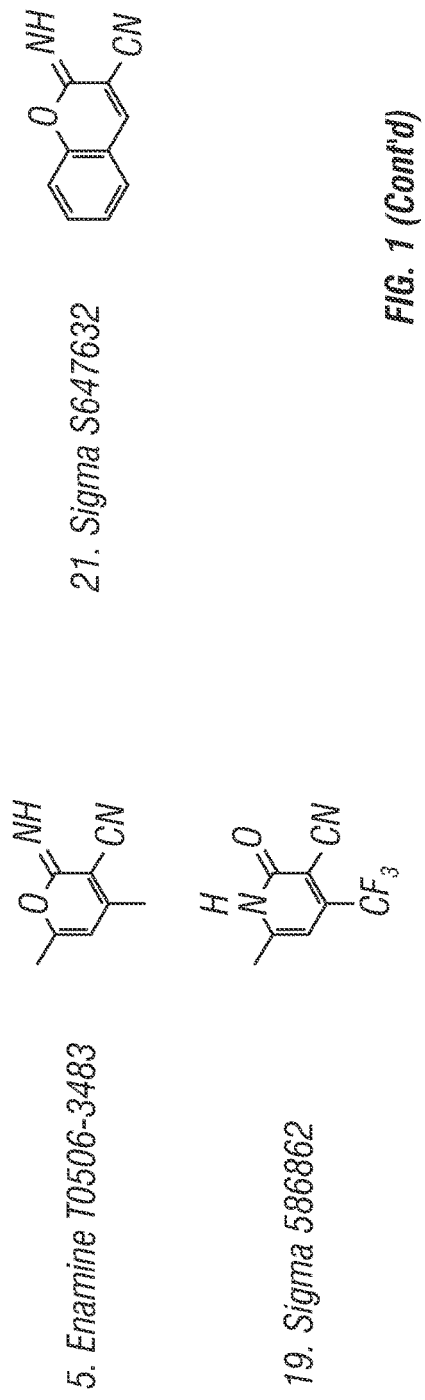
FIG. 1 (Cont'd)

Miscellaneous Compounds
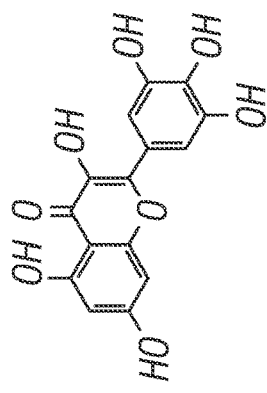
9. Sigma 70050
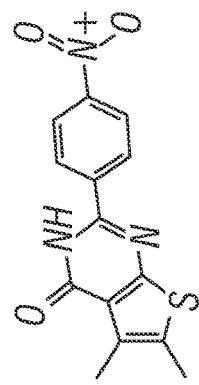
22. CAS 40106-12-5
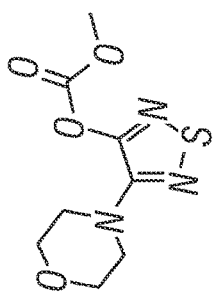
38. Visas M Lab STK317995
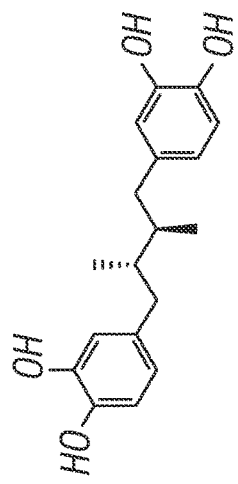
2. Sigma 74540
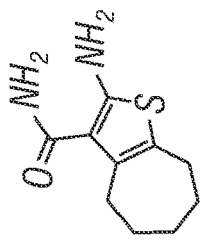
3. Sigma n8164
4. TimTec ST029023
FIG. 1 (Cont'd)

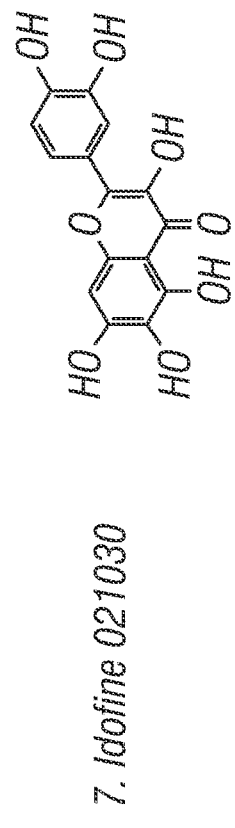
7. Idofine 021030
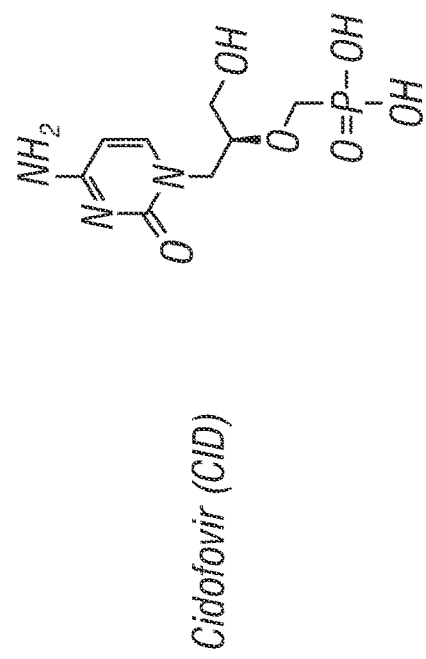
Cidofovir (CID)
Nucleos(t)ide analogs
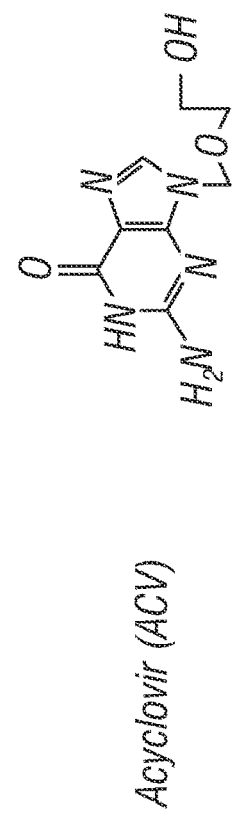
Acyclovir (ACV)
FIG. 1 (Cont'd)

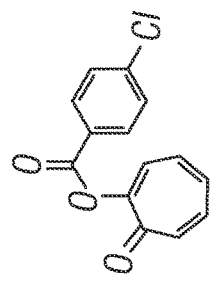
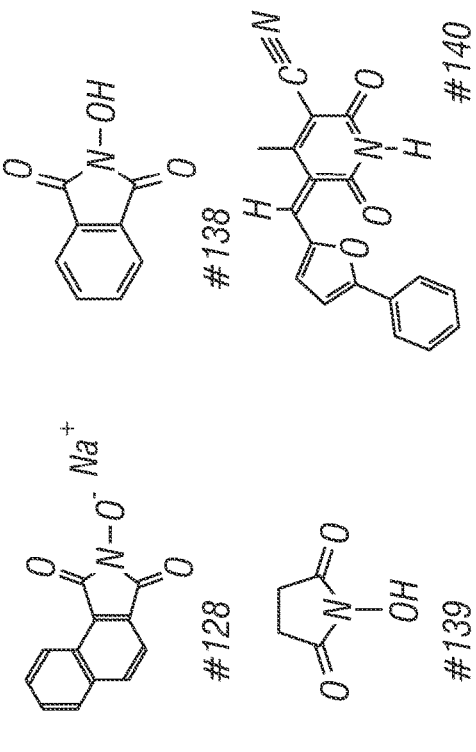
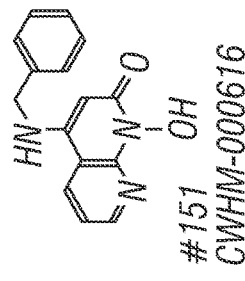
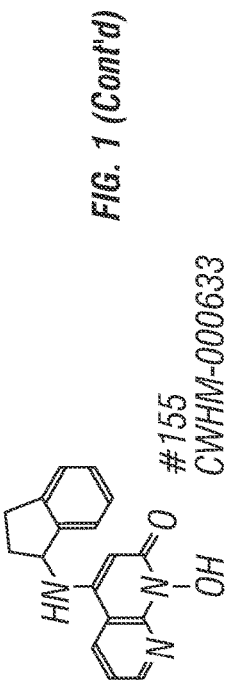
FIG. 1 (Cont'd)

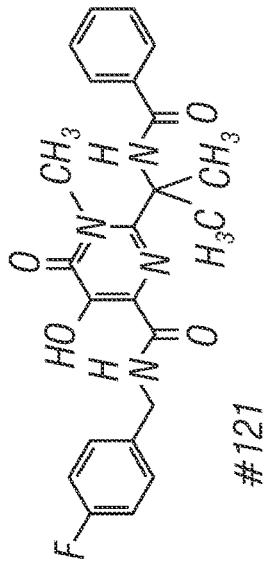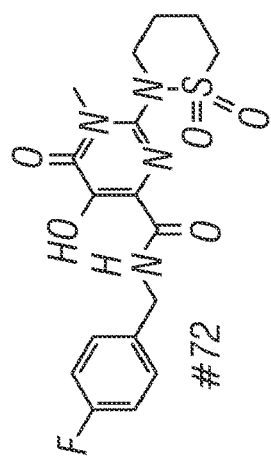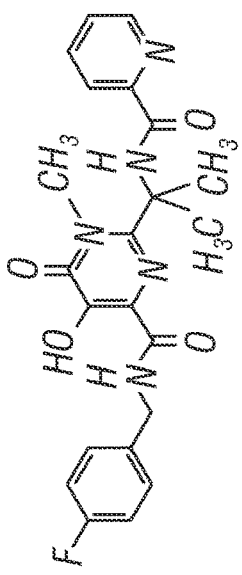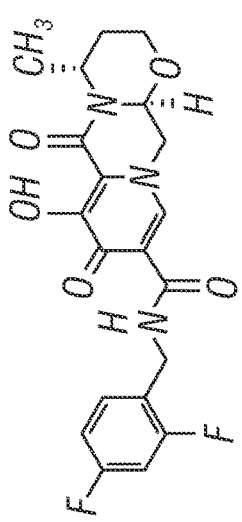
FIG. 1 (Cont'd)

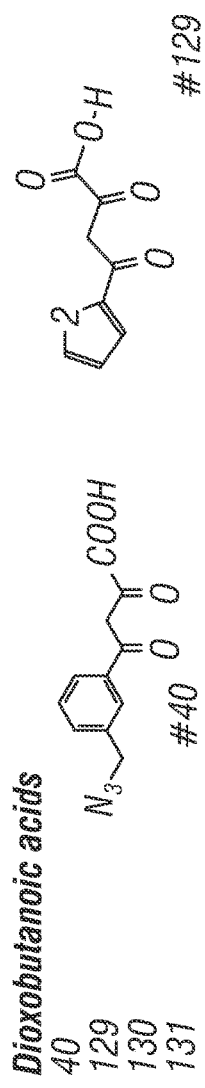
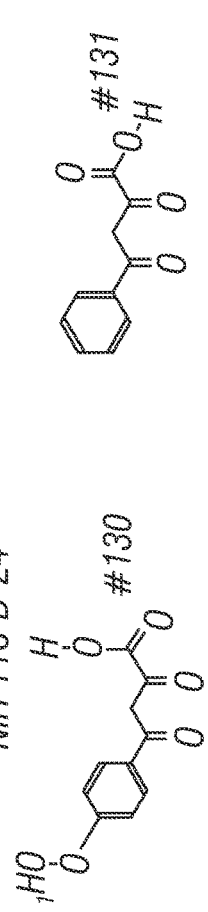
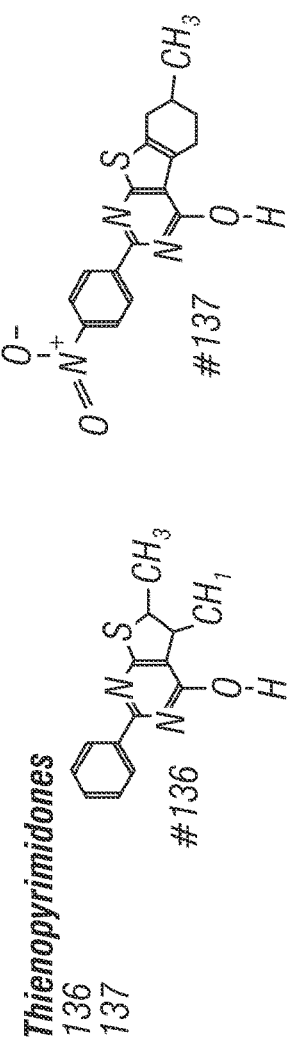
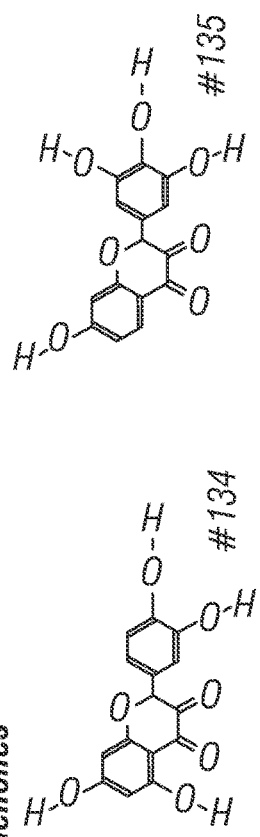
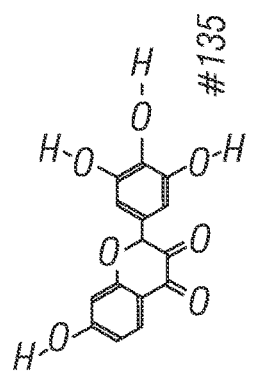
FIG. 1 (Cont'd)

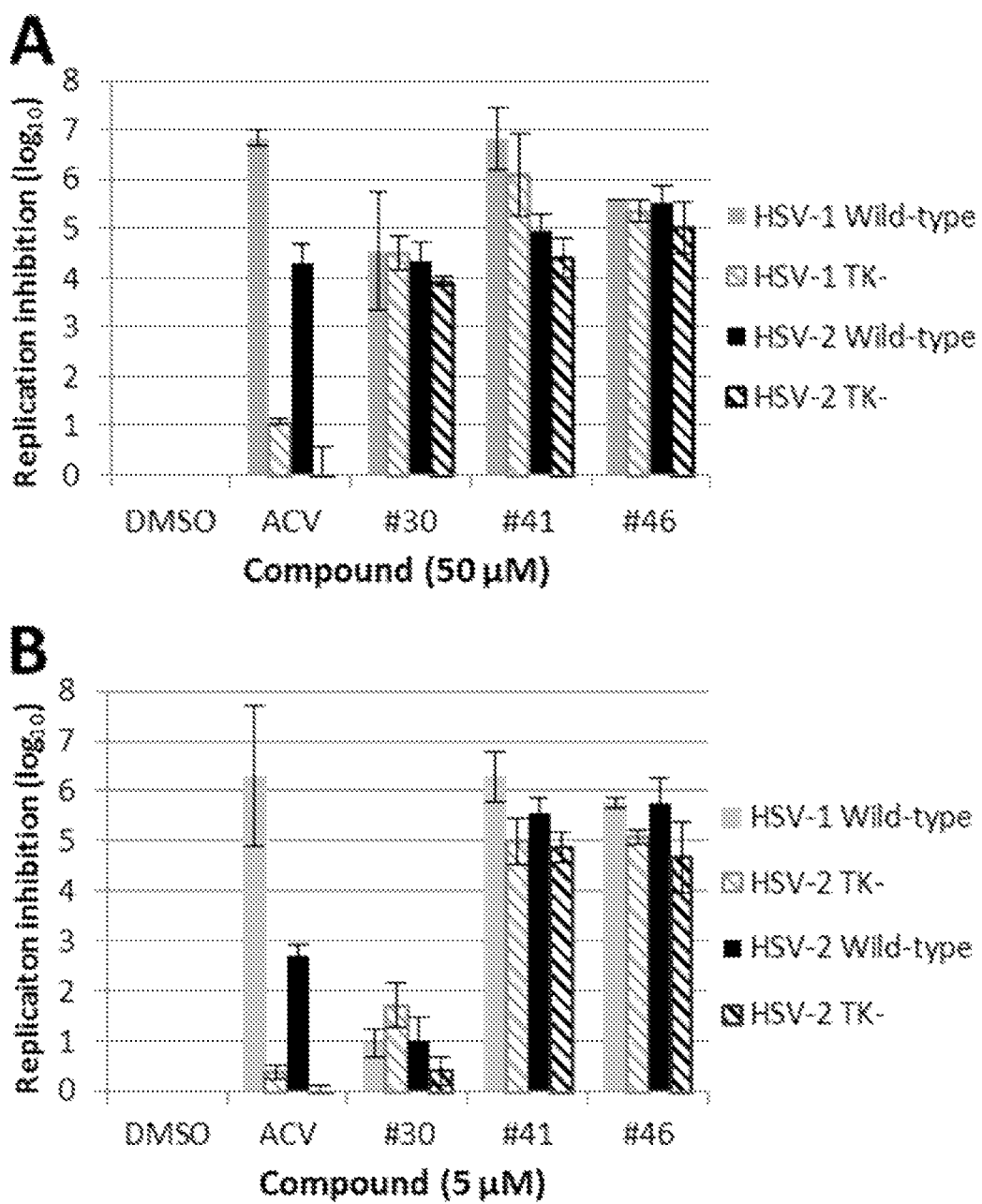
FIGS. 8A-B

INHIBITORS OF HSV NUCLEOTIDYL TRANSFERASES AND USES THEREFOR

This application is a national phase application under 35 U.S.C. § 371 of International Application No. PCT/US2014/067407, filed Nov. 25, 2014, which claims the benefit of U.S. Provisional Application 61/908,251, filed Nov. 25, 2013, and U.S. Provisional Application 62/020,169, filed Jul. 2, 2014, the entirety of each of which is incorporated herein by reference.

BACKGROUND OF THE INVENTION

I. Field of the Invention

The invention relates to the fields of pathology, virology, molecular biology and pharmaceuticals. More specifically, the invention relates to the identification of candidate inhibitors for the treatment and prevention of herpesvirus diseases. Also provided are compounds having such activity.

II. Related Art

Herpesviridae is a large family of DNA viruses that cause diseases in vertebrates, including humans. These viruses are significant pathogens and, in addition to primary infections, cause latent, recurring infections. At least six species of Herpesviridae—herpes simplex virus 1 (HSV-1) and HSV-2 (both of which can cause orolabial herpes and genital herpes), Varicella-zoster virus (which causes chickenpox and shingles), Epstein-Barr virus (which causes mononucleosis), Cytomegalovirus (which causes mental retardation and deafness in neonates), and Human herpesvirus 6 (which causes roseola infantum and febrile seizures)—are extremely widespread among humans. More than 90% of adults have been infected with at least one of these, and a latent form of the virus remains in most people. Other viruses with human tropism include human herpesvirus 7 and Kaposi's sarcoma-associated herpesvirus. There are more than 130 herpesviruses, including those that infect non-human mammals, birds, fish, reptiles, amphibians, and molluscs.

The drugs, acyclovir and ganciclovir, are considered the standard treatments and prophylactic agents for infections caused by HSV, VZV and CMV. Until a decade ago, the impact of acyclovir on the control of severe and life-threatening herpesvirus infections was unprecedented. Recently, approval of new drugs (i.e., penciclovir and the oral prodrugs, valaciclovir, famciclovir, cidofovir, fomivirsen, and foscarnet) has increased the number of therapeutic options for medical practitioners. Newer agents, such as brivudin and benzimidavir, are in ongoing clinical development, while others have been suspended because of safety concerns. Regardless, new anti-herpes agents are needed to face clinical issues such as drug resistance, increased use of anti-herpes prophylaxis, and safety concerns in small children or pregnant women.

SUMMARY OF THE INVENTION

Thus, in accordance with the present disclosure, there is provided a method of inhibiting a cellular or herpesvirus nucleic acid metabolism enzyme comprising contacting said enzyme with a compound having the formula:

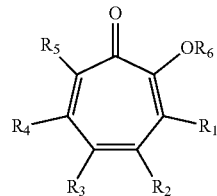

wherein: $R_1$ is hydrogen, hydroxyl, alkyl$_{(C\leq6)}$, or substituted alkyl$_{(C\leq6)}$; $R_2$ is hydrogen, alkyl$_{(C\leq6)}$, substituted alkyl$_{(C\leq6)}$, or when taken together with $R_3$ is alkanediyl$_{(C\leq12)}$, alkenediyl$_{(C\leq12)}$, or a substituted version of either of these groups; $R_3$ is hydrogen, nitro, alkyl$_{(C\leq8)}$, alkenyl$_{(C\leq8)}$, alkynyl$_{(C\leq8)}$, acyloxy$_{(C\leq12)}$, amido$_{(C\leq12)}$, or a substituted version of any of the last five groups, or when taken together with $R_2$ is alkanediyl$_{(C\leq12)}$, alkenediyl$_{(C\leq12)}$, or a substituted version of either of these groups; $R_2$ and $R_3$ when taken together have a formula:

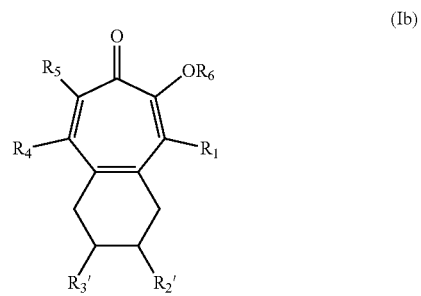

wherein: $R_2'$ and $R_3'$ are each independently hydrogen, alkyl$_{(C\leq4)}$, substituted alkyl$_{(C\leq4)}$, alkenyl$_{(C\leq4)}$, or substituted alkenyl$_{(C\leq4)}$; $R_4$ is hydrogen, alkyl$_{(C\leq8)}$, alkenyl$_{(C\leq8)}$, alkynyl$_{(C\leq8)}$, aryl$_{(C\leq8)}$, aralkyl$_{(C\leq12)}$, or a substituted version of any of the last five groups; $R_5$ is hydrogen, alkyl$_{(C\leq6)}$, or a substituted alkyl$_{(C\leq6)}$; and $R_6$ is hydrogen, acyl$_{(C\leq12)}$, or substituted acyl$_{(C\leq12)}$;

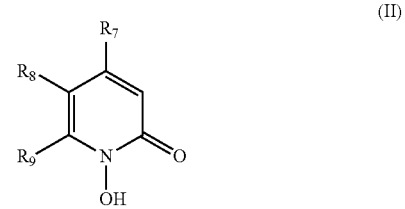

wherein: $R_7$ is hydrogen, alkyl$_{(C\leq6)}$, or a substituted alkyl$_{(C\leq6)}$; $R_8$ is hydrogen or when taken together with $R_9$ is as defined below in Formula IIb; $R_9$ is hydrogen, alkyl$_{(C\leq8)}$, substituted alkyl$_{(C\leq8)}$, or when taken together with $R_8$ is as defined below in Formula IIb; $R_8$ and $R_9$ when taken together have a formula:

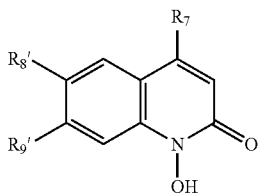
(IIb)

wherein: $R_8'$ and $R_9'$ are each independently hydrogen, halo, alkyl$_{(C\leq 6)}$ or substituted alkyl$_{(C\leq 6)}$;

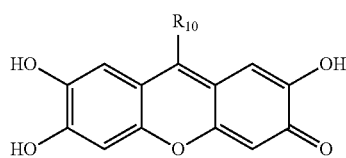
(III)

wherein: $R_{10}$ is alkyl$_{(C\leq 6)}$, substituted alkyl$_{(C\leq 6)}$,

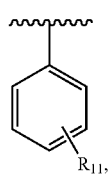

heteroaryl$_{(C\leq 8)}$, or substituted heteroaryl$_{(C\leq 8)}$; $R_{11}$ is hydrogen, hydroxy, halo, amino, nitro, cyano, alkyl$_{(C\leq 6)}$, alkoxy$_{(C\leq 6)}$, alkylamino$_{(C\leq 6)}$, dialkylamino$_{(C\leq 6)}$, or a substituted version of any of the last four groups; or

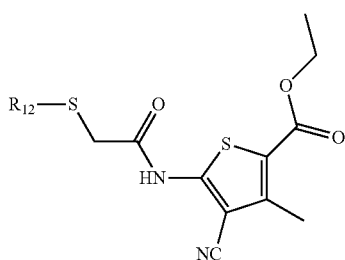
(IV)

wherein: $R_{12}$ is heteroaryl$_{(C\leq 12)}$ or substituted heteroaryl$_{(C\leq 12)}$;

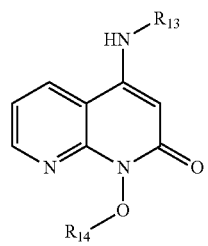
(V)

wherein: $R_{13}$ is aryl$_{(C\leq 12)}$, aralkyl$_{(C\leq 12)}$, or a substituted version of either of these groups; and $R_{14}$ is hydrogen, alkyl$_{(C\leq 6)}$, or substituted alkyl$_{(C\leq 6)}$; or a pharmaceutically acceptable salt thereof. In some embodiments, the compound is further defined as:

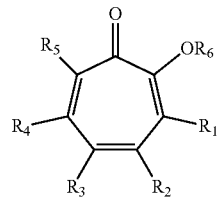
(I)

wherein: $R_1$ is hydrogen, hydroxyl, alkyl$_{(C\leq 6)}$, or substituted alkyl$_{(C\leq 6)}$; $R_2$ is hydrogen, alkyl$_{(C\leq 6)}$, substituted alkyl$_{(C\leq 6)}$, or when taken together with $R_3$ is alkanediyl$_{(C\leq 12)}$, alkenediyl$_{(C\leq 12)}$, or a substituted version of either of these groups; $R_3$ is hydrogen, alkyl$_{(C\leq 8)}$, alkenyl$_{(C\leq 8)}$, alkynyl$_{(C\leq 8)}$, acyloxy$_{(C\leq 12)}$, amido$_{(C\leq 12)}$, or a substituted version of any of the last five groups, or when taken together with $R_2$ is alkanediyl$_{(C\leq 12)}$, alkenediyl$_{(C\leq 12)}$, or a substituted version of either of these groups; $R_2$ and $R_3$ when taken together have a formula:

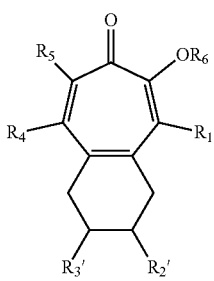
(Ib)

wherein: $R_2'$ and $R_3'$ are each independently hydrogen, alkyl$_{(C\leq 4)}$, substituted alkyl$_{(C\leq 4)}$, alkenyl$_{(C\leq 4)}$, or substituted alkenyl$_{(C\leq 4)}$; $R_4$ is hydrogen, alkyl$_{(C\leq 8)}$, alkenyl$_{(C\leq 8)}$, alkynyl$_{(C\leq 8)}$, aryl$_{(C\leq 8)}$, aralkyl$_{(C\leq 12)}$, or a substituted version of any of the last five groups; $R_5$ is hydrogen, alkyl$_{(C\leq 6)}$, or a substituted alkyl$_{(C\leq 6)}$; and $R_6$ is hydrogen, acyl$_{(C\leq 12)}$, or substituted acyl$_{(C\leq 12)}$; The compound may be further defined by the formula:

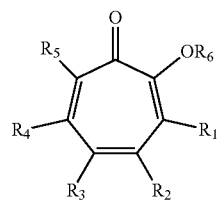
(I)

wherein: $R_1$ is hydrogen, hydroxyl, or alkyl$_{(C\leq 6)}$; $R_2$ is hydrogen, alkyl$_{(C\leq 6)}$, or when taken together with $R_3$ is as defined below in Formula Ib; $R_3$ is hydrogen, alkyl$_{(C\leq 8)}$, alkenyl$_{(C\leq 8)}$, amido$_{(C\leq 12)}$, or when taken together with $R_2$ is as defined below in Formula Ib; $R_2$ and $R_3$ when taken together have a formula:

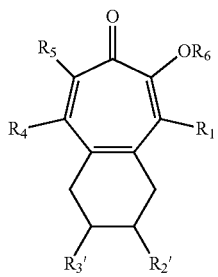

(Ib)

wherein: $R_2'$ and $R_3'$ are each independently hydrogen or alkenyl$_{(C \leq 4)}$; $R_4$ is hydrogen, alkyl$_{(C \leq 8)}$, aralkyl$_{(C \leq 12)}$, or substituted aralkyl$_{(C \leq 12)}$; $R_5$ is hydrogen or alkyl$_{(C \leq 6)}$; $R_6$ is hydrogen or substituted acyl$_{(C \leq 12)}$;

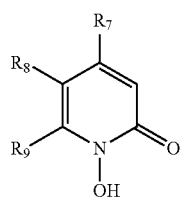

(II)

wherein: $R_7$ is hydrogen or alkyl$_{(C \leq 6)}$; $R_8$ is hydrogen or when taken together with $R_9$ is as defined below in Formula IIb; $R_9$ is hydrogen, alkyl$_{(C \leq 8)}$, or when taken together with $R_8$ is as defined below in Formula IIb; $R_8$ and $R_9$ when taken together have a formula:

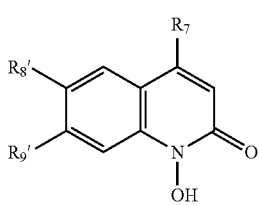

(IIb)

wherein: $R_8'$ and $R_9'$ are each independently hydrogen or halo;

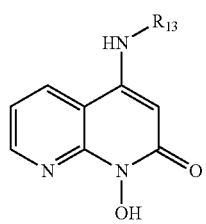

(Vb)

wherein: $R_{13}$ is aryl$_{(C \leq 12)}$, aralkyl$_{(C \leq 12)}$, or a substituted version of either of these groups; or a pharmaceutically acceptable salt thereof In particular embodiments, $R_1$ may be hydrogen or hydroxyl, $R_2$ and $R_3$ may be taken together and have formula Ib, $R_3'$ may be alkenyl$_{(C \leq 4)}$, $R_4$ may be hydrogen, alkyl$_{(C \leq 4)}$, or substituted aralkyl$_{(C \leq 12)}$, $R_6$ may be hydrogen, $R_7$ may be hydrogen or methyl, $R_8$ and $R_9$ are taken together and have formula IIb, and/or $R_{13}$ is benzyl or 1-indanyl. In some embodiments, the pharmaceutically acceptable salt is an ethanolamine salt. The compound may be further defined as:

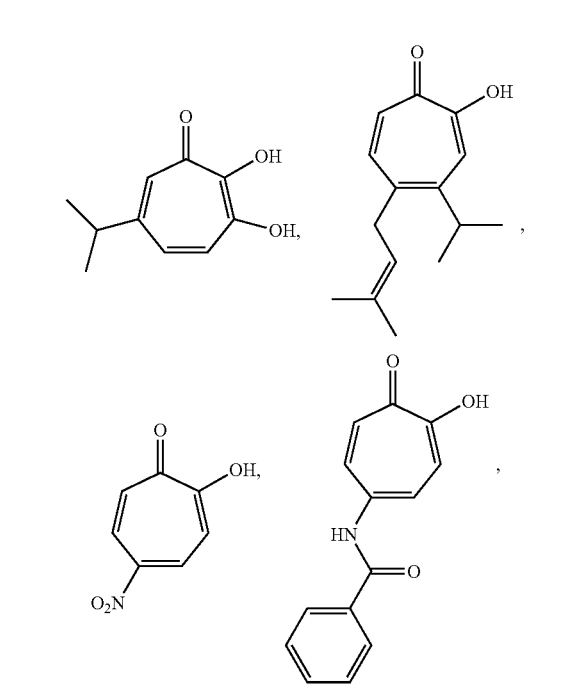

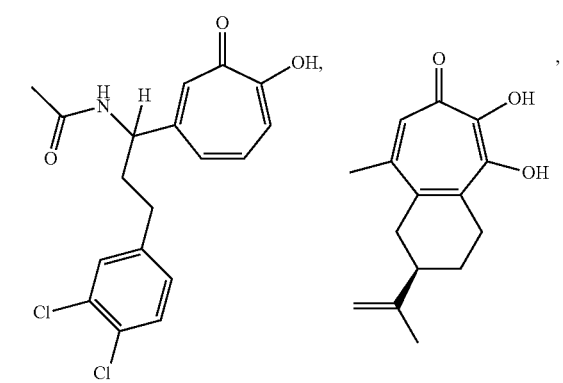

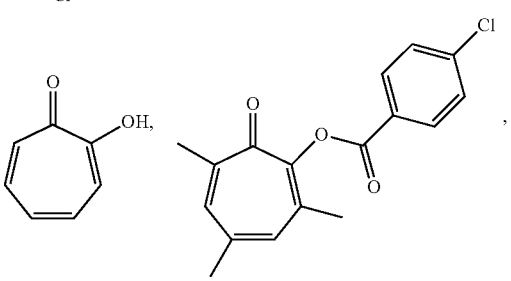

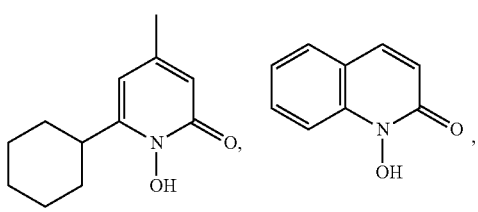

-continued

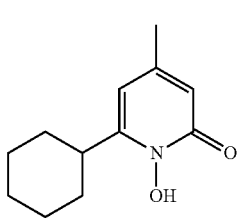

, and

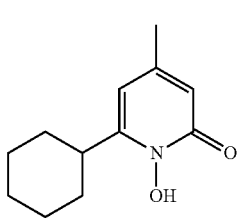

;

or a pharmaceutically acceptable salt thereof. In some embodiments, the compound is:

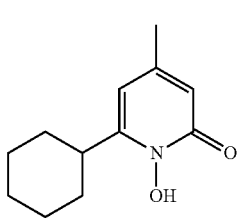

or an ethanolamine salt thereof

The method further may further comprise contacting said enzyme with a second inhibitor of said enzyme, or further comprise contacting said enzyme with said compound a second time. The enzyme may be located in a cell, which cell may be located in vitro or located in a living subject. The subject may be a vertebrate infected with a herpesvirus. The compound may be administered intravenously, intra-arterially, orally, buccally, nasally, rectally, vaginally, topically, intramuscularly, intradermally, cutaneously or subcutaneously. The subject may be further administered a second anti-herpesvirus therapy distinct from the compound. The second anti-herpesvirus therapy may be foscarnet or a nucleoside analog, such as acyclovir, famciclovir, valaciclovir, penciclovir, or ganciclovir. The second anti-herpesvirus therapy may be administered to said subject before or after said compound. The second anti-herpesvirus therapy may be administered to said subject at the same time as said compound.

The subject may have previously received a first-line anti-herpesvirus therapy, and further may have developed resistance to said first-line anti-herpesvirus therapy. The herpevirus may be selected from a human alpha herpesvirus, a human beta herpesvirus or a human gamma herpesvirus. The human alpha herpesvirus may be selected from herpes simplex virus 1 (HSV-1), herpes simplex virus 2 (HSV-2), and Varicella-Zoster virus (VZV). The human beta herpesvirus may be selected from human cytomegalovirus (HCMV), human herpesvirus 6 (HHV-6), and human herpesvirus 7 (HHV-7). The human gamma herpesvirus may be selected from Epstein-Barr virus (EBV) and Kaposi's sarcoma herpesvirus (KSHV). The herpesvirus may be a non-human herpesvirus, such as Marek's disease virus, equine herpesviruses, Bovine herpeviruses, or pseudorabies virus.

In another aspect, the present disclosure provides a compound of the formula:

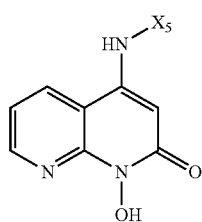

(VI)

wherein: $X_1$ is aryl$_{(C \leq 12)}$, aralkyl$_{(C \leq 12)}$, heteroaryl$_{(C \leq 12)}$, or a substituted version of any of these groups; and $X_2$, $X_3$, and $X_4$ are each independently selected from hydrogen, alkyl$_{(C \leq 8)}$, or substituted alkyl$_{(C \leq 8)}$;

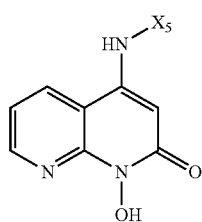

(VII)

wherein: $X_5$ is aryl$_{(C \leq 12)}$, aralkyl$_{(C \leq 12)}$, or a substituted version of either of these groups; or a pharmaceutically acceptable salt thereof. In some embodiments, $X_3$ and $X_4$ are methyl. In some embodiments, $X_1$ is aryl$_{(C \leq 12)}$, heteroaryl$_{(C \leq 12)}$, or a substituted version of either of these groups. In some embodiments, $X_5$ is aralkyl$_{(C \leq 12)}$ or substituted aralkyl$_{(C \leq 12)}$. In some embodiments, the compound is further defined as:

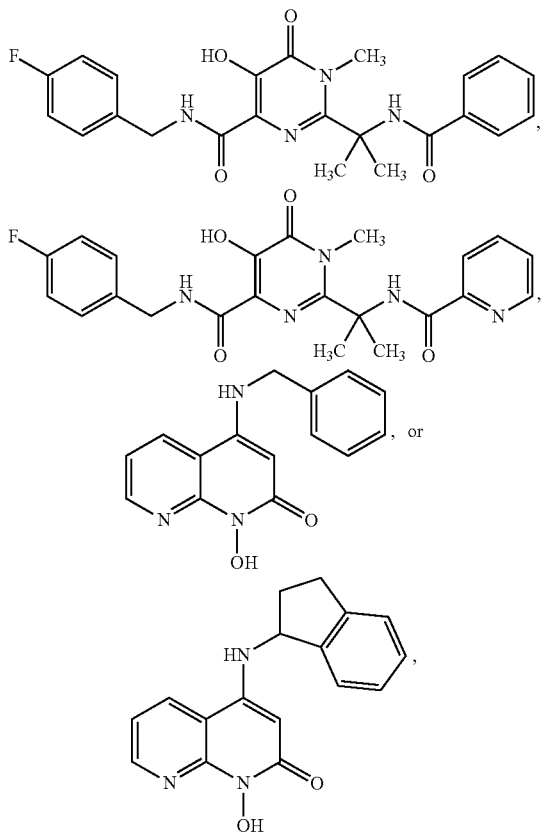

or a pharmaceutically acceptable salt thereof

In yet another aspect, the present disclosure provides a pharmaceutical composition comprising a compound of the present disclosure and an excipient. In some embodiments, the pharmaceutical composition is formulated for administration: orally, nasally, buccally, corneally, rectally, vaginally, or topically. In other embodiments, the pharmaceutical composition formulated for administration via injection. In some embodiments, the injection is formulated for administration: intradermally, cutaneously, subcutaneously, intramuscularly, intraperitoneally, intraarterially, or intravenously.

Other objects, features and advantages of the present invention will become apparent from the following detailed description. It should be understood, however, that the detailed description and the specific examples, while indicating preferred embodiments of the invention, are given by way of illustration only, since various changes and modifications within the spirit and scope of the invention will become apparent to those skilled in the art from this detailed description.

BRIEF DESCRIPTION OF THE DRAWINGS

The following drawings form part of the present specification and are included to further demonstrate certain aspects of the present invention. The invention may be better understood by reference to one or more of these drawings in combination with the detailed description of specific embodiments presented herein.

FIG. 1. Chemical structures of the compounds used in the studies. Compound numbers, names and chemical classes correspond to Table 2.

FIGS. 8A-B. Sensitivity of thymidine kinase-deficient HSVs to NTS inhibitors. Vero cell monolayers were infected with the indicated wild-type or mutant HSV-1 or HSV-2 strains at moi of 0.1 in the presence of ACV or nucleotidyl transferase superfamily (NTS) inhibitors #30, 41 or 46 at (FIG. 8A) 50 µM or (FIG. 8B) 5 µM. Cultures were collected 24 hours post-infection and infectious virus titers were determined by plaque assay. Values are the averages±one standard deviation from two experiments, each done in duplicate.

(FIG. 9A) KOS or ACV-selected lineages treated with ACV; (FIG. 9B) KOS or #41-selected lineages treated with #41; and (FIG. 9C) KOS or #46-selected lineages treated with #46. Data are expressed as fold ($\log_{10}$) inhibition of replication in the presence of compound compared with diluent control.

(FIG. 11B) trigeminal ganglia (TG) and (FIG. 11C) brainstem 5 days post-infection was assessed by plaque assay. N=two mice per group. **, P=0.0022-0.0062; *, P=0.0291 for DMSO v. #46.

DETAILED DESCRIPTION

Figure 2:
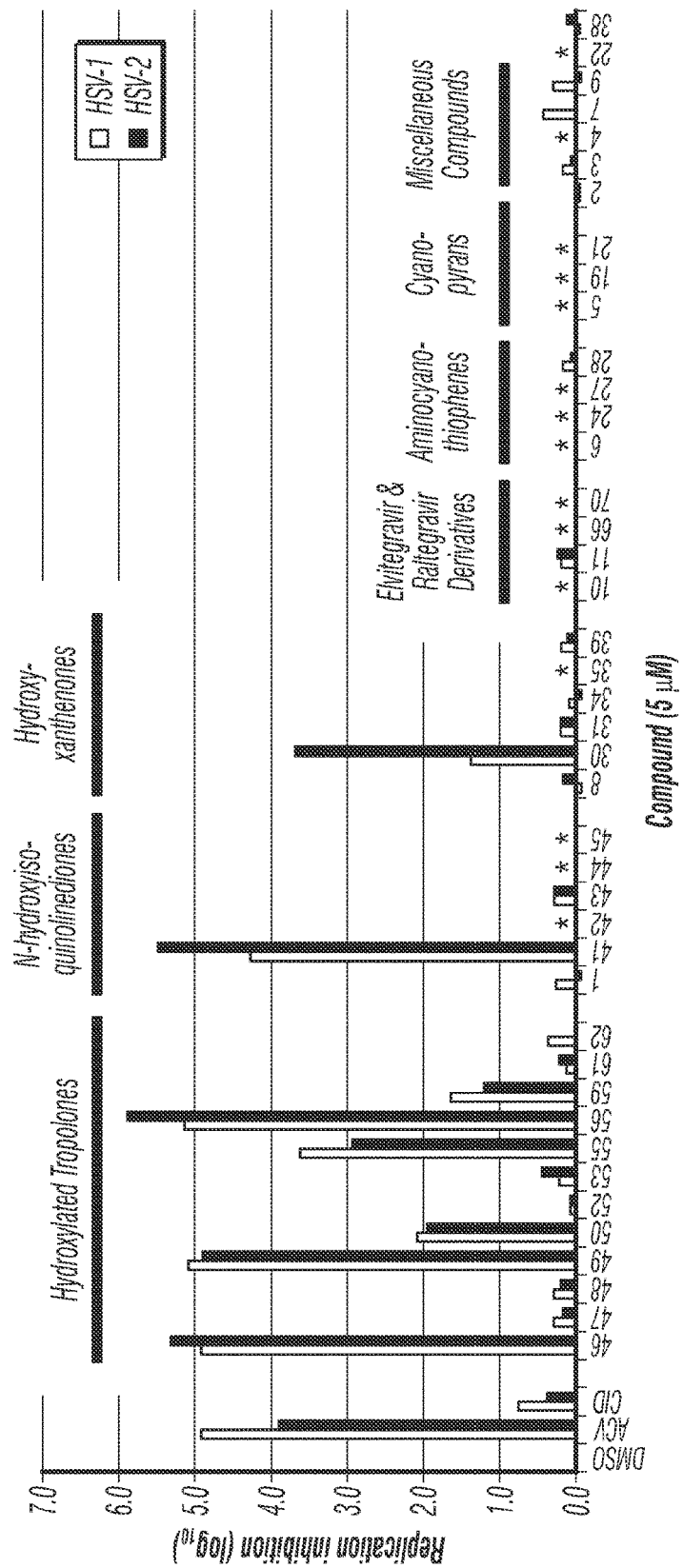
FIG. 2. Suppression of HSV-1 and HSV-2 replication by compounds at 5 µM. Compounds were added to Vero cells simultaneously with HSV-1 or HSV-2 infection at multiplicity of infection (moi) of 0.1. Twenty-four hours later the cultures were harvested and infectious virus titers in the cultures were determined by plaque assay. Replication inhibition is expressed as the difference in recovered titers in the compound-treated cultures compared to values obtained for the DMSO vehicle-treated control from the same experiment. Data are the averages from two to four experiments per compound, each done in duplicate. ACV, acyclovir; CID, cidofovir. Asterisks indicate that the titer was not determined because CPE was visually equivalent to DMSO control.

The inventors have demonstrated that inhibitors of nucleotidyl-transferase superfamily enzymes from multiple different chemical classes profoundly suppress replication of HSV-1 and HSV-2 with no measurable toxicity in short-term cell culture assays. Inhibition by these primary screening hits is equal or superior to the approved anti-herpesvirus drug acyclovir. Indeed, the existing compounds may already be superior to the drugs that are used for herpesvirus infection, and improved efficacy can readily be envisioned through standard medicinal chemistry approaches. Inhibitors of NTS enzymes may well have a high barrier to development of antiviral resistance, and their unique mode (s) of action suggest that they would be good candidates for combination therapy with the existing anti-herpesvirus drugs to improve efficacy of antiviral therapy. These and other aspects of the disclosure are discussed in detail below.

A. Herpesvirus

Herpesviruses are a diverse group of enveloped viruses having a large, double-stranded DNA genome enclosed in an icosahedral capsid (Pellet & Roizman 2013). The herpesviruses rely on the host cell RNA polymerase II for transcription, but encode all of the enzymes needed for replication of their genomes, including DNA polymerase, helicase, primase, terminase, ribonucleotide reductase, and thymidine kinase. All herpesviruses share the capacity to establish latency in host cells, allowing them to maintain the infection for the life of the host. Periodic reactivation from latency in response to cues in the cellular environment leads to lytic replication at mucosal surfaces, causing recurrent disease and providing the opportunity for transmission to uninfected individuals.

The herpesviruses are divided into three subclasses based primarily on their cellular tropism and characteristics of the latent infection. The human alpha herpesviruses herpes simplex virus 1 (HSV-1) (Roizman et al., 2013), herpes simplex virus 2 (HSV-2) (Roizman et al., 2013) and Varicella-Zoster virus (VZV) (Arvin & Gilden 2013) establish latency in sensory neurons where they may remain quiescent for long periods of time. HSV-1 and HSV-2 are similar viruses with colinear genomes and 83% nucleotide sequence identity in protein coding regions (Dolan et al., 1998); VZV contains a smaller, less homologous genome. The human beta herpesviruses human cytomegalovirus (HCMV), human herpesvirus 6 (HHV-6) and human herpesvirus 7 (HHV-7) (Yamanishi et al., 2013) establish latency predominantly in mononuclear cells. The human gamma herpesviruses Epstein-Barr virus (EBV) (Longnecker et al., 2013) and Kaposi's sarcoma herpesvirus (KSHV) (Damania & Cesarman 2013) stimulate cellular proliferation upon infection. EBV infects B lymphocytes, where it establishes latency, and also epithelial cells. By contrast, endothelial cells harbor the latent reservoir of KSHV, although the virus infects numerous other cell types as well. The genomes of latent beta and gamma herpesviruses are replicated as the host cell divides in order to maintain latent infection.

Herpesviruses related the human herpesviruses infect numerous animal species, including several of significant economic importance. Key among these are pseudorabies virus which infects pigs, Marek's disease virus which infects chickens, bovine herpesvirus, equine herpesvirus, and salmonid and related herpesviruses that infect game fish.

1. Pathology

Primary infections with herpesviruses produce a broad spectrum of disease. HSV-1 causes numerous maladies (Roizman et al., 2013): gingivostomatitis; eczema herpeticum; herpes gladiatorum; less common but frequently fatal encephalitis; and an increasing proportion of ulcerative anogential lesions (Gilbert et al., 2011; Horowitz et al., 2011; Pena et al., 2010; Smith & Roberts 2009). Nearly two-thirds of the U.S. population has been exposed to HSV-1 (Xu et al., 2006). HSV-2 infects approximately 17% of Americans (Xu et al., 2006) and up to 75% of some demographics world-wide (Obasi et al., 1999 and Kamali et al., 1999), with an estimated global disease burden of more than half a billion people (Ser. No. 18/949,218). HSV-2 is the primary cause of ulcerative anogenital lesions. In addition, HSV-1 and HSV-2 may be transmitted from a pregnant woman to her child during birth, often causing potentially fatal disseminated disease in the newborn (Kimberlin 2007). HCMV is the most common in utero virus infection (Manicklal et al., 2013), and approximately 8,000 HCMV-infected infants born each year in the U.S. suffer sensorineural deafness, chorioretinitis, and/or mental retardation (James et al., 2009). In immunocompromised individuals, HCMV can cause mononucleosis, retinitis, colitis, pneumonitis, and esophagitis. These serious HCMV infections are associated with increased morbidity and mortality (Komatsu et al., 2014). EBV causes the vast majority of infectious mononucleosis, which strikes nearly half of young adults (Luzuriaga & Sullivan 2010). Notably, of the eight human herpesviruses, a vaccine is available only for VZV.

The novel capacity of herpesviruses to establish and reactivate from latency is also associated with numerous pathologies. HSV-1 causes recurrent cold sores; a significant proportion of devastating viral encephalitis; and corneal scarring known as herpetic stromal keratitis which is the most frequent infectious cause of blindness, afflicting nearly 400,000 persons annually in the U.S. (Roizman et al., 2013). HSV-2 frequently reactivates to cause genital ulcers and prior HSV-2 infection is associated with an increased risk of HIV acquisition (Roizman et al., 2013). Infants who survive HSV-1 or HSV-2 infections often experience life-long sequellae and periodic recurrent lesions (Kimberlin 2007 and James et al., 2009). VZV reactivates in up to half of older adults (Cohen 2013), and pain associated with the classic Zoster (shingles) rash and post-rash neuralgia can be excruciating. HCMV reactivation is associated with increased incidence of restenosis after angioplasty (Popovic et al., 2012), and also causes significant morbidity and mortality in recipients of bone marrow and solid organ transplants (Snydman 2008). Latent EBV infection is associated with a variety of cancers including Burkitt's lymphoma, two types of Hodgkin's lymphoma, non-Hodgkin's lymphoma, nasopharyngeal carcinoma, and post-transplant lymphoproliferative disease. Latent KSHV infection can lead to three types of cancer: Kaposi's sarcoma, pleural effusion lymphoma, and Castleman's disease (Damania & Cesarman 2013).

Veterinary herpesviruses also take a significant toll on livestock. Marek's disease is highly contagious, spreading rapidly through flocks of chickens that have not been vaccinated. It causes T cell lymphoma with infiltration of nerves and somatic organs, leading to paralysis and death in up to 80% of infected birds (Hirari, 2001). In addition, vaccine efficacy has declined with a concomitant increase in Marek's virus virulence (Gimeno, 2008). Pseudorabies (PRV) is the second most economically important viral disease of swine. Although PRV does not cause illness in adult swine, infection of pregnant sows results in a high incidence of abortion or resorption (Smith, 1997). Piglets infected with PRV suffer coughing, sneezing, fever, constipation, and a variety of neurologic symptoms. Mortality in piglets less than one month of age is close to 100%, but declines rapidly with age (Nauwynck et al., 2007). Ruminants and dogs and cats are also susceptible to lethal PRV infection (Fenner et al., 1993). In cattle, symptoms include intense itching followed by neurological signs and death. In dogs, intense itching is accompanied by jaw and pharyngeal paralysis and subsequent death (Decaro et al., 2008). In cats, usually no symptoms are observed because the disease is so rapidly fatal (Gaskell et al., 2007). Bovine herpesviruses (BHV) cause a variety of illnesses in young cattle, and can also cause abortion. Although the illnesses caused by BHV are mostly not life-threatening, it is an economically important disease because infection may trigger a decline in meat and milk production and affect trade restrictions (Nandi et al., 2009). Equine herpesviruses typically cause respiratory disease, but certain species also cause myeloencephalopathy in horses, abortion and occasionally neonatal mortality due to pneumonia (Fortier et al., 2010). The herpesviruses of various fish species can cause significant mortality in aquaculture settings, particularly at the fingerling stage (Hanson et al., 2011). Importantly, all of these viruses share the same basic genomic replication mechanisms, so if the presumed mechanism by which the NTS enzymes inhibit HSV-1 and HSV-2 is correct, most of the other herpesvirus pathogens should also be highly sensitive to NTS inhibitors. Development of NTS inhibitors into anti-herpesvirus drugs would be particularly valuable in cases like HCMV, where current antiviral therapies frequently drive resistance and are plagued by toxicity issues (Weller and Kuchta, 2013). Finally, NTS inhibitors may be promising candidates for pan anti-herpesvirus drug development due to similarities in replication mechanisms of all the herpesviruses.

2. Infection and Latency

Enveloped herpesvirus particles fuse with the plasma membrane of a cell, releasing viral regulatory proteins and the viral capsid containing the linear double-stranded DNA genome into the cytoplasm. The capsids deliver the viral genome to the nucleus via release through nuclear pores, whereupon the genome circularizes and becomes transcriptionally active. Viral infection at this point can proceed by two patterns, lytic or latent. In the lytic cycle, coordinated phases of viral transcription lead to expression of the viral regulatory proteins, viral enzymes, and concurrently with the onset of DNA replication, the viral structural proteins. Nascent viral capsids assemble in the nucleus and then bud through the nuclear membranes to acquire their envelope (Mettenleiter et al., 2009). Release from the cells is primarily lytic, resulting in the death of the cell. Alternatively, the virus may enter a latent state, where transcription is limited to a few viral regulatory loci and viral DNA replication is strictly limited. Upon recognition of appropriate cellular stimuli, viral transcription reverts to the lytic pattern and productive viral replication occurs.

Initial infections with alpha herpesviruses are lytic, resulting in dispersion of the virus to other cells and organs. These viruses establish latency in the unique environment of the neuron, and also in satellite cells in the case of VZV. During latency, replication of alpha herpesvirus DNA may occur at a low level because latently infected neurons contain multiple copies of the genome (Chen et al., 2002; Wang et al., 2005). Once latency is established, DNA replication increases markedly only during a reactivation event. Initial infections with beta herpesviruses are typically non-lytic but may cause cell-cell fusion. The gamma herpesviruses stimulate proliferation of infected cells, replicating their DNA along with cellular DNA replication to transmit copies of the viral genome to daughter cells (Longnecker et al., 2013). All the herpesviruses cause episodic lytic infection of at least some cell types, allowing them to be shed from mucosal surfaces to facilitate transmission to uninfected individuals.

3. Genomic Replication

Circularization of the linear double-stranded herpesvirus DNA occurs in the nucleus shortly after viral uncoating, presumably through a recombination-mediated event. Replication of the viral DNA occurs in the nucleus within three-dimensional domains termed replication compartments (Quinlan et al., 1984). DNA replication is thought to employ a double-stranded rolling circle mechanism [reviewed in (Weller & Coen 2012; Lehman & Boehmer 1999)]. In preparation for viral DNA replication, virus-encoded transcriptional activators upregulate expression of proteins involved in nucleic acid metabolism. DNA replication then initiates at one of three viral origins of DNA replication and is mediated through action of the viral ICP6 origin binding protein. (All viral gene names in this section are for HSV-1). DNA synthesis is primed by the viral helicase/primase complex (pUL5, pUL8, and pUL52). DNA elongation occurs by coupled leading- and lagging-strand DNA synthesis through formation of a replication fork that is grossly similar to the forks that replicate cellular DNA. DNA synthesis is catalyzed by the pUL30 DNA polymerase/UL42 processivity protein complex that also possesses 5'-3' exonuclease, 3'-5' exonuclease, and RNase H activities. Helical torsion is relieved by the viral helicase/primase complex, and proper replication fork initiation, architecture and dynamics are promoted by the ICP8 single-stranded DNA binding protein. The initial product of DNA replication is a head-to-tail concatamer, but later in the replication cycle complex branched concatamers accumulate through recombination and/or re-initiation mechanisms. The concatamer is cleaved to unit length by the terminase complex (pUL15, pUL28, and pUL33) (Selvarajan et al., 2013) during encapsidation of the viral genome into pre-formed viral capsids.

4. Treatments

Herpesvirus DNA polymerase inhibitors (nucleoside analogs), including acyclovir, famciclovir, valaciclovir, penciclovir, and ganciclovir are the most common forms of treatment. A pyrophosphate analog, foscarnet, also inhibits the herpesvirus DNA polymerases. A DNA helicase inhibitor, AIC316 (pritelivir), was shown to reduce HSV-2 shedding in a phase 2 clinical trial (Wald et al., 2014). N-Methanocarbathymidine (N-MCT) reduces lethality in a mouse model of HSV-2 infection (Quenelle et al., 2011) and a guinea pig model of neonatal herpes (Bernstein et al., 2011). N-MCT also reduces acute and recurrent disease caused by HSV-2 in an adult guinea pig model. The monoamine oxidase inhibitor tranylcypromine (TCP), which also blocks the activity of histone demethylase LSD1, reduces HSV-1 infection of the cornea, trigeminal ganglia and brain of mice, corneal disease, and percentage of mice shedding virus upon induced reactivation (Yao et al., 2014). TCP has also been tested in a rabbit eye model of recurrent infection with HSV-1 and the mouse and guinea pig models of HSV-2 genital infection. An acyclic nucleoside phosphonate, PMEO-DAPym, inhibits HSV replication in a variety of cultured cell types by targeting the viral DNA polymerase (Balzarini et al., 2013). The HIV integrase inhibitor, Raltegravir (JT compound #11), has a small amount of inhibitory activity against replication of several herpesviruses in cultured cells (Zhou et al., 2014; Yan et al., 2014) and appears to target the polymerase processivity factor UL42 (Zhou et al., 2014). Two other integrase inhibitors, XZ15 and XZ45, reduce replication of HSV-1 in cell culture by approximately 800- to 8000-fold, respectively (Yan et al., 2014). XZ45 also inhibits HCMV replication and KSHV gene expression (Yan et al., 2014).

Therapy based on existing drugs such as acyclovir is incompletely effective (Johnston et al., 2012), and viral resistance to current nucleos(t)ide analog therapies is relatively common. Acyclovir resistant variants are particularly prevalent among children, the immunocompromised, and patients with herpetic stromal keratitis (Duan et al., 2008; Wang et al., 2011; Field & Vere Hodge, 2013; Morfin & Thouvenot, 2003; Andrei & Snoeck, 2013). Ganciclovir-resistant variants occur in the naturally circulating viral population (Drew et al., 1993) and can be selected in patients over time (Marfori et al., 2007; Imai et al., 2004; Drew et al., 2001; Drew et al., 1999).

B. Nucleotidyl Transferase Superfamily Enzymes

The inhibitors screened in this project were selected for their ability to inhibit the HIV RNAse H and/or integrase enzymes (or to be close chemical analogs of known inhibitors). The RNAse H and integrase are members of the nucleotidyl transferase superfamily (NTS) whose members share a similar protein fold and enzymatic mechanisms (Yang 1995). Therefore, the presumed targets of the anti-herpesvirus compounds claimed here are viral and/or cellular NTS enzymes. RNAse H enzymes (Hostomsky et al., 1993a; 1993b; 1993c) digest RNA when it is hybridized to DNA. Their physiological roles include removal of RNA primers during DNA synthesis, removal of abortive transcription products, and removal of RNA strands following reverse transcription by viruses or retrotransposons. Integrase enzymes cleave DNA strands and catalyze the covalent insertion of another DNA strand at the cleavage site. Consequently, the presumed mechanism of action for the herpesvirus inhibitors is through suppression of one or more of the nucleolytic or recombination-related activities essential for replication of the herpesvirus DNA.

The NTS family of enzymes includes *E. coli* RNase H I and II (Katayanagi et al., 1990, Yang et al., 1990 and Lai et al., 2000); human RNase H 1 and 2 (Lima et al., 2001, Frank et al., 1998 and Frank et al., 1998); the RuvC Holiday junction resolvase (Ariyoshi et al., 1994); and the Argonaute RNAse (Parker et al., 2004 and Song et al., 2004); retroviral RNase H enzymes including the HIV enzyme (Nowotny 2009); retroviral integrases including the Human immunodeficiency virus (HIV) integrase (Dyda et al., 1994); and the hepatitis B virus (HBV) RNase H (Tavis et al., 2013). These enzymes function in a wide range of nucleic acid metabolic events, including RNA and DNA digestion, DNA recombination, DNA integration, DNA excision, replication fork repair, DNA repair, miRNA maturation, and miRNA-directed RNA cleavage. The canonical RNase H structure contains about 100 amino acids that fold into a 5-stranded β-sheet overlaid with 3 α-helices arranged like an "H". Within the active site are four conserved carboxylates (the "DEDD" motif) that coordinate two divalent cations (Nowotny et al., 2005).

The RNase H enzymatic mechanism is believed to involve both divalent cations (Klumpp et al., 2003; Yang and Steitz, 1995), although a 1-ion mechanism has been proposed (Goedken and Marqusee, 2001; Keck et al., 1998). There are 3 classes of RNAse Hs distinguished by how they bind to their substrates. RNA binding by the "stand-alone" class typified by *E. coli* RNAse H I is promoted by a basic "handle" region (Hostomsky et al., 1993; Kwun et al., 2001). Eukaryotic RNase Hs typically contain a "RHBD" domain that influences nucleic acid binding. Finally, substrate binding by the retroviral enzymes can either be a property of the RNase H domain itself (e.g., Moloney murine leukemia virus) or may require the reverse transcriptase domain to provide sufficient affinity for the nucleic acid substrate (e.g., HIV) (Hostomsky et al., 1993; Smith et al., 1994).

The hepatitis B virus (HBV) RNase H is a NTS enzyme. Mutational analysis of the HBV RNase H revealed the DEDD active site residues to be D702, E731, D750, and D790 (numbering for HBV strain adw2) (Gerelsaikhan et al., 1996; Tavis et al., 2013). Data obtained with the HBV RNase H will be used as an example to establish how anti-RNase H drug discovery can be conducted.

HIV reverse transcription requires a virally encoded RNase H activity to remove the viral RNA after it has been copied into DNA (Freed and Martin, 2007). Consequently, the HIV RNase H activity has attracted much attention as a drug target (Billamboz et al., 2011; Bokesch et al., 2008; Budihas et al., 2005; Chung et al., 2011; Chung et al., 2010; Di et al., 2010; Didierjean et al., 2005; Fuji et al., 2009; Himmel et al., 2009; Himmel et al., 2006; Kirschberg et al., 2009; Klarmann et al., 2002; Klumpp et al., 2003; Klumpp and Mirzadegan, 2006; Shaw-Reid et al., 2003; Su et al., 2010; Takada et al., 2007; Wendeler et al., 2008; Williams et al., 2010). Over 100 anti-HIV RNase H compounds, based on a wide variety of chemical scaffolds, have been reported (Chung et al., 2011; Klumpp and Mirzadegan, 2006). They typically have inhibitory concentration-50% ($IC_{50}$) values in the low µM range. The large majority of these compounds inhibit the RNase H by chelating divalent cations in the active site (Billamboz et al., 2011; Chung et al., 2011; Fuji et al., 2009; Himmel et al., 2009; Kirschberg et al., 2009; Su et al., 2010), but compounds that alter the enzyme's conformation or its interaction with nucleic acids have also been reported (Himmel et al., 2006; Wendeler et al., 2008). The inhibitors typically have $EC_{50}$ values ~10× higher than the $IC_{50}$ values, and they often cause modest cytotoxicity, leading to therapeutic indexes (TI) that are usually <10. Second-generation inhibitors with substantially improved efficacy have been reported, (Billamboz et al., 2011; Chung et al., 2011; Williams et al., 2010), and compounds with efficacy and TI values appropriate for a human drug exist (Himmel et al., 2006; Williams et al., 2010).

None of the anti-HIV RNase H compounds have entered clinical trials yet. This is due in part to their relatively low TI values but also to the large number of approved and developmental anti-HIV drugs, raising doubts about the marketability of anti-HIV RNase H compounds. Despite these challenges, the HIV RNase H remains a target of intensive ongoing drug development, as is evidenced by the large number of groups working in the field (Billamboz et al., 2011; Bokesch et al., 2008; Budihas et al., 2005; Chung et al., 2011; Chung et al., 2010; Di et al., 2010; Didierjean et al., 2005; Fuji et al., 2009; Himmel et al., 2009; Himmel et al., 2006; Kirschberg et al., 2009; Klarmann et al., 2002; Klumpp et al., 2003; Klumpp and Mirzadegan, 2006; Shaw-Reid et al., 2003; Su et al., 2010; Takada et al., 2007; Wendeler et al., 2008; Williams et al., 2010).

Because both the RNase H and integrase are NTS enzymes, some anti-RNase H compounds can inhibit the HIV integrase, and some anti-integrase compounds can inhibit the RNase H (Klarmann et al., 2002, Williams et al., 2010 and Billamboz et al., 2011). Despite this cross-inhibitory potential, resistance mutations to HIV DNA polymerase or integrase drugs have not led to cross-resistance to RNase H inhibitors (Billamboz et al., 2011 and Himmel et al., 2006).

HBV reverse transcription requires two viral enzymatic activities that are both located on the viral reverse transcriptase protein. The DNA polymerase activity synthesizes new DNA and is targeted by the nucleos(t)ide analogs. The RNase H destroys the viral RNA after it has been copied into DNA. Inhibiting the RNAse H would block DNA synthesis and consequently halt viral replication, but anti-HBV RNase H drugs have not been developed because enzyme suitable for drug screening could not be readily made. One of the inventors recently produced active recombinant HBV RNase H and identified 21 inhibitors of the RNase H (Table 1; Tavis et al., 2013 and Hu et al., 2013).

These examples of cross-inhibition of NTS enzymes by RNase H and integrase inhibitors provide the precedent upon which these studies with the herpesviruses rest.

C. Chemical Entities

The compounds of the present disclosure appear to inhibit a different enzymatic activity than the existing anti-herpesvirus drugs, and do so with a striking capacity to suppress virus replication at very low toxicity to uninfected cells. This implies that they will be effective against viral isolates resistant to the existing drugs and suggests that these drugs could be combined effectively with the existing drugs to both increase efficacy and to reduce the rate of resistance development to either drug. Furthermore, many of these compounds were more effective than a currently accepted first line therapy, acyclovir (Table 2 and FIG. 2), indicating that they may be more effective than the existing drugs when formulated for pharmaceutical delivery.

1. Compounds of the Present Disclosure

The compounds of the present disclosure are represented by the formulas included below:

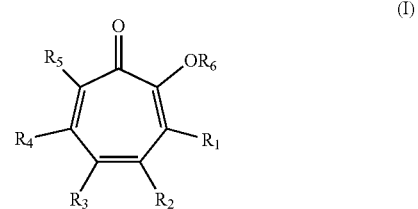

(I)

wherein: $R_1$ is hydrogen, hydroxyl, alkyl$_{(C\leq6)}$, or substituted alkyl$_{(C\leq6)}$; $R_2$ is hydrogen, alkyl$_{(C\leq6)}$, substituted alkyl$_{(C\leq6)}$, or when taken together with $R_3$ is as defined below in Formula Ib; $R_3$ is hydrogen, nitroso, nitro, alkyl$_{(C\leq8)}$, alkenyl$_{(C\leq8)}$, alkynyl$_{(C\leq8)}$, acyloxy$_{(C\leq12)}$, amido$_{(C\leq12)}$, or a substituted version of any of the last five groups, or when taken together with $R_2$ is as defined below in Formula Ib; $R_2$ and $R_3$ when taken together have a formula:

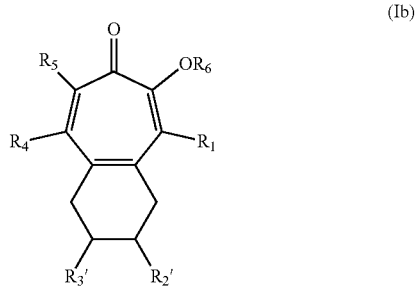

(Ib)

wherein: $R_2'$ and $R_3'$ are each independently hydrogen, alkyl$_{(C\leq4)}$, substituted alkyl$_{(C\leq4)}$, alkenyl$_{(C\leq4)}$, or substituted alkenyl$_{(C≤4)}$; R$_4$ is hydrogen, alkyl$_{(C≤8)}$, alkenyl$_{(C≤8)}$, alkynyl$_{(C≤8)}$, aryl$_{(C≤8)}$, aralkyl$_{(C≤12)}$, or a substituted version of any of the last five groups; R$_5$ is hydrogen, alkyl$_{(C≤6)}$, or a substituted alkyl$_{(C≤6)}$; R$_6$ is hydrogen, acyl$_{(C≤12)}$, arylsulfonyl$_{(C≤12)}$, substituted acyl$_{(C≤12)}$, or substituted arylsulfonyl$_{(C≤12)}$; or

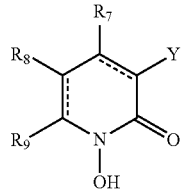

(II)

wherein: R$_7$ is hydrogen, alkyl$_{(C≤6)}$, or a substituted alkyl$_{(C≤6)}$, or when taken together with R$_8$ is as defined below in Formula IIa; R$_8$ is hydrogen, halo, alkyl$_{(C≤6)}$, or substituted alkyl$_{(C≤6)}$, or when taken together with R$_7$ is as defined below in Formula IIa or when taken together with R$_9$ is as defined below in Formula IIb; R$_9$ is hydrogen, alkyl$_{(C≤8)}$, substituted alkyl$_{(C≤8)}$, or oxo, or when taken together with R$_8$ is as defined below in Formula IIb; Y is hydrogen, halo, cyano, alkyl$_{(C≤6)}$, substituted alkyl$_{(C≤6)}$, acyl$_{(C≤6)}$, or substituted alkyl$_{(C≤6)}$;

R$_7$ and R$_8$ when taken together have a formula:

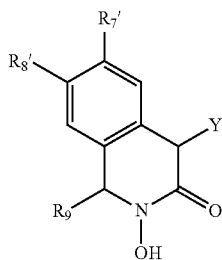

(IIa)

R$_8$ and R$_9$ when taken together have a formula:

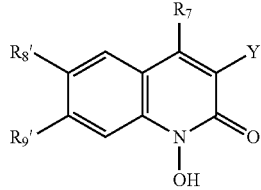

(IIb)

wherein: R$_8$' and R$_9$' are each independently hydrogen, halo, alkyl$_{(C≤6)}$ or substituted alkyl$_{(C≤6)}$; or

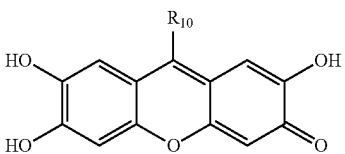

(III)

wherein: R$_{10}$ is alkyl$_{(C≤6)}$, substituted alkyl$_{(C≤6)}$,

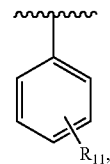

heteroaryl$_{(C≤8)}$, or substituted heteroaryl$_{(C≤8)}$; R$_{11}$ is hydrogen, hydroxy, halo, amino, nitro, cyano, alkyl$_{(C≤6)}$, alkoxy$_{(C≤6)}$, alkylamino$_{(C≤6)}$, dialkylamino$_{(C≤6)}$, or a substituted version of any of the last four groups; or

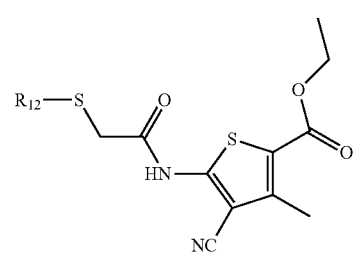

(IV)

wherein: R$_{12}$ is heteroaryl$_{(C≤12)}$ or substituted heteroaryl$_{(C≤12)}$; or (V)

wherein: R$_{13}$ is alkyl$_{(C≤12)}$, or substituted alkyl$_{(C≤12)}$, R$_{14}$, R$_{15}$, R$_{16}$, and R$_{17}$ are each independently hydrogen, halo, alkyl$_{(C≤12)}$, aryl$_{(C≤12)}$, aralkyl$_{(C≤12)}$, alkoxy$_{(C≤12)}$, substituted alkyl$_{(C≤12)}$, substituted aryl$_{(C≤12)}$, substituted aralkyl$_{(C≤12)}$, or substituted alkoxy$_{(C≤12)}$;

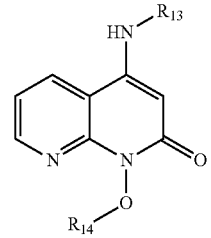

(VI)

wherein: R$_{13}$ is aryl$_{(C≤12)}$, aralkyl$_{(C≤12)}$, or a substituted version of either of these groups; and R$_{14}$ is hydrogen, alkyl$_{(C≤6)}$, or substituted alkyl$_{(C≤6)}$;

(VII)

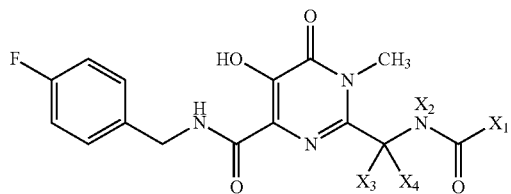

wherein: $X_1$ is aryl$_{(C \leq 12)}$, aralkyl$_{(C \leq 12)}$, heteroaryl$_{(C \leq 12)}$, or a substituted version of any of these groups; and $X_2$, $X_3$, and $X_4$ are each independently selected from hydrogen, alkyl$_{(C \leq 8)}$, or substituted alkyl$_{(C \leq 8)}$; or a pharmaceutically acceptable salt thereof.

Other particular compounds according to the present invention include:

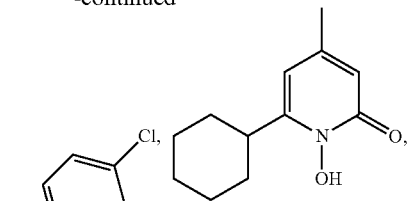

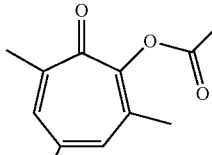

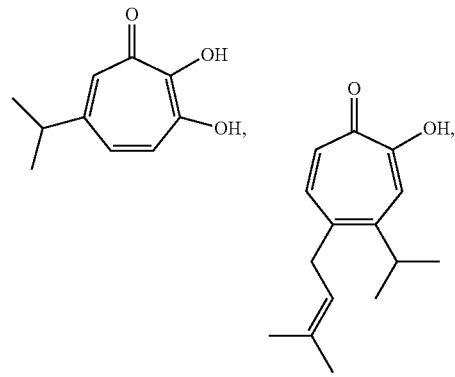

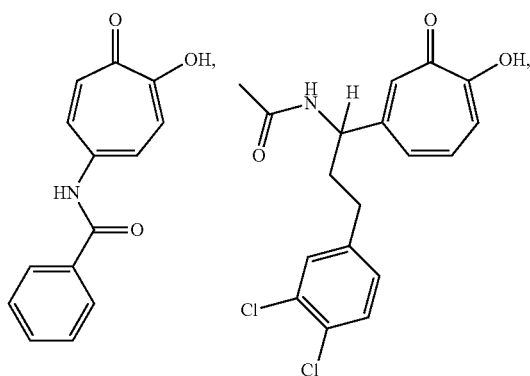

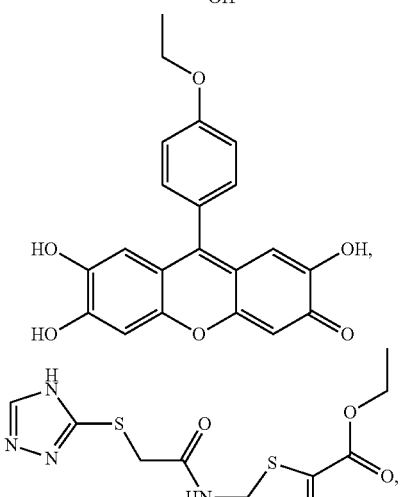

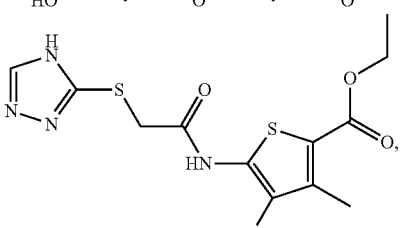

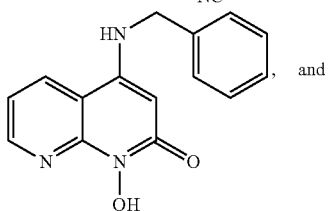

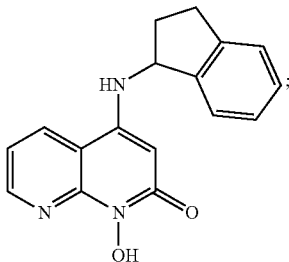

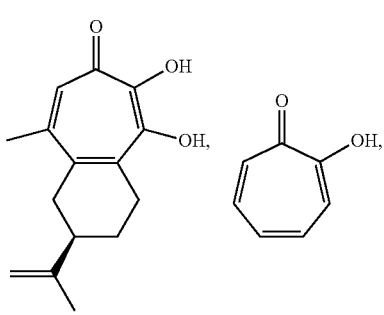

or a pharmaceutically acceptable salt thereof.

Compounds of the invention may contain one or more asymmetrically-substituted carbon or nitrogen atoms, and may be isolated in optically active or racemic form. Thus, all chiral, diastereomeric, racemic form, epimeric form, and all geometric isomeric forms of a chemical formula are intended, unless the specific stereochemistry or isomeric form is specifically indicated. Compounds may occur as racemates and racemic mixtures, single enantiomers, diastereomeric mixtures and individual diastereomers. In some embodiments, a single diastereomer is obtained. The chiral centers of the compounds of the present invention can have the S or the R configuration.

Chemical formulas used to represent compounds of the invention will typically only show one of possibly several different tautomers. For example, many types of ketone groups are known to exist in equilibrium with corresponding enol groups. Similarly, many types of imine groups exist in equilibrium with enamine groups. Regardless of which tautomer is depicted for a given compound, and regardless of which one is most prevalent, all tautomers of a given chemical formula are intended.

Compounds of the invention may also have the advantage that they may be more efficacious than, be less toxic than, be longer acting than, be more potent than, produce fewer side effects than, be more easily absorbed than, and/or have a better pharmacokinetic profile (e.g., higher oral bioavailability and/or lower clearance) than, and/or have other useful pharmacological, physical, or chemical properties over, compounds known in the prior art, whether for use in the indications stated herein or otherwise.

In addition, atoms making up the compounds of the present invention are intended to include all isotopic forms of such atoms. Isotopes, as used herein, include those atoms having the same atomic number but different mass numbers. By way of general example and without limitation, isotopes of hydrogen include tritium and deuterium, and isotopes of carbon include $^{13}C$ and $^{14}C$. Similarly, it is contemplated that one or more carbon atom(s) of a compound of the present invention may be replaced by a silicon atom(s). Furthermore, it is contemplated that one or more oxygen atom(s) of a compound of the present invention may be replaced by a sulfur or selenium atom(s).

Compounds of the present invention may also exist in prodrug form. Since prodrugs are known to enhance numerous desirable qualities of pharmaceuticals (e.g., solubility, bioavailability, manufacturing, etc.), the compounds employed in some methods of the invention may, if desired, be delivered in prodrug form. Thus, the invention contemplates prodrugs of compounds of the present invention as well as methods of delivering prodrugs. Prodrugs of the compounds employed in the invention may be prepared by modifying functional groups present in the compound in such a way that the modifications are cleaved, either in routine manipulation or in vivo, to the parent compound. Accordingly, prodrugs include, for example, compounds described herein in which a hydroxy, amino, or carboxy group is bonded to any group that, when the prodrug is administered to a subject, cleaves to form a hydroxy, amino, or carboxylic acid, respectively.

It should be recognized that the particular anion or cation forming a part of any salt of this invention is not critical, so long as the salt, as a whole, is pharmacologically acceptable. Additional examples of pharmaceutically acceptable salts and their methods of preparation and use are presented in *Handbook of Pharmaceutical Salts: Properties, and Use* (2002), which is incorporated herein by reference.

2. Chemical Definitions

When used in the context of a chemical group, "hydrogen" means —H; "hydroxy" means —OH; "oxo" means =O; "halo" means independently —F, —Cl, —Br or —I; "amino" means —NH$_2$; "hydroxyamino" means —NHOH; "nitro" means —NO$_2$; imino means =NH; "cyano" means —CN; "isocyanate" means —N=C=O; "azido" means —N$_3$; in a monovalent context "phosphate" means —OP(O)(OH)$_2$ or a deprotonated form thereof; in a divalent context "phosphate" means —OP(O)(OH)O— or a deprotonated form thereof; "mercapto" means —SH; "thio" means =S; "sulfonyl" means —S(O)$_2$—; and "sulfinyl" means —S(O)—.

In the context of chemical formulas, the symbol "—" means a single bond, "=" means a double bond, and "≡" means triple bond. The symbol "----" represents an optional bond, which if present is either single or double. The symbol "⟶" represents a single bond or a double bond. Thus, for example, the formula

includes

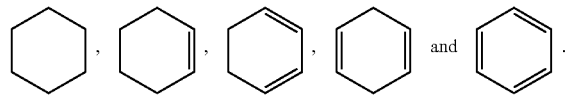

And it is understood that no one such ring atom forms part of more than one double bond. Furthermore, it is noted that the covalent bond symbol "—", when connecting one or two stereogenic atoms, does not indicate any preferred stereochemistry. Instead, it cover all stereoisomers as well as mixtures thereof. The symbol "⁓", when drawn perpendicularly across a bond (e.g.,

for methyl) indicates a point of attachment of the group. It is noted that the point of attachment is typically only identified in this manner for larger groups in order to assist the reader in unambiguously identifying a point of attachment. The symbol "◂" means a single bond where the group attached to the thick end of the wedge is "out of the page." The symbol "⫽" means a single bond where the group attached to the thick end of the wedge is "into the page". The symbol "⁓" means a single bond where the geometry around a double bond (e.g., either E or Z) is undefined. Both options, as well as combinations thereof are therefore intended. Any undefined valency on an atom of a structure shown in this application implicitly represents a hydrogen atom bonded to that atom. A bold dot on a carbon atom indicates that the hydrogen attached to that carbon is oriented out of the plane of the paper.

When a group "R" is depicted as a "floating group" on a ring system, for example, in the formula:

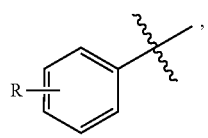

then R may replace any hydrogen atom attached to any of the ring atoms, including a depicted, implied, or expressly defined hydrogen, so long as a stable structure is formed. When a group "R" is depicted as a "floating group" on a fused ring system, as for example in the formula:

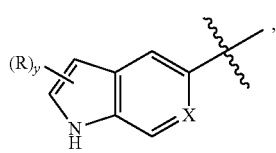

then R may replace any hydrogen attached to any of the ring atoms of either of the fused rings unless specified otherwise. Replaceable hydrogens include depicted hydrogens (e.g., the hydrogen attached to the nitrogen in the formula above), implied hydrogens (e.g., a hydrogen of the formula above that is not shown but understood to be present), expressly defined hydrogens, and optional hydrogens whose presence depends on the identity of a ring atom (e.g., a hydrogen attached to group X, when X equals —CH—), so long as a stable structure is formed. In the example depicted, R may reside on either the 5-membered or the 6-membered ring of the fused ring system. In the formula above, the subscript letter "y" immediately following the group "R" enclosed in parentheses, represents a numeric variable. Unless specified otherwise, this variable can be 0, 1, 2, or any integer greater than 2, only limited by the maximum number of replaceable hydrogen atoms of the ring or ring system.

For the groups and classes below, the following parenthetical subscripts further define the group/class as follows: "(Cn)" defines the exact number (n) of carbon atoms in the group/class. "(C≤n)" defines the maximum number (n) of carbon atoms that can be in the group/class, with the minimum number as small as possible for the group in question, e.g., it is understood that the minimum number of carbon atoms in the group "alkenyl$_{(C≤8)}$" or the class "alkene$_{(C≤8)}$" is two. For example, "alkoxy$_{(C≤10)}$" designates those alkoxy groups having from 1 to 10 carbon atoms. (Cn–n') defines both the minimum (n) and maximum number (n') of carbon atoms in the group. Similarly, "alkyl$_{(C2-10)}$" designates those alkyl groups having from 2 to 10 carbon atoms.

The term "saturated" as used herein means the compound or group so modified has no carbon-carbon double and no carbon-carbon triple bonds, except as noted below. In the case of substituted versions of saturated groups, one or more carbon oxygen double bond or a carbon nitrogen double bond may be present. And when such a bond is present, then carbon-carbon double bonds that may occur as part of keto-enol tautomerism or imine/enamine tautomerism are not precluded.

The term "aliphatic" when used without the "substituted" modifier signifies that the compound/group so modified is an acyclic or cyclic, but non-aromatic hydrocarbon compound or group. In aliphatic compounds/groups, the carbon atoms can be joined together in straight chains, branched chains, or non-aromatic rings (alicyclic). Aliphatic compounds/groups can be saturated, that is joined by single bonds (alkanes/alkyl), or unsaturated, with one or more double bonds (alkenes/alkenyl) or with one or more triple bonds (alkynes/alkynyl).

The term "alkyl" when used without the "substituted" modifier refers to a monovalent saturated aliphatic group with a carbon atom as the point of attachment, a linear or branched, cyclo, cyclic or acyclic structure, and no atoms other than carbon and hydrogen. Thus, as used herein cycloalkyl is a subset of alkyl, with the carbon atom that forms the point of attachment also being a member of one or more non-aromatic ring structures wherein the cycloalkyl group consists of no atoms other than carbon and hydrogen. As used herein, the term does not preclude the presence of one or more alkyl groups (carbon number limitation permitting) attached to the ring or ring system. The groups —CH$_3$ (Me), —CH$_2$CH$_3$ (Et), —CH$_2$CH$_2$CH$_3$ (n-Pr or propyl), —CH(CH$_3$)$_2$ (i-Pr, $^i$Pr or isopropyl), —CH(CH$_2$)$_2$ (cyclopropyl), —CH$_2$CH$_2$CH$_2$CH$_3$ (n-Bu), —CH(CH$_3$)CH$_2$CH$_3$ (sec-butyl), —CH$_2$CH(CH$_3$)$_2$ (isobutyl), —C(CH$_3$)$_3$ (tert-butyl, t-butyl, t-Bu or $^t$Bu), —CH$_2$C(CH$_3$)$_3$ (neo-pentyl), cyclobutyl, cyclopentyl, cyclohexyl, and cyclohexylmethyl are non-limiting examples of alkyl groups. The term "alkanediyl" when used without the "substituted" modifier refers to a divalent saturated aliphatic group, with one or two saturated carbon atom(s) as the point(s) of attachment, a linear or branched, cyclo, cyclic or acyclic structure, no carbon-carbon double or triple bonds, and no atoms other than carbon and hydrogen. The groups, —CH$_2$— (methylene), —CH$_2$CH$_2$—, —CH$_2$C(CH$_3$)$_2$CH$_2$—, —CH$_2$CH$_2$CH$_2$—, and

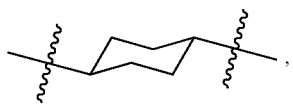 [SMILES: *C1CCC(*)CC1]

are non-limiting examples of alkanediyl groups. The term "alkylidene" when used without the "substituted" modifier refers to the divalent group =CRR' in which R and R' are independently hydrogen, alkyl, or R and R' are taken together to represent an alkanediyl having at least two carbon atoms. Non-limiting examples of alkylidene groups include: =CH$_2$, =CH(CH$_2$CH$_3$), and =C(CH$_3$)$_2$. An "alkane" refers to the compound H—R, wherein R is alkyl as this term is defined above. When any of these terms is used with the "substituted" modifier one or more hydrogen atom has been independently replaced by —OH, —F, —Cl, —Br, —I, —NH$_2$, —NO$_2$, —CO$_2$H, —CO$_2$CH$_3$, —CN, —SH, —OCH$_3$, —OCH$_2$CH$_3$, —C(O)CH$_3$, —NHCH$_3$, —NHCH$_2$CH$_3$, —N(CH$_3$)$_2$, —C(O)NH$_2$, —OC(O)CH$_3$, or —S(O)$_2$NH$_2$. The following groups are non-limiting examples of substituted alkyl groups: —CH$_2$OH, —CH$_2$Cl, —CF$_3$, —CH$_2$CN, —CH$_2$C(O)OH, —CH$_2$C(O)OCH$_3$, —CH$_2$C(O)NH$_2$, —CH$_2$C(O)CH$_3$, —CH$_2$OCH$_3$, —CH$_2$OC(O)CH$_3$, —CH$_2$NH$_2$, —CH$_2$N(CH$_3$)$_2$, and —CH$_2$CH$_2$Cl. The term "haloalkyl" is a subset of substituted alkyl, in which one or more hydrogen atoms has been substituted with a halo group and no other atoms aside from carbon, hydrogen and halogen are present. The group, —CH$_2$Cl is a non-limiting example of a haloalkyl. The term "fluoroalkyl" is a subset of substituted alkyl, in which one or more hydrogen has been substituted with a fluoro group and no other atoms aside from carbon, hydrogen and fluorine are present. The groups, —CH$_2$F, —CF$_3$, and —CH$_2$CF$_3$ are non-limiting examples of fluoroalkyl groups.

The term "alkenyl" when used without the "substituted" modifier refers to an monovalent unsaturated aliphatic group with a carbon atom as the point of attachment, a linear or branched, cyclo, cyclic or acyclic structure, at least one nonaromatic carbon-carbon double bond, no carbon-carbon triple bonds, and no atoms other than carbon and hydrogen. Non-limiting examples of alkenyl groups include: —CH=CH$_2$ (vinyl), —CH=CHCH$_3$, CH=CHCH$_2$CH$_3$, —CH$_2$CH=CH$_2$ (allyl), —CH$_2$CH=CHCH$_3$, and —CH=CHCH=CH$_2$. The term "alkenediyl" when used without the "substituted" modifier refers to a divalent unsaturated aliphatic group, with two carbon atoms as points of attachment, a linear or branched, cyclo, cyclic or acyclic structure, at least one nonaromatic carbon-carbon double bond, no carbon-carbon triple bonds, and no atoms other than carbon and hydrogen. The groups, —CH=CH—, —CH=C(CH$_3$)CH$_2$—, —CH=CHCH$_2$—, and

are non-limiting examples of alkenediyl groups. It is noted that while the alkenediyl group is aliphatic, once connected at both ends, this group is not precluded from forming part of an aromatic structure. The terms "alkene" or "olefin" are synonymous and refer to a compound having the formula H—R, wherein R is alkenyl as this term is defined above. A "terminal alkene" refers to an alkene having just one carbon-carbon double bond, wherein that bond forms a vinyl group at one end of the molecule. When any of these terms are used with the "substituted" modifier one or more hydrogen atom has been independently replaced by —OH, —F, —Cl, —Br, —I, —NH$_2$, —NO$_2$, —CO$_2$H, —CO$_2$CH$_3$, —CN, —SH, —OCH$_3$, —OCH$_2$CH$_3$, —C(O)CH$_3$, —NHCH$_3$, —NHCH$_2$CH$_3$, —N(CH$_3$)$_2$, —C(O)NH$_2$, —OC(O)CH$_3$, or —S(O)$_2$NH$_2$. The groups, —CH=CHF, —CH=CHCl and —CH=CHBr, are non-limiting examples of substituted alkenyl groups.

The term "alkynyl" when used without the "substituted" modifier refers to an monovalent unsaturated aliphatic group with a carbon atom as the point of attachment, a linear or branched, cyclo, cyclic or acyclic structure, at least one carbon-carbon triple bond, and no atoms other than carbon and hydrogen. As used herein, the term alkynyl does not preclude the presence of one or more non-aromatic carbon-carbon double bonds. The groups, —C≡CH, —C≡CCH$_3$, and —CH$_2$C≡CCH$_3$, are non-limiting examples of alkynyl groups. An "alkyne" refers to the compound H—R, wherein R is alkynyl. When any of these terms are used with the "substituted" modifier one or more hydrogen atom has been independently replaced by —OH, —F, —Cl, —Br, —I, —NH$_2$, —NO$_2$, —CO$_2$H, —CO$_2$CH$_3$, —CN, —SH, —OCH$_3$, —OCH$_2$CH$_3$, —C(O)CH$_3$, —NHCH$_3$, —NHCH$_2$CH$_3$, —N(CH$_3$)$_2$, —C(O)NH$_2$, —OC(O)CH$_3$, or —S(O)$_2$NH$_2$.

The term "aryl" when used without the "substituted" modifier refers to a monovalent unsaturated aromatic group with an aromatic carbon atom as the point of attachment, said carbon atom forming part of a one or more six-membered aromatic ring structure, wherein the ring atoms are all carbon, and wherein the group consists of no atoms other than carbon and hydrogen. If more than one ring is present, the rings may be fused or unfused. As used herein, the term does not preclude the presence of one or more alkyl or aralkyl groups (carbon number limitation permitting) attached to the first aromatic ring or any additional aromatic ring present. Non-limiting examples of aryl groups include phenyl (Ph), methylphenyl, (dimethyl)phenyl, —C$_6$H$_4$CH$_2$CH$_3$ (ethylphenyl), naphthyl, and a monovalent group derived from biphenyl. The term "arenediyl" when used without the "substituted" modifier refers to a divalent aromatic group with two aromatic carbon atoms as points of attachment, said carbon atoms forming part of one or more six-membered aromatic ring structure(s) wherein the ring atoms are all carbon, and wherein the monovalent group consists of no atoms other than carbon and hydrogen. As used herein, the term does not preclude the presence of one or more alkyl, aryl or aralkyl groups (carbon number limitation permitting) attached to the first aromatic ring or any additional aromatic ring present. If more than one ring is present, the rings may be fused or unfused. Unfused rings may be connected via one or more of the following: a covalent bond, alkanediyl, or alkenediyl groups (carbon number limitation permitting). Non-limiting examples of arenediyl groups include:

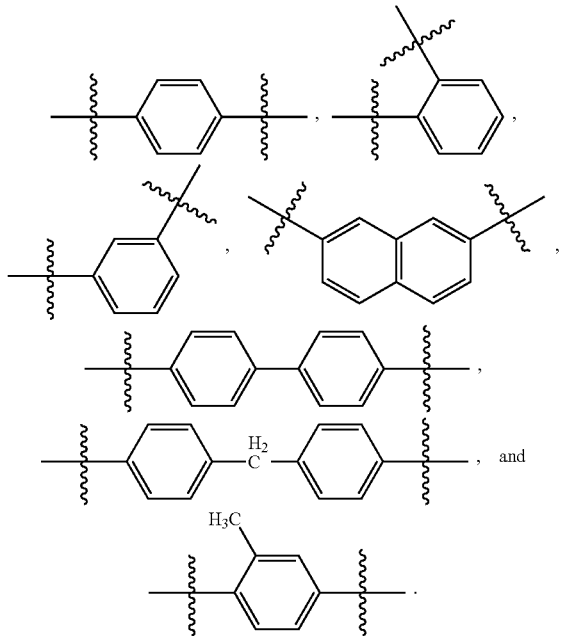

An "arene" refers to the compound H—R, wherein R is aryl as that term is defined above. Benzene and toluene are non-limiting examples of arenes. When any of these terms are used with the "substituted" modifier one or more hydrogen atom has been independently replaced by —OH, —F, —Cl, —Br, —I, —NH$_2$, —NO$_2$, —CO$_2$H, —CO$_2$CH$_3$, —CN, —SH, —OCH$_3$, —OCH$_2$CH$_3$, —C(O)CH$_3$, —NHCH$_3$, —NHCH$_2$CH$_3$, —N(CH$_3$)$_2$, —C(O)NH$_2$, —OC(O)CH$_3$, or —S(O)$_2$NH$_2$.

The term "aralkyl" when used without the "substituted" modifier refers to the monovalent group -alkanediyl-aryl, in which the terms alkanediyl and aryl are each used in a manner consistent with the definitions provided above. Non-limiting examples of aralkyls are: phenylmethyl (benzyl, Bn) and 2-phenyl-ethyl. In some embodiments of the term "aralkyl", the alkanediyl is a cycloalkyl group which is fused with the aryl group. As such, the alkanediyl group can have more than point of attachment to the aryl group. A non-limiting example of aralkyl wherein the alkanediyl group is fused with the aryl group is 1-indanyl. When the term aralkyl is used with the "substituted" modifier one or more hydrogen atom from the alkanediyl and/or the aryl group has been independently replaced by —OH, —F, —Cl, —Br, —I, —NH$_2$, —NO$_2$, —CO$_2$H, —CO$_2$CH$_3$, —CN, —SH, —OCH$_3$, —OCH$_2$CH$_3$, —C(O)CH$_3$, —NHCH$_3$, —NHCH$_2$CH$_3$, —N(CH$_3$)$_2$, —C(O)NH$_2$, —OC(O)CH$_3$, or —S(O)$_2$NH$_2$. Non-limiting examples of substituted aralkyls are: (3-chlorophenyl)-methyl, and 2-chloro-2-phenyl-eth-1-yl.

The term "heteroaryl" when used without the "substituted" modifier refers to a monovalent aromatic group with an aromatic carbon atom or nitrogen atom as the point of attachment, said carbon atom or nitrogen atom forming part of one or more aromatic ring structures wherein at least one of the ring atoms is nitrogen, oxygen or sulfur, and wherein the heteroaryl group consists of no atoms other than carbon, hydrogen, aromatic nitrogen, aromatic oxygen and aromatic sulfur. If more than one ring is present, the rings may be fused or unfused. As used herein, the term does not preclude the presence of one or more alkyl, aryl, and/or aralkyl groups (carbon number limitation permitting) attached to the aromatic ring or aromatic ring system. Non-limiting examples of heteroaryl groups include furanyl, imidazolyl, indolyl, indazolyl (Im), isoxazolyl, methylpyridinyl, oxazolyl, phenylpyridinyl, pyridinyl, pyrrolyl, pyrimidinyl, pyrazinyl, quinolyl, quinazolyl, quinoxalinyl, triazinyl, tetrazolyl, thiazolyl, thienyl, and triazolyl. The term "N-heteroaryl" refers to a heteroaryl group with a nitrogen atom as the point of attachment. The term "heteroarenediyl" when used without the "substituted" modifier refers to an divalent aromatic group, with two aromatic carbon atoms, two aromatic nitrogen atoms, or one aromatic carbon atom and one aromatic nitrogen atom as the two points of attachment, said atoms forming part of one or more aromatic ring structure(s) wherein at least one of the ring atoms is nitrogen, oxygen or sulfur, and wherein the divalent group consists of no atoms other than carbon, hydrogen, aromatic nitrogen, aromatic oxygen and aromatic sulfur. If more than one ring is present, the rings may be fused or unfused. Unfused rings may be connected via one or more of the following: a covalent bond, alkanediyl, or alkenediyl groups (carbon number limitation permitting). As used herein, the term does not preclude the presence of one or more alkyl, aryl, and/or aralkyl groups (carbon number limitation permitting) attached to the aromatic ring or aromatic ring system. Non-limiting examples of heteroarenediyl groups include:

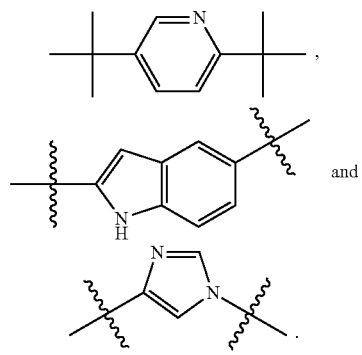

A "heteroarene" refers to the compound H—R, wherein R is heteroaryl. Pyridine and quinoline are non-limiting examples of heteroarenes. When these terms are used with the "substituted" modifier one or more hydrogen atom has been independently replaced by —OH, —F, —Cl, —Br, —I, —NH$_2$, —NO$_2$, —CO$_2$H, —CO$_2$CH$_3$, —CN, —SH, —OCH$_3$, —OCH$_2$CH$_3$, —C(O)CH$_3$, —NHCH$_3$, —NHCH$_2$CH$_3$, —N(CH$_3$)$_2$, —C(O)NH$_2$, —OC(O)CH$_3$, or —S(O)$_2$NH$_2$.

The term "acyl" when used without the "substituted" modifier refers to the group —C(O)R, in which R is a hydrogen, alkyl, aryl, aralkyl or heteroaryl, as those terms are defined above. The groups, —CHO, —C(O)CH$_3$ (acetyl, Ac), —C(O)CH$_2$CH$_3$, —C(O)CH$_2$CH$_2$CH$_3$, —C(O)CH(CH$_3$)$_2$, —C(O)CH(CH$_2$)$_2$, —C(O)C$_6$H$_5$, C$_6$H$_5$, C(O)C$_6$H$_4$CH$_3$, —C(O)CH$_2$C$_6$H$_5$, —C(O)(imidazolyl) are non-limiting examples of acyl groups. A "thioacyl" is defined in an analogous manner, except that the oxygen atom of the group —C(O)R has been replaced with a sulfur atom, —C(S)R. The term "aldehyde" corresponds to an alkane, as defined above, wherein at least one of the hydrogen atoms has been replaced with a —CHO group. When any of these terms are used with the "substituted" modifier one or more hydrogen atom (including a hydrogen atom directly attached the carbonyl or thiocarbonyl group, if any) has been independently replaced by —OH, —F, —Cl, —Br, —I, —NH$_2$, —NO$_2$, —CO$_2$H, —CO$_2$CH$_3$, —CN, —SH, —OCH$_3$, —OCH$_2$CH$_3$, —C(O)CH$_3$, —NHCH$_3$, —NHCH$_2$CH$_3$, —N(CH$_3$)$_2$, —C(O)NH$_2$, —OC(O)CH$_3$, or —S(O)$_2$NH$_2$. The groups, —C(O)CH$_2$CF$_3$, —CO$_2$H (carboxyl), —CO$_2$CH$_3$ (methylcarboxyl), —CO$_2$CH$_2$CH$_3$, —C(O)NH$_2$ (carbamoyl), and —CON(CH$_3$)$_2$, are non-limiting examples of substituted acyl groups.

The term "alkoxy" when used without the "substituted" modifier refers to the group —OR, in which R is an alkyl, as that term is defined above. Non-limiting examples of alkoxy groups include: —OCH$_3$ (methoxy), —OCH$_2$CH$_3$ (ethoxy), —OCH$_2$CH$_2$CH$_3$, —OCH(CH$_3$)$_2$ (isopropoxy), —O(CH$_3$)$_3$ (tert-butoxy), —OCH(CH$_2$)$_2$, —O-cyclopentyl, and —O-cyclohexyl. The terms "alkenyloxy", "alkynyloxy", "aryloxy", "aralkoxy", "heteroaryloxy", "heterocycloalkoxy", and "acyloxy", when used without the "substituted" modifier, refers to groups, defined as —OR, in which R is alkenyl, alkynyl, aryl, aralkyl, heteroaryl, heterocycloalkyl, and acyl, respectively. The term "alkoxydiyl" refers to the divalent group —O— alkanediyl-, —O—alkanediyl-O—, or -alkanediyl-O-alkanediyl-. The term "alkylthio" and "acylthio" when used without the "substituted" modifier refers to the group —SR, in which R is an alkyl and acyl, respectively. The term "alcohol" corresponds to an alkane, as defined above, wherein at least one of the hydrogen atoms has been replaced with a hydroxy group. The term "ether" corresponds to an alkane, as defined above, wherein at least one of the hydrogen atoms has been replaced with an alkoxy group. When any of these terms is used with the "substituted" modifier one or more hydrogen atom has been independently replaced by —OH, —F, —Cl, —Br, —I, —NH$_2$, —NO$_2$, —CO$_2$H, —CO$_2$CH$_3$, —CN, —SH, —OCH$_3$, —OCH$_2$CH$_3$, —C(O)CH$_3$, —NHCH$_3$, —NHCH$_2$CH$_3$, —N(CH$_3$)$_2$, —C(O)NH$_2$, —OC(O)CH$_3$, or —S(O)$_2$NH$_2$.

The term "alkylamino" when used without the "substituted" modifier refers to the group —NHR, in which R is an alkyl, as that term is defined above. Non-limiting examples of alkylamino groups include: —NHCH$_3$ and —NHCH$_2$CH$_3$. The term "dialkylamino" when used without the "substituted" modifier refers to the group —NRR', in which R and R' can be the same or different alkyl groups, or R and R' can be taken together to represent an alkanediyl. Non-limiting examples of dialkylamino groups include: —N(CH$_3$)$_2$, —N(CH$_3$)(CH$_2$CH$_3$), and N-pyrrolidinyl. The terms "alkoxyamino", "alkenylamino", "alkynylamino", "arylamino", "aralkylamino", "heteroarylamino", "heterocycloalkylamino" and "alkylsulfonylamino" when used without the "substituted" modifier, refers to groups, defined as —NHR, in which R is alkoxy, alkenyl, alkynyl, aryl, aralkyl, heteroaryl, heterocycloalkyl, and alkylsulfonyl, respectively. A non-limiting example of an arylamino group is —NHC$_6$H$_5$. The term "amido" (acylamino), when used without the "substituted" modifier, refers to the group —NHR, in which R is acyl, as that term is defined above. A non-limiting example of an amido group is —NHC(O)CH$_3$. The term "alkylimino" when used without the "substituted" modifier refers to the divalent group =NR, in which R is an alkyl, as that term is defined above. The term "alkylaminodiyl" refers to the divalent group —NH— alkanediyl-, —NH— alkanediyl-NH—, or -alkanediyl-NH-alkanediyl-. When any of these terms is used with the "substituted" modifier one or more hydrogen atom has been independently replaced by —OH, —F, —Cl, —Br, —I, —NH$_2$, —NO$_2$, —CO$_2$H, —CO$_2$CH$_3$, —CN, —SH, —OCH$_3$, —OCH$_2$CH$_3$, —C(O)CH$_3$, —NHCH$_3$, —NHCH$_2$CH$_3$, —N(CH$_3$)$_2$, —C(O)NH$_2$, —OC(O)CH$_3$, or —S(O)$_2$NH$_2$. The groups —NHC(O)OCH$_3$ and —NHC(O)NHCH$_3$ are non-limiting examples of substituted amido groups.

The use of the word "a" or "an," when used in conjunction with the term "comprising" in the claims and/or the specification may mean "one," but it is also consistent with the meaning of "one or more," "at least one," and "one or more than one."

Throughout this application, the term "about" is used to indicate that a value includes the inherent variation of error for the device, the method being employed to determine the value, or the variation that exists among the study subjects.

The terms "comprise," "have" and "include" are open-ended linking verbs. Any forms or tenses of one or more of these verbs, such as "comprises," "comprising," "has," "having," "includes" and "including," are also open-ended. For example, any method that "comprises," "has" or "includes" one or more steps is not limited to possessing only those one or more steps and also covers other unlisted steps.

The term "effective," as that term is used in the specification and/or claims, means adequate to accomplish a desired, expected, or intended result. "Effective amount," "Therapeutically effective amount" or "pharmaceutically effective amount" when used in the context of treating a patient or subject with a compound means that amount of the compound which, when administered to a subject or patient for treating a disease, is sufficient to effect such treatment for the disease.

The term "hydrate" when used as a modifier to a compound means that the compound has less than one (e.g., hemihydrate), one (e.g., monohydrate), or more than one (e.g., dihydrate) water molecules associated with each compound molecule, such as in solid forms of the compound.

As used herein, the term "IC$_{50}$" refers to an inhibitory dose which is 50% of the maximum response obtained. This quantitative measure indicates how much of a particular drug or other substance (inhibitor) is needed to inhibit a given biological, biochemical or chemical process (or component of a process, i.e. an enzyme, cell, cell receptor or microorganism) by half.

An "isomer" of a first compound is a separate compound in which each molecule contains the same constituent atoms as the first compound, but where the configuration of those atoms in three dimensions differs.

As used herein, the term "patient" or "subject" refers to a living vertebrate organism, such as a human, monkey, cow, sheep, goat, dog, cat, mouse, rat, guinea pig, bird, fish or transgenic species thereof. In certain embodiments, the patient or subject is a primate. Non-limiting examples of human subjects are adults, juveniles, infants and fetuses.

As generally used herein, "pharmaceutically acceptable" refers to those compounds, materials, compositions, and/or dosage forms which are, within the scope of sound medical judgment, suitable for use in contact with the tissues, organs, and/or bodily fluids of human beings and animals without excessive toxicity, irritation, allergic response, or other problems or complications commensurate with a reasonable benefit/risk ratio.

"Pharmaceutically acceptable salts" means salts of compounds of the present invention which are pharmaceutically acceptable, as defined above, and which possess the desired pharmacological activity. Such salts include acid addition salts formed with inorganic acids such as hydrochloric acid, hydrobromic acid, sulfuric acid, nitric acid, phosphoric acid, and the like; or with organic acids such as 1,2-ethanedisulfonic acid, 2-hydroxyethanesulfonic acid, 2-naphthalenesulfonic acid, 3-phenylpropionic acid, 4,4'-methylenebis(3-hydroxy-2-ene-1-carboxylic acid), 4-methylbicyclo[2.2.2]oct-2-ene-1-carboxylic acid, acetic acid, aliphatic mono- and dicarboxylic acids, aliphatic sulfuric acids, aromatic sulfuric acids, benzenesulfonic acid, benzoic acid, camphorsulfonic acid, carbonic acid, cinnamic acid, citric acid, cyclopentanepropionic acid, ethanesulfonic acid, fumaric acid, glucoheptonic acid, gluconic acid, glutamic acid, glycolic acid, heptanoic acid, hexanoic acid, hydroxynaphthoic acid, lactic acid, laurylsulfuric acid, maleic acid, malic acid, malonic acid, mandelic acid, methanesulfonic acid, muconic acid, o-(4-hydroxybenzoyl)benzoic acid, oxalic acid, p-chlorobenzenesulfonic acid, phenyl-substituted alkanoic acids, propionic acid, p-toluenesulfonic acid, pyruvic acid, salicylic acid, stearic acid, succinic acid, tartaric acid, tertiary-butylacetic acid, trimethylacetic acid, and the like. Pharmaceutically acceptable salts also include base addition salts which may be formed when acidic protons present are capable of reacting with inorganic or organic bases. Acceptable inorganic bases include sodium hydroxide, sodium carbonate, potassium hydroxide, aluminum hydroxide and calcium hydroxide. Acceptable organic bases include ethanolamine, diethanolamine, triethanolamine, tromethamine, N-methylglucamine and the like. It should be recognized that the particular anion or cation forming a part of any salt of this invention is not critical, so long as the salt, as a whole, is pharmacologically acceptable. Additional examples of pharmaceutically acceptable salts and their methods of preparation and use are presented in *Handbook of Pharmaceutical Salts: Properties, and Use* (2002).

"Prevention" or "preventing" includes: (1) inhibiting the onset of a disease in a subject or patient which may be at risk and/or predisposed to the disease but does not yet experience or display any or all of the pathology or symptomatology of the disease, and/or (2) slowing the onset of the pathology or symptomatology of a disease in a subject or patient which may be at risk and/or predisposed to the disease but does not yet experience or display any or all of the pathology or symptomatology of the disease, including reactivation.

"Prodrug" means a compound that is convertible in vivo metabolically into an inhibitor according to the present invention. The prodrug itself may or may not also have activity with respect to a given target protein. For example, a compound comprising a hydroxy group may be administered as an ester that is converted by hydrolysis in vivo to the hydroxy compound. Suitable esters that may be converted in vivo into hydroxy compounds include acetates, citrates, lactates, phosphates, tartrates, malonates, oxalates, salicylates, propionates, succinates, fumarates, maleates, methylene-bis-β-hydroxynaphthoate, gentisates, isethionates, di-p-toluoyltartrates, methanesulfonates, ethanesulfonates, benzenesulfonates, p-toluenesulfonates, cyclohexylsulfamates, quinates, esters of amino acids, and the like. Similarly, a compound comprising an amine group may be administered as an amide that is converted by hydrolysis in vivo to the amine compound.

The term "saturated" when referring to an atom means that the atom is connected to other atoms only by means of single bonds.

A "stereoisomer" or "optical isomer" is an isomer of a given compound in which the same atoms are bonded to the same other atoms, but where the configuration of those atoms in three dimensions differs. "Enantiomers" are stereoisomers of a given compound that are mirror images of each other, like left and right hands. "Diastereomers" are stereoisomers of a given compound that are not enantiomers. Chiral molecules contain a chiral center, also referred to as a stereocenter or stereogenic center, which is any point, though not necessarily an atom, in a molecule bearing groups such that an interchanging of any two groups leads to a stereoisomer. In organic compounds, the chiral center is typically a carbon, phosphorus or sulfur atom, though it is also possible for other atoms to be stereocenters in organic and inorganic compounds. A molecule can have multiple stereocenters, giving it many stereoisomers. In compounds whose stereoisomerism is due to tetrahedral stereogenic centers (e.g., tetrahedral carbon), the total number of hypothetically possible stereoisomers will not exceed 2n, where n is the number of tetrahedral stereocenters. Molecules with symmetry frequently have fewer than the maximum possible number of stereoisomers. A 50:50 mixture of enantiomers is referred to as a racemic mixture. Alternatively, a mixture of enantiomers can be enantiomerically enriched so that one enantiomer is present in an amount greater than 50%. Typically, enantiomers and/or diastereomers can be resolved or separated using techniques known in the art. It is contemplated that for any stereocenter or axis of chirality for which stereochemistry has not been defined, that stereocenter or axis of chirality can be present in its R form, S form, or as a mixture of the R and S forms, including racemic and non-racemic mixtures. As used herein, the phrase "substantially free from other stereoisomers" means that the composition contains ≤15%, more preferably ≤10%, even more preferably ≤5%, or most preferably ≤1% of another stereoisomer(s).

"Effective amount," "therapeutically effective amount" or "pharmaceutically effective amount" means that amount which, when administered to a subject or patient for treating a disease, is sufficient to effect such treatment for the disease.

"Treatment" or "treating" includes (1) inhibiting a disease in a subject or patient experiencing or displaying the pathology or symptomatology of the disease (e.g., arresting further development of the pathology and/or symptomatology), (2) ameliorating a disease in a subject or patient that is experiencing or displaying the pathology or symptomatology of the disease (e.g., reversing the pathology and/or symptomatology), and/or (3) effecting any measurable decrease in a disease in a subject or patient that is experiencing or displaying the pathology or symptomatology of the disease. In some embodiments, treatment of a patient afflicted with one of the pathological conditions described herein comprises administering to such a patient an amount of compound described herein which is therapeutically effective in controlling the condition or in prolonging the survivability of the patient beyond that expected in the absence of such treatment. As used herein, the term "inhibition" of the condition also refers to slowing, interrupting, arresting or stopping the condition and does not necessarily indicate a total elimination of the condition. It is believed that prolonging the survivability of a patient, beyond being a significant advantageous effect in and of itself, also indicates that the condition is beneficially controlled to some extent.

The above definitions supersede any conflicting definition in any reference that is incorporated by reference herein. The fact that certain terms are defined, however, should not be considered as indicative that any term that is undefined is indefinite. Rather, all terms used are believed to describe the invention in terms such that one of ordinary skill can appreciate the scope and practice the present invention.

D. Therapeutic Methods

1. Pharmaceutical Formulations

In particular embodiments, where clinical application of an active ingredient is undertaken, it will be necessary to prepare a pharmaceutical composition appropriate for the intended application. Generally, this will entail preparing a pharmaceutical composition that is essentially free of pyrogens, as well as any other impurities or contaminants that could be harmful to humans or animals. One also will generally desire to employ appropriate buffers to render the complex stable and allow for uptake by target cells.

Aqueous compositions of the present invention comprise an effective amount of the active ingredient, as discussed above, further dispersed in pharmaceutically acceptable carrier or aqueous medium. Such compositions also are referred to as inocula. The phrases "pharmaceutically or pharmacologically acceptable" refer to compositions that do not produce an adverse, allergic or other untoward reaction when administered to an animal, or a human, as appropriate, as well as the requisite sterility for in vivo uses.

As used herein, "pharmaceutically acceptable carrier" includes any and all solvents, dispersion media, coatings, antibacterial and antifungal agents, isotonic and absorption delaying agents and the like. The use of such media and agents for pharmaceutically active substances is well known in the art. Except insofar as any conventional media or agent is incompatible with the active ingredient, its use in the therapeutic compositions is contemplated. Supplementary active ingredients also can be incorporated into the compositions.

Solutions of therapeutic compositions can be prepared in water suitably mixed with a surfactant, such as hydroxypropylcellulose. Dispersions also can be prepared in glycerol, liquid polyethylene glycols, mixtures thereof and in oils. Under ordinary conditions of storage and use, these preparations contain a preservative to prevent the growth of microorganisms.

The therapeutic compositions of the present invention are advantageously administered in the form of injectable compositions either as liquid solutions or suspensions; solid forms suitable for solution in, or suspension in, liquid prior to injection may also be prepared. These preparations also may be emulsified. A typical composition for such purpose comprises a pharmaceutically acceptable carrier. For instance, the composition may contain 10 mg, 25 mg, 50 mg or up to about 100 mg of human serum albumin per milliliter of phosphate buffered saline. Other pharmaceutically acceptable carriers include aqueous solutions, non-toxic excipients, including salts, preservatives, buffers and the like.

Examples of non-aqueous solvents are propylene glycol, polyethylene glycol, vegetable oil and injectable organic esters such as ethyloleate. Aqueous carriers include water, alcoholic/aqueous solutions, saline solutions, parenteral vehicles such as sodium chloride, Ringer's dextrose, etc. Intravenous vehicles include fluid and nutrient replenishers. Preservatives include antimicrobial agents, anti-oxidants, chelating agents and inert gases. The pH and exact concentration of the various components the pharmaceutical composition are adjusted according to well-known parameters.

Additional formulations are suitable for oral administration. Oral formulations include such typical excipients as, for example, pharmaceutical grades of mannitol, lactose, starch, magnesium stearate, sodium saccharine, cellulose, magnesium carbonate and the like. The compositions take the form of solutions, suspensions, tablets, pills, capsules, sustained release formulations or powders. When the route is topical, the form may be a cream, ointment, a controlled release patch, salve or spray.

An effective amount of the therapeutic composition is determined based on the intended goal. The term "unit dose" or "dosage" refers to physically discrete units suitable for use in a subject, each unit containing a predetermined quantity of the therapeutic composition calculated to produce the desired responses, discussed above, in association with its administration, i.e., the appropriate route and treatment regimen. The quantity to be administered, both according to number of treatments and unit dose, depends on the protection desired.

Precise amounts of the therapeutic composition also depend on the judgment of the practitioner and are peculiar to each individual. Factors affecting dose include physical and clinical state of the patient, the route of administration, the intended goal of treatment and the potency, stability and toxicity of the particular therapeutic substance.

2. Routes of Administration

Formulations of the present invention are suitable for oral administration. However, the therapeutic compositions of the present invention may be administered via any common route so long as the target tissue is available via that route. This includes nasal, buccal, corneal, rectal, vaginal, or topical administration, and intradermal, subcutaneous, intramuscular, intraperitoneal or intravenous injection. As such, compositions would be formulated pharmaceutically in route-acceptable compositions that include physiologically acceptable carriers, buffers or other excipients.

As with dosing amounts, the timing of delivery (including intervals and total number of doses) depends on the judgment of the practitioner and are peculiar to each individual. Factors affecting dose include physical and clinical state of the patient, the route of administration, the intended goal of treatment and the potency, stability and toxicity of the particular therapeutic substance.

3. Combination Therapy

In many clinical situations, it is advisable to use a combination of distinct therapies. Thus, it is envisioned that, in addition to the therapies described above, one would also wish to provide to the patient more "traditional" pharmaceutical herpesvirus therapies. Examples of standard therapies are described above. Combinations may be achieved by administering a single composition or pharmacological formulation that includes both agents, or with two distinct compositions or formulations, at the same time, wherein one composition includes the agents of the present invention and the other includes the standard therapy. Alternatively, standard therapy may precede or follow the present agent treatment by intervals ranging from minutes to weeks to months. In embodiments where the treatments are applied separately, one would generally ensure that a significant period of time did not expire between the time of each delivery, such that the agents would still be able to exert an advantageously combined effect on the subject. In such instances, it is contemplated that one would administer both modalities within about 12-24 hours of each other and, more preferably, within about 6-12 hours of each other, with a delay time of only about 12 hours being most preferred. In some situations, it may be desirable to extend the time period for treatment significantly, however, where several days (2, 3, 4, 5, 6 or 7) to several weeks (1, 2, 3, 4, 5, 6, 7 or 8) lapse between the respective administrations.

It also is conceivable that more than one administration of either the agent of the present disclosure, or the standard therapy will be desired. Various combinations may be employed, where the present invention compound is "A" and the standard therapy is "B", as exemplified below:

A/B/A B/A/B B/B/A A/A/B B/A/A A/B/B B/B/B/A

B/B/A/B A/A/B/B A/B/A/B A/B/B/A B/B/A/A B/A/B/A

B/A/A/B B/B/B/A A/A/A/B B/A/A/A A/B/A/A A/A/B/A

A/B/B/B B/A/B/B B/B/A/B

Other combinations are contemplated as well. Drugs suitable for such combinations are described above and include, but are not limited to, herpesvirus DNA polymerase inhibitors (nucleoside analogs), including acyclovir, famciclovir, valaciclovir, penciclovir, and ganciclovir.

E. Examples

The following examples are included to further illustrate various aspects of the invention. It should be appreciated by those of skill in the art that the techniques disclosed in the examples which follow represent techniques and/or compositions discovered by the inventors to function well in the practice of the invention, and thus can be considered to constitute preferred modes for its practice. However, those of skill in the art should, in light of the present disclosure, appreciate that many changes can be made in the specific embodiments which are disclosed and still obtain a like or similar result without departing from the spirit and scope of the invention.

1. Materials and Methods

Possible Targets for Nucleotidyl Transferase Superfamily Inhibitors in the Herpesvirus Genomes. The inhibitors screened here function against HIV by binding to the viral RNase H or integrase active sites and chelating the essential divalent cations within the active site (Fuji et al., 2009; Su et al., 2010; Chung et al., 2011; Billamboz et al., 2011; Himmel et al., 2009; Kirschberg et al., 2009). Therefore, their presumed mechanism of action is to inhibit one or more of the viral and/or cellular NTS enzymes essential for herpesviral genomic replication. This mechanism has not yet been tested.

For the herpes simplex viruses, candidate genes include the RNase H activity of the pUL30 DNA polymerase (Liu et al., 2006), the 3'-5' exonuclease activity of pUL30 (Coen 1996), the strand transfer activity of ICP8 (Bortner et al., 1993; Nimonkar & Boehmer, 2003), or the 5'-3' exonuclease activity of the pUL12 polymerase accessory protein (Schumacher et al., 2012) that are directly involved in virus replication (Weller & Coen 2012). The pUL15 terminase protein that cleaves the concatameric viral DNA produced by DNA replication into the mature linear monomers is also a prime candidate (Selvarajan et al., 2013).

HCMV encodes proteins with functions consistent with NTS enzymes that could be plausible targets. pUL98 is the HCMV ortholog of HSV pUL12 and is functionally conserved, as demonstrated by trans-complementation experiments (Gao et al., 1998). At least two of the seven HCMV proteins involved in encapsidation form an essential terminase complex which likely functions as both an endonuclease and a DNA translocase during DNA cleavage and packaging (Bogner, 2002; Hwang & Bogner, 2002; Scheffczik et al., 2002; Scholz et al., 2003). These genes are conserved throughout the herpesvirus family (Alba et al., 2001) and deletion of any of the seven results in accumulation of empty capsids in the nucleus. The human cytomegalovirus (HCMV) terminase subunits pUL56 and pUL89, encoded by the UL56 and UL89 genes, have been extensively studied. Both gene products form toroidal structures, bind DNA, and have nuclease activity (Bogner et al., 1998; Scheffczik et al., 2002). While pUL56 mediates the specific binding to pac sequences on DNA concatamers and provides energy and structural assistance for DNA translocation into the procapsids, pUL89 cleaves the DNA concatomers (Bogner, 2002). These are the orthologs of HSV terminase subunits pUL15 and pUL28.

Cellular proteins are also plausible targets for the action of the NTS inhibitors, especially because DNA recombination events appear to be important during productive replication (Weller & Coen 2012). These proteins include the human RNase H1 that could assist in removal of RNA primers for DNA synthesis, but this is not a leading candidate because the compound β-thujaplicinol (#46, Table 1 and 2) profoundly inhibits HSV-1 and HSV-2 replication but the inventors have shown that it has no effect on RNase H1 (Hu et al., 2013). Other candidates include the Fen1 endonuclease that may assist in removal of primers (Zhu et al., 2010), and the double-stranded break repair enzymes Mre11, Rad50, NBS1, Rad51 (Weizman & Weller 2011), and Rad52 (Schumacher et al., 2012). The base-excision repair enzymes SSH2 and MLH1 which form complexes that are recruited to viral replication sites and contribute to HSV genomic replication (Mohni et al., 2011) are also plausible targets.

Figure 6:
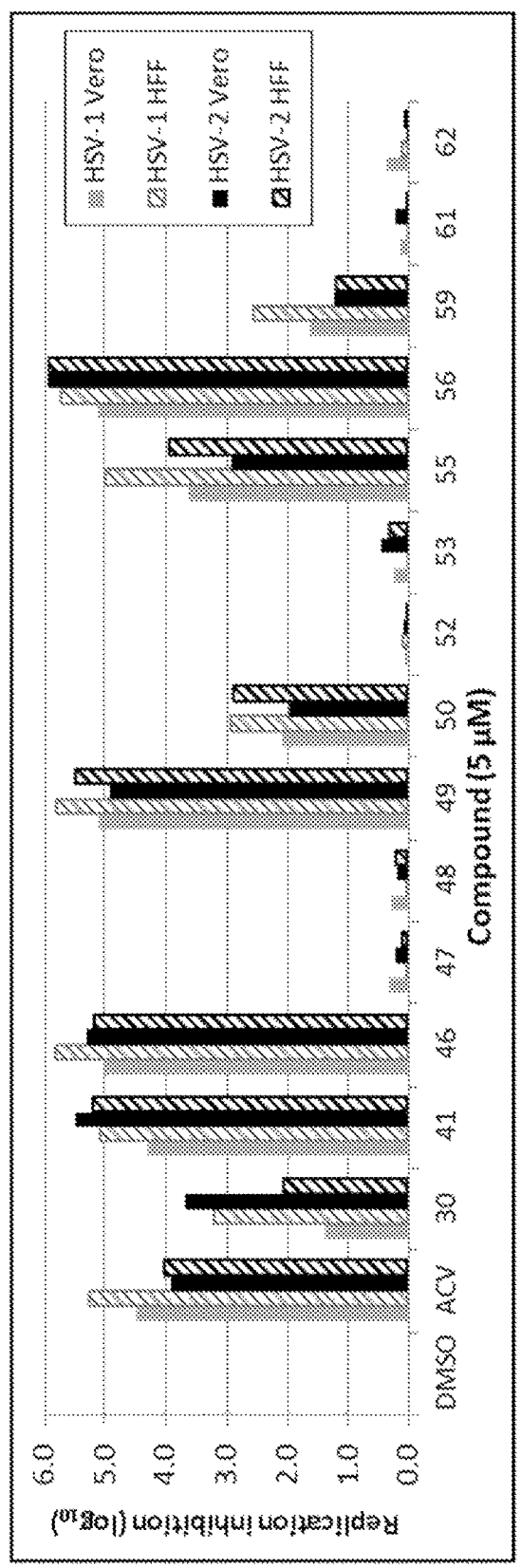
FIG. 6. Inhibition of HSV-1 and HSV-2 replication in human foreskin fibroblasts at 5 µM. Compounds were added to primary human foreskin fibroblast (HFF) cells simultaneously with HSV-1 or HSV-2 infection at moi of 0.1 and infectious virus titers in the cultures at 24 hours post-infection were determined by plaque assay on Vero cells as in FIG. 1. The data for the HFF infections are plotted next to the analogous data from Vero cells derived from FIG. 1 for comparison. Data are the averages from two experiments per compound, each done in duplicate.

Cells and Viruses. Vero cells were maintained in Dulbecco's modified Eagle's medium (DMEM) containing 3% newborn calf serum, 3% bovine growth serum, 2 mM L-glutamine and 100 IU/mL penicillin and 0.1 mg/mL streptomycin (P/S). Primary human foreskin fibroblasts (ATCC #CRL2429™) were cultured in DMEM containing 10% FBS, 2 mM L-glutamine plus P/S, and used at passage 3 to 12. HSV-1 #6 and HSV-2 #1 are de-identified clinical isolates from the Saint Louis University Hospital. Stocks were prepared after a single passage in cell culture and were titered by standard plaque assay (Knipe and Spang, 1982). Wild-type HSV-1 and HSV-2 used in FIG. 6 were laboratory strains 17 and 333, respectively. The HSV-1 TK-deficient mutant, ΔTK contains a 361-bp deletion between the BglII-SmaI restriction enzyme sites in the UL23 open reading frame of strain 17 (Korom, et al., 2013). The TK-deficient mutant of HSV-2 strain 333, ΔTK-, contains a 180-bp KpnI-KpnI deletion in the UL23 open reading frame that abrogates TK activity (McDermott, et al, 1984). ΔTK- was the generous gift of Jim Smiley. Virus stocks were grown and titered on Vero cells (Morrison and Knipe, 1996).

Compound Selection Strategy. Compounds were selected for evaluation of their ability to inhibit HSV replication based on one or more of the following criteria:
  ability to inhibit the HIV RNase H as determined by literature searches
  ability to inhibit the HIV integrase as determined by literature searches
  ability to inhibit the HBV RNase H as determined by data
  close chemical relatives of compounds that inhibit the HIV RNase H, the HIV integrase, or the HBV RNase H
  availability from commercial sources and/or through the NCI compound repository. Among the 170 potential compounds in the inventors' possession, 68 that met these criteria were chosen to maximize the chemical diversity assessed and to evaluate multiple compounds within seven chemical families: tropolones; polyoxygenated heterocycles (ciclopirox derivatives); HIV strand transfer inhibitors; cyanopyrans; aminocyanothiophenes; napthyridinones; and hydroxyxanthenones. Their structures are shown in FIG. 1 and are indicated by both the inventors' lab's arbitrary compound number (numbers between 1 and 173) and by either their common name, their NSC number, or the catalog number of the vendor from which they were acquired.

Anti-HSV-1 and -HSV-2 Replication Assay. Compounds to be screened were diluted in PBS supplemented to contain 2% newborn calf serum and 1% glutamine, and added in 100 µL, volume to confluent cell monolayers in 24-well cluster plates. Immediately thereafter HSV-1 and HSV-2, diluted in the supplemented PBS medium, were added to the wells in 50 µl volume such that the final concentration of compound was 50 µM and 5 µM and the multiplicity of infection was 0.1. The plates were incubated at 37° C. for 1 hour and then virus-containing inoculum was removed and the wells were washed once in PBS. Compounds, diluted to 50 µM and 5 µM in DMEM supplemented to contain 2% newborn calf serum and 1% each penicillin/streptomycin, were added at 0.5 mL/well. Plates were incubated at 37° C. an additional 23 hr, and then the plates were visually inspected through a phase contrast microscope for cytopathic effect, and for toxic effect. Only those wells in which the cell monolayer was substantially healthier than the DMSO-treated control wells were harvested, and also a sampling of additional wells which showed cytopathic effect. The entire contents of each well were collected by scraping. Samples were frozen at −80° C., and then subsequently thawed, sonicated, and infectious virus titer was determined by standard plaque assay on Vero cell monolayers. Because the compounds were dissolved at 10 mM in 100% DMSO, equivalent dilutions of DMSO were added to additional wells as a control for effects of the diluent. Each experiment was repeated once. $EC_{50}$ values were determined as above except that serial dilutions of the compound to be tested were prepared starting at 50 µM. The inhibitory values were calculated by non-linear curve-fitting in GraphPad Prism.

Toxicity Assays. Qualitative assessments of cytotoxicity were done visually by inspecting the cells in the primary screening assays. For the quantitative assays, cells were plated in 96-well plates at $1.0 \times 10^4$ per well. The next day the compounds were added at 0.78 to 100 µM in a final concentration of 1% (v/v) DMSO, and the cells were incubated for 24 hours under conditions identical to those employed for the viral replication inhibition assays. Mitochondrial toxicity was measured by incubating the cells with 0.25 mg/mL thiazolyl blue tetrazolium bromide (MTT, SigmaAldrich Chemical Co.), the cultures were incubated for 60 min, metabolites were solubilized in acidic isopropanol, and absorbance was read at 570 nm. Cellular lysis was measured by detecting release of intracellular proteases with the CytoTox-Glo assay (Promega) according to the manufacturer's instructions. Percent viability was determined for each compound concentration from the maximal absorbance or luminosity data, and then $CC_{50}$ values were calculated by non-linear curve fitting using GraphPad Prism.

Quantitative PCR measurement of viral genome levels. Infected cell cultures were collected and virus and cells were pelleted by centrifugation for 30 min at 12,000 rpm. Total DNA was isolated from the pellets using a QIAamp DNA Mini Kit (Qiagen) according to the manufacturer's instructions. DNA concentration of each preparation was measured using a Nanodrop 2000 spectrophotometer. The primers and probe for real-time PCR were designed to amplify a 108 bp segment in the HSV-2 LAT region. The sequences of the primers and probe were: forward 5'-GAGCTAACACTCG-GCTTGCT-3' (SEQ ID NO: 1); reverse 5'-TCTCCTC-CCCGTCTTTCC-3' (SEQ ID NO: 2); and Universal Probe Library probe #10 5'-FAM-GGAGGTG-dark quencher-3' (Roche). PCR reactions were set up in 25 µL containing FastStart Universal Probe master mix containing Rox (Roche), 900 nM forward and reverse primers, 250 nM probe, and 5 µL template DNA preparation (~30-100 ng total DNA). Quantification was performed in triplicate for each DNA preparation using an ABI model 7500 genetic analyzer (Applied Biosystems) with the following cycling parameters: 1 cycle at 50° C. for 2 min, 1 cycle at 95° C. for 10 min, 40 cycles at 95° C. for 15 s, and 60° C. for 1 min. For absolute quantification, $10^3$ to $10^8$ copies of plasmid pcDNA3.1(+)5'Flag-ICP0 was used to generate a standard curve. Data were analyzed using Sequence Detection System software (ABI), and HSV-2 genome equivalents number per nanogram of total DNA was calculated and used for comparison.

Biochemical inhibition of HBV RNaseH and human RNaseH1 activity. Compounds were tested for activity against the HBV RNaseH and human RNaseH1 in vitro as previously described (Tavis, et al., 2013; Hu, et al., 2013) Briefly, recombinant hexahistidine-tagged enzymes were expressed in *E. coli* and partially purified by nickel affinity chromatography. RNaseH activity was measured using an oligonucleotide-directed RNA cleavage assay in which a DNA oligonucleotide is annealed to an internally $^{32}$P-labeled RNA, the RNA:DNA heteroduplex is incubated with the enzyme to permit cleavage, and then the RNA cleavage products are resolved by electrophoresis and detected by autoradiography. The compounds were included in the reaction mixes at 60, 20, or 10 µM and the amount of the RNA cleavage products in the compound-containing reactions was compared to reactions in which an equivalent concentration of DMSO was added as a vehicle control. The data were quantified using ImageJ.

Resistance evolution against NTS inhibitors ciclopirox (#41) and β-thujaplicinol (#46) develops more slowly than against ACV. Replicate Vero cell monolayers were infected at a multiplicity of infection (moi) of 0.1 or 0.01 with HSV-1 strain KOS in the presence of suboptimal concentrations of ACV, #41 or #46 (0.75× to 10×$EC_{50}$). Cultures were scraped and collected when virus-induced cytopathic effect was evident (24-72 h). Virus titer in each independent lineage was determined by standard plaque assay, and then another round of selection was initiated for each lineage at moi of 0.1 or 0.01 in the presence of suboptimal concentrations of the inhibitors. This process was repeated three times, maintaining the independent lineages. Virus lineages collected after the third round of selection were titered and then used to infect fresh Vero cell monolayers at moi of 0.1 in the presence of diluent control or inhibitor (10× the $EC_{50}$ of ACV, 6× the $EC_{50}$ of #41, or 1.5× the $EC_{50}$ of #46). Additional monolayers were infected with HSV-1 KOS at moi of 0.1 in the presence of diluent control or inhibitors as a control non-passaged virus lineage. Cultures were collected after 24 h (ACV and #41), or 42 h (#46) and titer was determined by plaque assay. Inhibition was determined by subtracting a lineage's titer in the presence of inhibitor from its titer in the presence of diluent control.

Anti-HCMV CPE inhibition and cytotoxicity assays. HFFs were infected with HCMV strain AD169 in the presence of serial dilutions of the compounds from 0.0192 to 60 µM. Fourteen days later the monolayers were stained with crystal violet, and retained cell density was quantified using a multiplate autoreader (BioTek). Cytotoxicity was measured the same way, except that the cells were uninfected and neutral red internalization by viable cells was measured.

HCMV plaque reduction $EC_{50}$ and toxicity assays. Low passage primary HFFs were infected with HCMV strain AD169 in the presence of serial dilutions of the compounds from 0.032 to 100 µM. Ten days later the monolayers were stained with 1% neutral red solution in PBS. After rinsing, plaques were counted using a stereomicroscope and the $EC_{50}$ was interpolated from the data. Cytotoxicity was measured using a plate-based assay in which compounds were added to HFFs at 0.032 to 100 µM. At the end of the incubation period, plates were stained for 1 h with a neutral red solution in PBS. The stain was then removed, the plates rinsed in PBS and dried, and dye internalized by viable cells was determined at $OD_{550}$. $CC_{50}$ values were interpolated from the data.

The non-clinical and preclinical services program offered by the National Institute of Allergy and Infectious Diseases was utilized in performance of these HCMV assays.

Single dose pharmacokinetic study after peroral treatment with ciclopirox Olamine. Six week old BALB/c mice were treated with 100 mg/kg ciclopirox olamine by oral gavage. This is well below the oral toxicity level in mice of 1740 mg/kg (Spectrum Chemicals MSDS). At 15 min, 30 min, 1 h, 3 h and 5 h post-treatment, blood was collected from pairs of mice and the serum separated. Mice were then euthanized and trigeminal ganglia (TG), brainstems and corneas were dissected and frozen until tissue extraction was performed and the extracts analyzed by mass spectroscopy. Standardization to ciclopirox olamine was achieved using compound spiked into a matrix of relevant tissue homogenate from untreated mice.

Treatment of HSV-1-infected mice with compounds #41-E and #46. 129 mice were infected with $1\times10^5$ pfu/eye of HSV-1 on the scarified corneas and then were treated once daily with acyclovir (ACV; 2 mice) or compound #46 (2 mice) by dropwise application to the corneal surface. Compounds were administered at 1 µg/eye in 10% DMSO. Two mice were treated with 10% DMSO as a negative control. The corneal surface was swabbed once per day on days 1, 2, 4 and 5 post-infection and titer of virus shed from the epithelium was determined by standard plaque assay. On the fifth day post-infection mice were euthanized and the trigeminal ganglia (TG) and brainstems were dissected. The tissues were disrupted and virus in them quantified by plaque assay. Alternatively, 129 mice were infected with HSV-1 on the scarified corneas and then were treated thrice daily with ACV or compound #46 as above. Weight of individual mice was recorded daily. In a third experiment, BALB/c mice were infected on the scarified corneas with $2 \times 10^4$ pfu/eye of HSV-1 and treated thrice daily with ACV (2 mice) or ciclopirox olamine (#41-E; 2 mice) at 7.5 µg/eye in normal saline. Saline was a negative control. On the fifth day post-infection mice were euthanized and the trigeminal ganglia (TG) and brainstems were dissected. The tissues were disrupted and virus in them quantified by plaque assay.

2. Results

Primary screening for inhibition of HSV-1 and HSV-2 replication. The efficacy of the 42 compounds plus ACV and cidofovir as example nucleos(t)ide analogs was tested against replication of primary clinical isolates of both HSV-1 and HSV-2. These compounds were initially assessed at 50 and 5 µM in a semi-quantitative replication inhibition assay in which Vero cell monolayers treated with compound or a DMSO vehicle control were infected at multiplicity of infection (moi) of 0.1. Monolayers were microscopically inspected 24 hours post-infection and wells in which more cells were visually healthier than the DMSO-treated controls were collected. Viral titers in the culture lysates were then determined by standard plaque assay on Vero cells. Inhibition of viral replication was categorized as <1 $\log_{10}$ relative to the DMSO-treated control, 1 to 3 $\log_{10}$ suppression, or ≥3 $\log_{10}$ suppression. Negligible inhibition at 50 µM was found for 24 of the compounds (57%) against HSV-1 and 23 of the compounds (55%) against HSV-2 (Table 1). Inhibition was negligible at 5 µM for 34 of the compounds (81%) against both HSV-1 and HSV-2 (Table 1 and FIG. 1). 1 to 3 $\log_{10}$ inhibition at 50 µM was observed for eight compounds (19%) against HSV-1 and seven compounds (17%) against HSV-2, and at 5 µM for three compounds (7%) each against HSV-1 and HSV-2. ≥3 $\log_{10}$ inhibition at 50 µM was observed for 10 compounds (24%) against HSV-1 and 12 compounds (29%) against HSV-2. Importantly, five compounds (#41, 46, 49, 55, and 56) remained inhibitors of HSV-1 and five (#30, 41, 46, 49, and 56) remained inhibitors of HSV-2 with ≥3 $\log_{10}$ inhibition at 5 µM (Table 1 and FIG. 1). The most powerful antagonist of both HSV-1 and HSV-2 replication at 5 µM was compound #56 (manicol), which inhibited HSV-1 by 5.14 $\log_{10}$ (138,000-fold) and HSV-2 by 5.95 $\log_{10}$ (891,000-fold). For comparison, the approved anti-HSV drug ACV inhibited HSV-1 replication at 5 µM in this assay by 4.49 $\log_{10}$ (30,900-fold) and HSV-2 by 3.91 $\log_{10}$ (8,130-fold), and inhibition by cidofovir was negligible. The distribution of the compounds based upon inhibition level is summarized in Table 3. Therefore, this primary screen of only 42 compounds led to identification of six compounds (#30, 41, 46, 49, 55, and 56) with comparable or better inhibitory activity than ACV against HSV-1 and/or HSV-2. An additional tropolone (#63) was screened for the capacity to inhibit HSV-1 and HSV-2 replication but initial testing showed the compound exhibited negligible inhibition. Additionally, four polyoxygenated heterocycle compounds were tested (#128, 138, 139, 140). None of these compounds was particularly efficacious at inhibiting HSV-1 and HSV-2 replication. Of nine napthyridinone compounds screened, one (#155) suppressed HSV-1 and HSV-2 replication by >3.84 $\log_{10}$ at 5 µM, and another (#151) suppressed HSV-1 and HSV-2 replication by >2.15 $\log_{10}$. Both compounds exhibited significant cytotoxicity at 50 µM. These compounds represent a fourth chemical class containing compounds that inhibit HSV replication. Finally, three Raltegravir derivatives (#72, 121, 122) and Dolutegravir (#73); four dioxobutanoic acids (#40, 129, 130, 131); two thienopyrimidones (#136, 137); and two hydroxychromenones (#134, 135) were screened, but these compounds exhibited negligible inhibition of HSV-1 or HSV-2 replication.

Studies were carried out to determine if inhibition of viral replication could be overcome by infecting the cells at a higher moi than was used in the primary screening assays. Vero cell monolayers were infected with HSV-1 and HSV-2 at moi 5 or the standard 0.1, the cells were treated with ACV, #46, or #55 at 50 or 5 µM, and viral yields at 24 hours post-infection were measured by plaque assay. ACV, #46 and #55 at 5 µM all efficiently controlled virus replication even after high moi infection; 50-fold more input virus yielded only 50-fold higher titers at 24 hr.

Overall, the compounds had similar levels of activity against HSV-1 and HSV-2 in Vero cells (Table 1 and FIG. 2). The only prominent exception was compound #30, which was >100-fold more active against HSV-2 than HSV-1 at 5 µM. This shared inhibitory pattern against the herpes simplex viruses was significantly different from the capacity of the same compounds to inhibit the HBV RNaseH or the human RNaseH1 (Table 1).

Compound Cytotoxicity. Compound cytotoxicity was measured both subjectively and quantitatively. Subjective assessments were done by visually inspecting the infected cells at the end of the 24 hours infection window through a phase-contrast microscope. Only those wells in which the cell monolayer had substantially less cytopathic effect (CPE) than the DMSO-treated control wells, and in which the uninfected cells had a normal appearance were harvested for titering of HSV levels. This indicates that all compounds for which the inventors obtained numerical viral replication data appeared much less toxic than uninhibited HSV replication under these conditions.

Quantitative toxicity measurements were conducted for all compounds that suppressed HSV replication by approximately 2 $\log_{in}$ or more at 5 µM plus a number of compounds with lesser inhibitory activity for comparison. Toxicity was assessed by measuring release of intracellular proteases into the culture medium due to cellular lysis. Cells were plated in 96-well plates at $1.0 \times 10^4$ per well. The next day compound was added in concentrations ranging from 0.78 to 100 µM in a final concentration of 1% (v/v) DMSO. The cells were incubated for 24 hours under conditions identical to those employed for the viral replication inhibition assays, and then release of intracellular proteases was measured with the CytoTox-Glo assay (Promega) according to the manufacturer's instructions. Percent viability was determined for each compound concentration from the luminosity data, and then $CC_{50}$ values were calculated by non-linear curve fitting using GraphPad Prism. Consistent with the subjective assessments of toxicity, all compounds selected for quantitative toxicity assessment had $CC_{50}$ values ≥50 µM by both the MTT and cellular lysis assays (Table 1).

Figure 3:
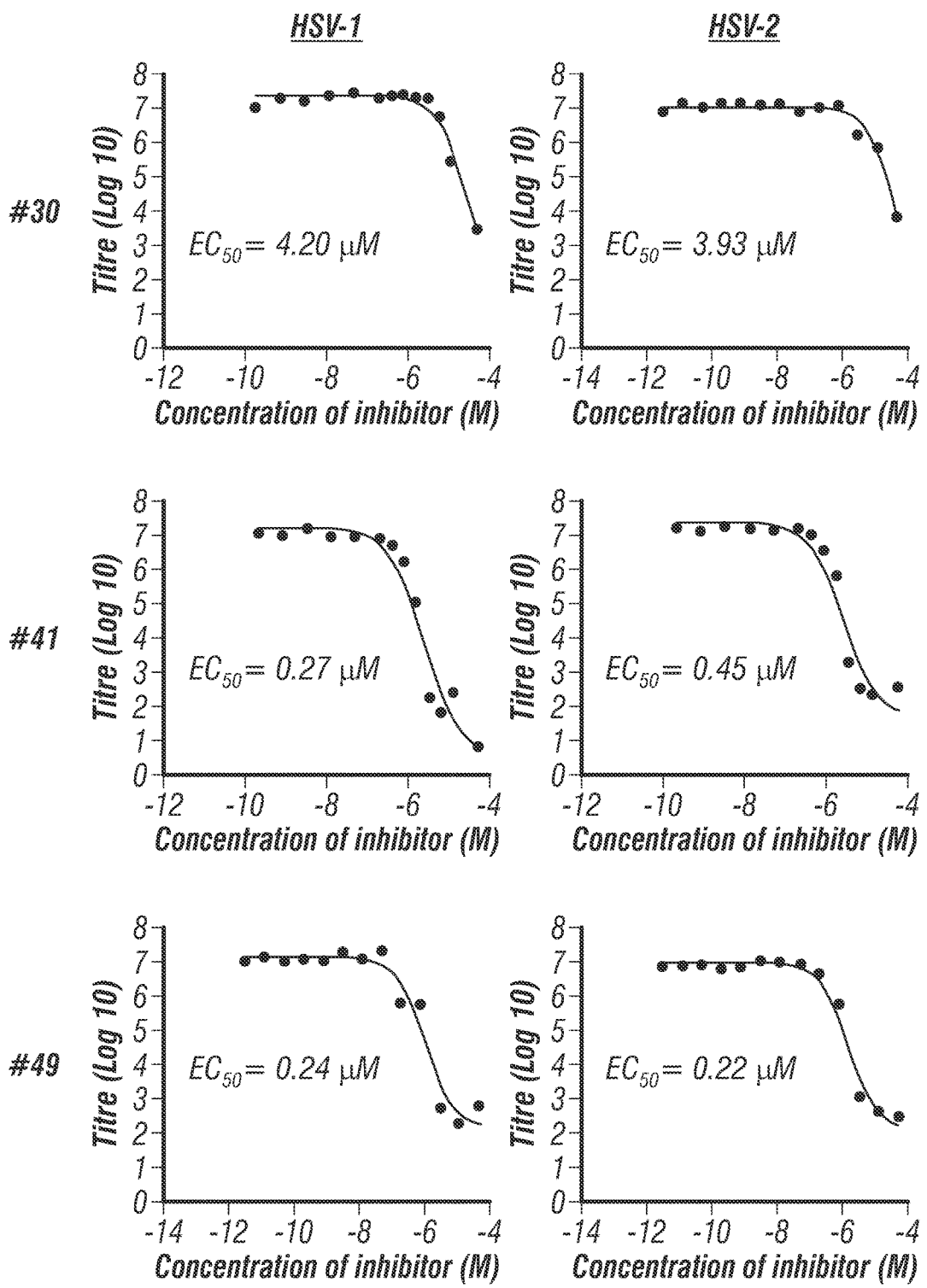
FIG. 3. $EC_{50}$ values for select herpesvirus inhibitors. Serially diluted compounds were added to Vero cells simultaneously with HSV-1 or HSV-2 infection at moi of 0.1, and infectious virus titers in the cultures at 24 hours post-infection were determined by plaque assay. Effective concentration 50 ($EC_{50}$) values were determined by non-linear curve-fitting. The curves are for representative experiments and the $EC_{50}$ values are the averages from two or three independent experiments per compound, each done in duplicate. The approved anti-herpes virus drug, ACV, was included for comparison purposes.
Figure 3:
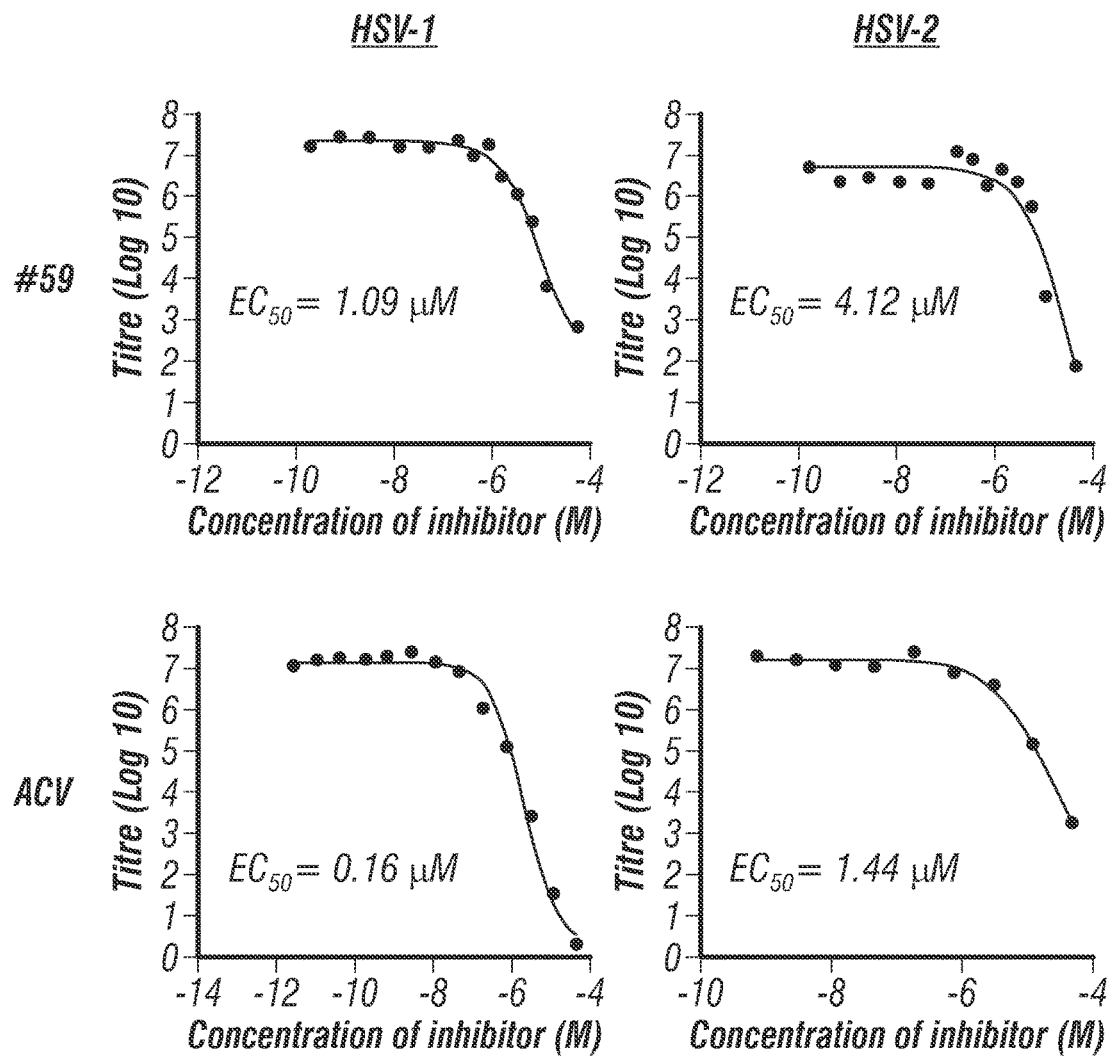
Figure 3:
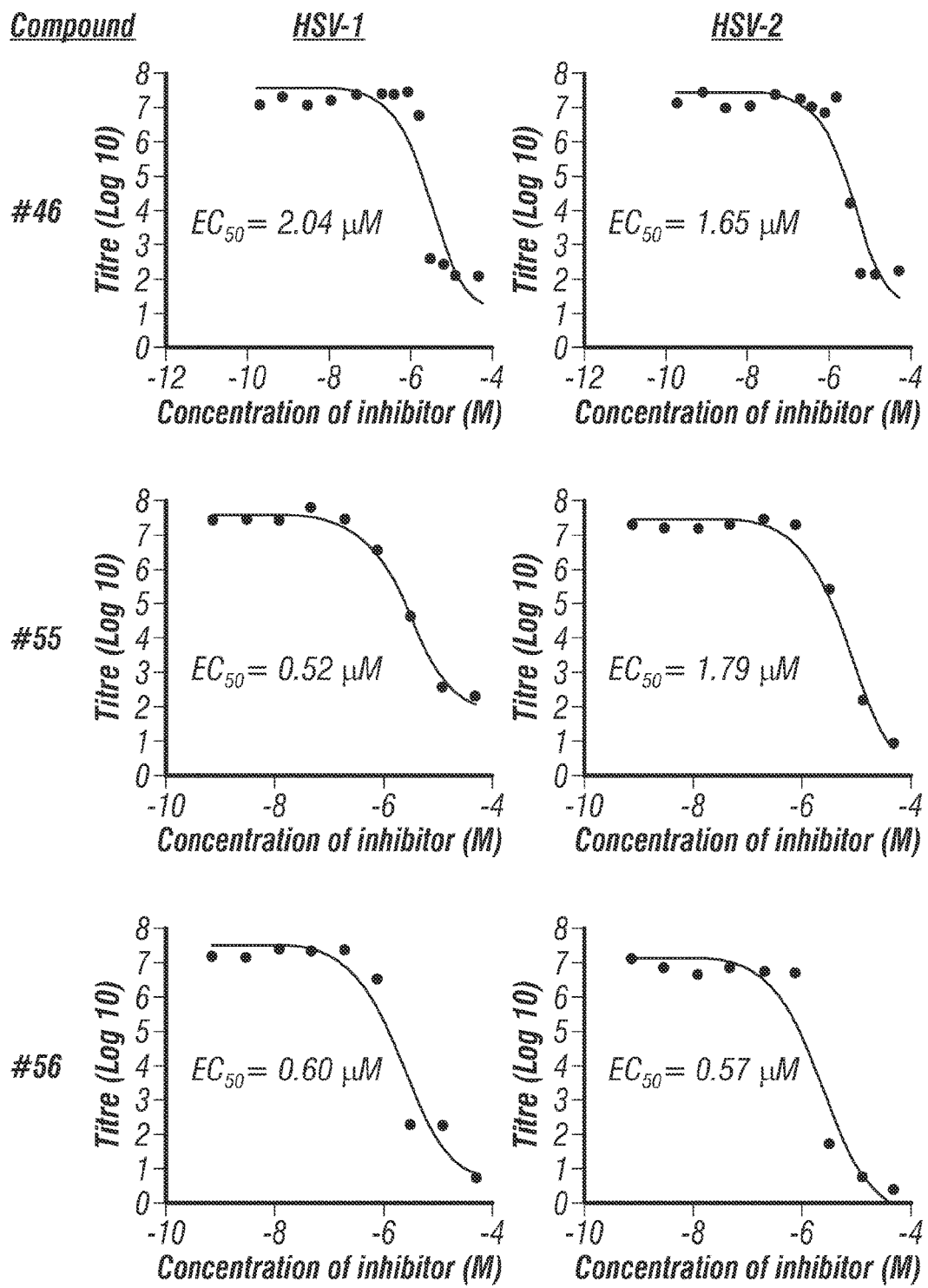

Quantitative HSV-1 and HSV-2 replication inhibition assays. To obtain a more quantitative evaluation of the inhibitory potential of the most promising compounds, $EC_{50}$ values were determined against HSV-1 and HSV-2 for all compounds with a greater than or equal to 3.0 log 10 inhibition at 5 µM (FIG. 3 and Table 4). Compound #59, which showed greater than or equal to 3.0 log 10 inhibition at 50 µM and inhibition between 1.0 and 3.0 log 10 at 5 µM, was also included. For HSV-1, $EC_{50}$ values ranged from 5.93 µM for compound #30 down to 0.27 µM for #41. For HSV-2, the values ranged from 4.58 µM for compound #59 to 0.19 µM for #49. For comparison, acyclovir had an $EC_{50}$ of 0.21 and 1.44 µM versus HSV-1 and HSV-2, respectively. Overall, these quantitative data confirmed the highly effective inhibition of HSV-1 and HSV-2 by these novel compounds in the semi-quantitative assay. They also reinforce the observation that these compounds can efficiently inhibit both HSV-1 and HSV-2, and they strengthen the conclusion that the strongest inhibitors identified here have similar or superior activity against the herpes simplex viruses than the approved drug acyclovir.

Preliminary SAR relationships within related chemical families. As an initial effort to determine whether sets of related compounds had interpretable inhibition patterns against HSV-1 and HSV-2, multiple compounds were assessed for six chemical families (Tropolones; Ciclopirox derivatives; HIV strand transfer inhibitors; Cyanopyrans; Aminocyanothiophenes; and Hydroxyxanthenones). Clear patterns were observable in the inhibition data when the compounds were sorted by their chemical classes (FIG. 2). At 5 µM, four of the 12 tropolones were inhibitor of both HSV-1 and HSV-2, which showed inhibition greater than or equal to 3.0 log 10, and a fifth showed inhibition between 1.0 and 3.0 log 10. Two additional chemical families had single inhibitors each: Compound #41 in the Ciclopirox class was a strong inhibitor of both HSV-1 and HSV-2, and #30 in the Hydroxyxanthenone class showed between 1.0 and 3.0 log 10 inhibition of HSV-1 and greater than or equal to 3.0 log 10 inhibition of HSV-2. These data indicate that compounds of multiple distinct chemical classes can inhibit both HSV-1 and HSV-2.

Sufficient data exist for the tropolone family to establish a preliminary SAR. Comparing compound #46 with compounds #47, #48, #50, and #53 indicates that efficient inhibition in the absence of extended R groups at the $\alpha$, $\beta$, or $\gamma$ positions of the tropolone ring requires three adjacent cation chelating moieties (the contiguous hydroxyl and carbonyl groups). Of the six compounds with larger R groups (#49, #52, #55, #56, #59 and #62), four were inhibitors (#49, #55, #56, and #59) which showed greater than or equal to 3.0 log 10 inhibition. Three of these four compounds (#49, #55, and #59) had only two metal chelating moieties on the tropolone ring, but the fourth compound (#56) had three metal-chelating moieties and was the strongest inhibitor the inventors have identified to date. The two larger compounds that were negligible inhibitors each had a side chain extending from the oxygen adjacent to the carbonyl on the tropolone ring which could interfere with metal ion chelation. These data imply that a carbonyl and a modified hydroxyl group are insufficient to support robust inhibition, and that three chelating moieties on the tropolone ring are superior to two. Finally, the four inhibitors (#49, #55, #56, and #59), which showed greater than or equal to 3.0 log 10 inhibition, had a variety of R groups opposite the metal-chelating motif, indicating that significant structural diversity is permitted in these elements. The wide range of $EC_{50}$ values for these four inhibitors (0.29 to 1.09 µM for HSV-1 and 0.22 to 4.12 µM for HSV-2) implies that the chemical elements opposite the chelating moieties can have a significant impact on the efficacy of the compounds.

Inhibition of HSV-1 and HSV-2 replication in human foreskin fibroblasts. Inhibition of viral replication was next assessed in human foreskin fibroblasts (HFF) to determine whether NTS inhibitors could block HSV-1 and HSV-2 replication in a physiologically relevant, primary human cell type. HFF cells were infected with HSV-1 or HSV-2 at moi 0.1 and treated with ACV or NTS inhibitors at 50 or 5 µM, or with a DMSO vehicle control. Viral yields 24 hours post-infection were measured by plaque assay. Fourteen compounds were selected for analysis, eight that were inhibitors of HSV-1 and HSV-2 at 5 µM in Vero cells (#30, 41, 46, 49, 50, 55, 56, and 59), which showed greater than 1.0 log 10 inhibition, and six that were negligible inhibitors in Vero cells (#47, 48, 52, 53, 61, and 62). As expected, ACV inhibited HSV-1 and HSV-2 with similar efficacy in Vero and HFF cells (Table 4 and FIG. 6). The eight compounds that inhibited HSV-1 and HSV-2 in Vero cells inhibited the viruses to similar or greater degrees in HFF cells, with the exception of compound #30 which inhibited HSV-2 ~45-fold less effectively in HFF cells at 5 µM. The six inhibitors in Vero cells remained unable to suppress HSV replication in HFFs. $CC_{50}$ values by the MTT assay in the HFF cells were >100 µM, with the exception of compounds #50 and 61 (Table 2). Therefore, NTS inhibitors can suppress HSV-1 and HSV-2 replication in a natural human host cell.

$EC_{50}$ determinations against HSV-1 and HSV-2. To more quantitatively assess the inhibitory potential of the most promising compounds, $EC_{50}$ values were determined in Vero cells for all compounds that were inhibitors of HSV-1 or HSV-2 at 5 µM (FIG. 3 and Table 1) at level greater than or equal to 3.0. Compound #59, which was shown inhibition at greater than or equal to 3.0 log 10 at 50 µM and between 1.0 and 3.0 log 10 inhibition at 5 µM, was also included. For HSV-1, $EC_{50}$ values ranged from 4.20 µM for compound #30 down to 0.24 µM for #49. For HSV-2, the values ranged from 4.12 µM for compound #59 down to 0.22 µM for #49. For comparison, ACV had $EC_{50}$ values of 0.16 and 1.44 µM versus HSV-1 and HSV-2, respectively. $EC_{50}$ values were also measured for compounds #30, 41, 46, 49 55, 56 and 59 in HFF cells (Table 4). These values ranged from 2.81 to 0.13 µM for HSV-1 and from 1.67 to 0.38 µM for HSV-2, again demonstrating their activity in a natural host cell. Overall, the $EC_{50}$ data confirmed the highly effective inhibition of HSV-1 and HSV-2 by these compounds that was observed in the primary screening assays.

Herpesvirus inhibitors affect multiple stages of viral replication. Two experiments were conducted to begin resolving how these compounds inhibit herpesvirus replication. First, the effect of the strong inhibitors #30, #41, #46 and #56 on production of infectious virus and viral DNA replication for HSV-2 was simultaneously assessed. Viral replication was measured 24 hours post-infection by plaque assay, and DNA replication was measured using quantitative PCR against the LAT gene and expressed as genome-equivalents (GE). As shown in Table 3, viral DNA replication was suppressed by 150- to 615-fold, but production of infectious virus was reduced by 676- to 331,000-fold. Therefore, in addition to suppressing viral DNA replication, these inhibitors also suppressed the fraction of viral genomes that was associated with infectious virus. This is most easily seen by comparing suppression of PFU to suppression of GE accumulation in FIG. 4; note that the scale for GE suppression is 100-fold smaller than for PFU suppression. Two inhibitor concentrations were assessed for compounds #30 (60 and 20 µM) and #46 (20 and 10 µM). Suppression of DNA replication and PFU accumulation was dose-dependent for both #30 and #46.

The inventors next varied the time post-infection that the inhibitors were added to begin defining the stage(s) of viral replication targeted by the inhibitors. Acyclovir and compounds #41 and #46 were added to cell monolayers at 10 µM concurrently with HSV-2 (0 hour post-infection) or at 1, 3, 5, 7, 9 or 12 hours post-infection. The cells were incubated until 24 hours post-infection and then infectious viral titers were determined by plaque assay and viral DNA production was determined by quantitative PCR (FIG. 5).

Acyclovir inhibited both DNA replication and accumulation of infectious virus. Its effect on virus accumulation was larger than on DNA accumulation when it is added early post-infection, and the differential effect became negligible when compound addition was delayed to ≥9 hours post-infection. Delaying addition of acyclovir until 5 hours post-infection had no effect on inhibition of either DNA replication or viral accumulation. Addition of acyclovir at 7 hours or later post-infection led to its gradual loss of activity, and it became essentially ineffective when addition was delayed until 12 hours post-infection. These data indicate that events targeted by ACV start between 5-7 hours post-infection and are finished by ~12 hours post-infection. This is fully consistent with ACV's known mechanism as an inhibitor of viral DNA elongation.

Figure 4:
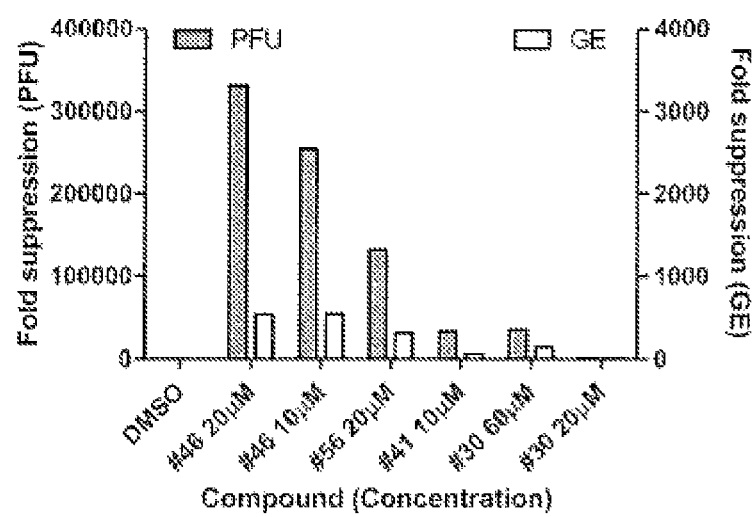
FIG. 4. Greater suppression of infectious HSV-2 production than DNA synthesis. Vero cells were infected with HSV-2 at an moi of 0.1 in the presence of the indicated concentration of compound, or an equivalent concentration of DMSO diluent. At 24 hours post-infection, replicate cell cultures were collected and processed for determination of viral titer (plaque-forming units; PFU), or viral DNA levels by quantitative PCR (genome equivalents; GE). The PFU and GE for DMSO were set to 1 and -fold suppression in the presence of compound was calculated relative to DMSO. Note the scale of the right-hand y-axis is $\frac{1}{100}^{th}$ that of the left-hand y-axis.
Figure 5:
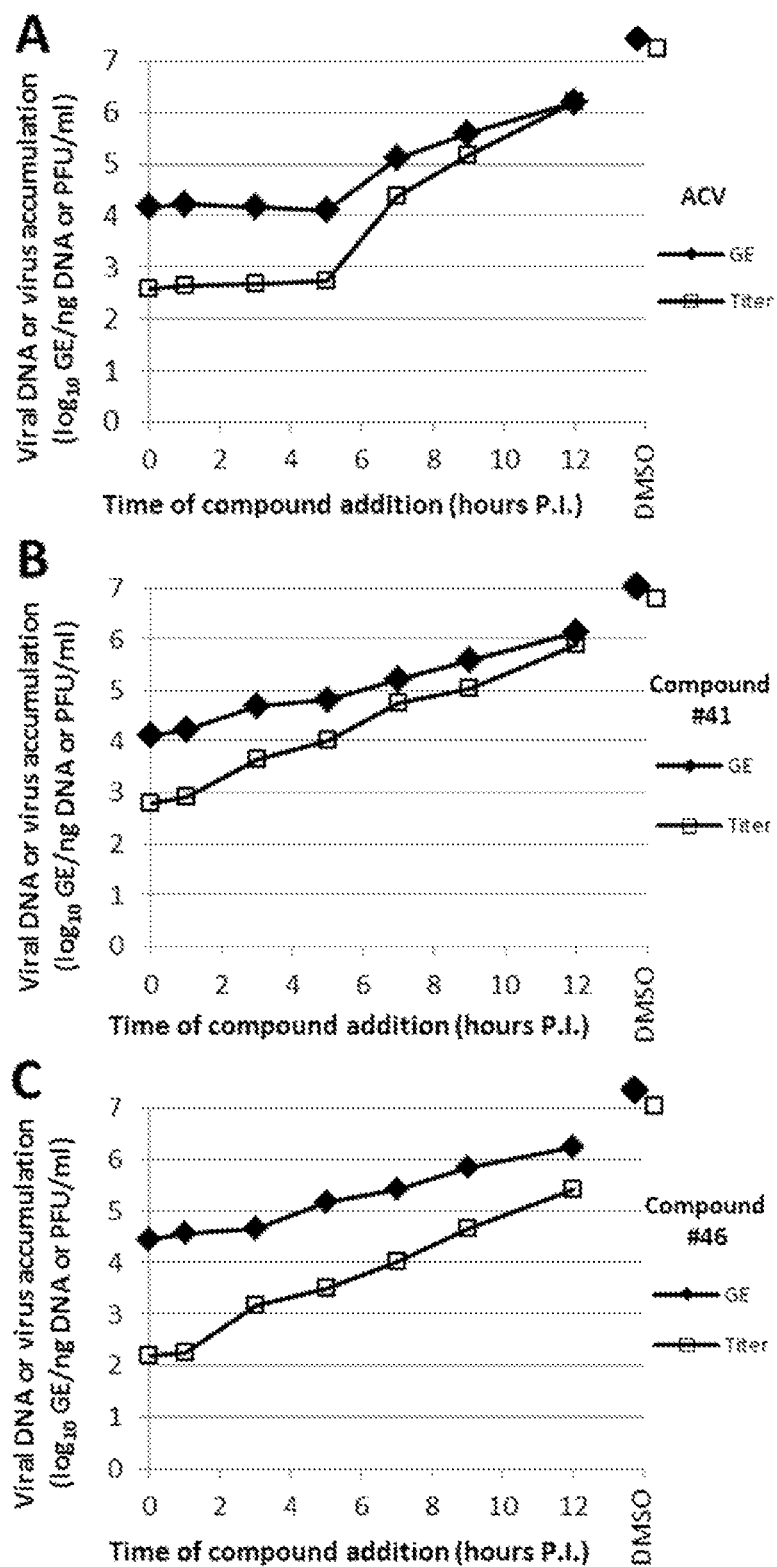
FIG. 5. Effects on viral titers and genome accumulation from delaying inhibitor addition for 0-12 hours post-infection. Compounds were added to Vero cells at 10 µM either concurrently with infection at moi of 0.1 (time 0) or at the indicated times post-infection, and cells were harvested 24 hours post-infection. Viral titers were determined by plaque assay and expressed as the average PFU/ml of duplicate cultures. DNAs were isolated from replicate wells (supernatant plus cells) and viral DNA content was measured by quantitative PCR. Viral DNA was expressed as GE/ng total DNA. Values are the average of two replicate samples per time point. DMSO indicates values from the parallel vehicle-treated control cultures at 24 hours post-infection. The experiment was repeated with similar results.

Compounds #41 and 46 also inhibited both DNA replication and accumulation of infectious virus, and the effect of these compounds was again much larger on virus accumulation than on DNA replication (compare FIGS. 4 and 5). As with acyclovir, this differential effect was primarily observed when the inhibitors were added early in infection. In contrast to acyclovir, compounds #41 and 46 also inhibited a very early step in viral replication. This is apparent because accumulation of virus began to recover when compound addition was delayed until 1-3 hrs post-infection. Again in contrast to acyclovir, there was no clearly defined point where efficacy of compounds #41 and #46 began to fail. The effect of delaying addition of the compounds was linear with respect to compound addition time between 1-12 hours post-infection, and they become essentially ineffective when added after 12 hours post-infection.

Figure 7:
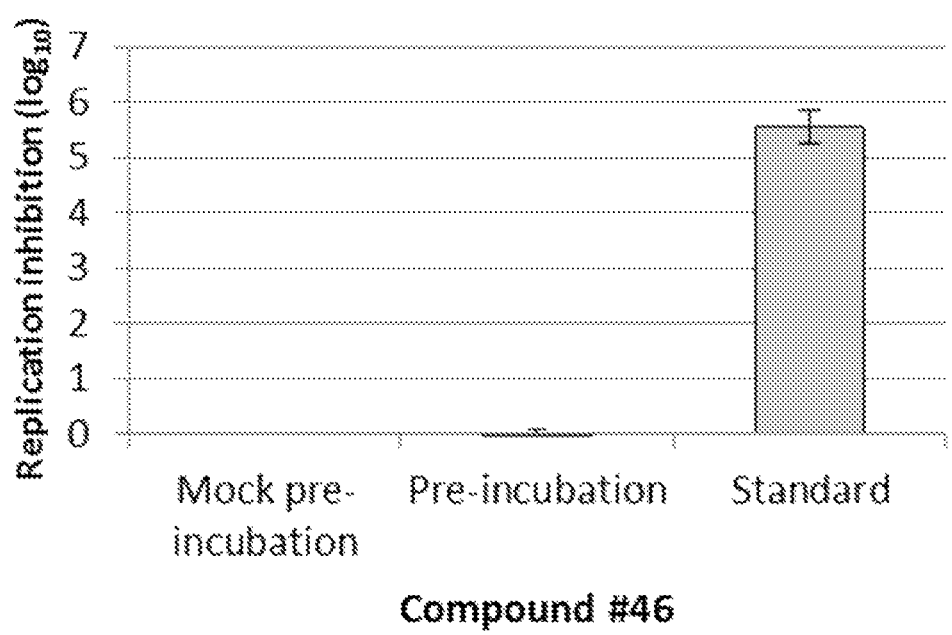
FIG. 7. Effect of pre-incubating compound #46 and the viral inoculum on virus infectivity. A high-titer HSV-1 stock was pre-incubated in 50 µM compound #46 or DMSO control (mock pre-incubation). The inoculum was then diluted to reduce #46 to 0.05 µM and virus titer such that a standard replication inhibition assay at moi of 0.1 was performed. Compound #46 was added to 0.05 µM in the mock pre-incubation sample for consistency. A standard inhibition assay in which compound #46 was used at 50 µM throughout the assay was included as a control. Values are the averages±one standard deviation from two experiments, each done in duplicate.

Tests were carried out to determine if the early event inhibited by compound #46 was a pre- or post-entry event. A high titer HSV-1 stock was pre-incubated with compound #46 at 50 μM or was incubated with an equivalent amount of DMSO-containing medium for 1 hour at 37° C. Then the viral stocks with compound or DMSO were diluted such that Vero cells were infected at a moi of 0.1 as usual. This dilution also reduced the amount of compound #46 carried over from the pre-incubation to a negligible concentration of 0.05 μM during the infection period. A standard inhibition assay using compound #46 at 50 μM was conducted in parallel as a positive control, and viral titers were determined by plaque assay at 24 hours post-infection. The standard conditions of infection at 50 μM caused a 5.5 $\log_{10}$ suppression of HSV-1 replication relative to the DMSO pre-treatment sample. Titers in the DMSO pre-incubated and compound #46 pre-incubated samples were comparable (FIG. 7), indicating that compound #46 was not directly toxic to virions and exposure of the virus to the compound did not inhibit virus entry into cells.

Together, these studies indicate that compounds #41 and #46 inhibit at least one critical event that occurs at a very early post-entry stage of viral replication, plus at least one event that occurs during a later phase of the replication cycle.

Inhibition of acyclovir-resistant HSV-1 and HSV-2 mutants. ACV is a nucleoside analog prodrug that must be phosphorylated by the viral thymidine kinase (TK) for it to become a substrate for the viral DNA polymerase (Elion, et al., 1977). HSV TK-deficient mutants are therefore insensitive to ACV. Because viral resistance to ACV and other nucleoside analogs is a significant medical problem (Field and Biron, 1994; Coen, 1991; Wang, et al, 2011; Duan, et al., 2009; Duan, et al., 2008; Pelosi, et al., 1992), especially in immunocompromised patients (Reyes, et al., 2013; Levin, et al., 2004; Gilbert, et al., 2002; Schmit and Boivin, 1999), we asked whether defined TK-deficient mutants of HSV-1 and HSV-2 would be sensitive to NTS inhibitors. Vero cells were infected with laboratory strains of HSV-1 or HSV-2 and engineered TK-deficient mutants of the same strains. The cells were treated with 50 μM ACV or compounds #30, 41, or 46 as was done in the primary screening assays, and viral yields 24 hours post-infection were measured by plaque assay. ACV efficiently inhibited wild-type HSV-1 and HSV-2 replication, but it had little effect on the TK-mutants (FIG. 8A). In marked contrast, compounds #30, 41, and 46 efficiently inhibited the TK-mutant strains of both HSV-1 and HSV-2. Similar patterns were seen when the compounds were used at 5 μM (FIG. 8B), although inhibition by compound #30 at 5 μM was too low to definitively interpret. Therefore, these NTS inhibitors from three different chemical families do not require phosphorylation by the viral TK gene to be active, confirming that the NTS inhibitors suppress HSV-1 and HSV-2 replication in a different manner than ACV.

TABLE 1

HSV-1 and HSV-2 suppression by anti-integrase or RNaseH compounds.

| Compound Number | Name | Anti-HSV-1 [1] $\log_{10}$ suppression 50 μM | 5 μM | EC50 (μM) | Anti-HSV-2 [1] $\log_{10}$ suppression 50 μM | 5 μM | EC$_{50}$ (μM) | Anti-HBV RNaseH [2] | Anti-Human RNaseH1 [2] |
|---|---|---|---|---|---|---|---|---|---|
| | | | | Tropolones | | | | | |
| 46 | Beta-thujaplicinol | 4.81 | 5.01 | 1.94 | 5.12 | 5.32 | 1.69 | +++ | + |
| 47 | Beta-thujaplicin | 1.86 | 0.31 | | 1.38 | 0.22 | | − | − |
| 48 | Gamma-thujaplicin | 4.71 | 0.31 | | 4.57 | 0.20 | | − | − |
| 49 | Nootkatin | 4.72 | 5.10 | 0.24 | 5.05 | 4.91 | 0.22 | − | − |
| 50 | 5-nitrosotropolone | T | 2.07 | | + | 1.98 | | − | − |
| 52 | NSC 79556 | 2.02 | 0.07 | | 1.34 | 0.10 | | − | − |
| 53 | Tropolone | 1.90 | 0.25 | | 1.45 | 0.45 | | − | − |
| 55 | NSC 282885 | 5.04 | 3.62 | 0.42 | 5.06 | 2.93 | 1.07 | + | + |
| 56 | Manicol | 5.82 | 5.14 | 0.35 | 5.79 | 5.95 | 0.58 | +++ | − |
| 59 | Chembridge 5945310 | 4.24 | 1.65 | 1.09 | 4.71 | 1.22 | 4.12 | − | + |
| 61 | Chembridge 5940946 | T | 0.15 | | − | 0.23 | | − | ++ |
| 62 | Chembridge 5946384 | 2.36 | 0.38 | | 1.93 | 0.03 | | − | − |
| | | | | Polyoxygenated heterocycles | | | | | |
| 1 | TRC 939800 | 2.66 | 0.28 | | 3.12 | −0.11 | | +++ | ++ |
| 41 | Ciclopirox | 5.23 | 4.29 | 0.27 | 5.25 | 5.50 | 0.45 | − | + |

TABLE 1-continued

HSV-1 and HSV-2 suppression by anti-integrase or RNaseH compounds.

| Compound Number | Name | Anti-HSV-1 [1] Log$_{10}$ suppression 50 μM | Anti-HSV-1 [1] Log$_{10}$ suppression 5 μM | EC50 (μM) | Anti-HSV-2 [1] Log$_{10}$ suppression 50 μM | Anti-HSV-2 [1] Log$_{10}$ suppression 5 μM | EC$_{50}$ (μM) | Anti-HBV RNaseH [2] | Anti-Human RNaseH1 [2] |
|---|---|---|---|---|---|---|---|---|---|
| 42 | Labotest 72543251 | − | − | | − | − | | − | + |
| 43 | Sigma PH008969 | 1.31 | 0.31 | | 1.13 | 0.31 | | − | − |
| 44 | Labotest 12243782 | − | − | | − | − | | − | − |
| 45 | TCI America-H1040 | − | − | | − | − | | − | − |
| | | | | Hydroxyxanthenones | | | | | |
| 8 | Sigma S439274 | 0.86 | −0.18 | | 2.49 | 0.18 | | ++ | +++ |
| 30 | Chembridge-7248520 | 4.02 | 1.39 | 4.20 | 4.55 | 3.69 | 3.93 | +++ | +++ |
| 31 | Chembridge-5104346 | 3.01 | 0.21 | | 3.56 | 0.22 | | +++ | +++ |
| 34 | Indofine-D-009 | 2.64 | 0.08 | | 3.29 | −0.07 | | ++ | − |
| 35 | TCI America-D1118 | − | − | | − | − | | +++ | +++ |
| 39 | Asinex-BAS0223612 | 0.22 | 0.19 | | 0.17 | 0.12 | | +++ | +++ |
| | | | | Integrase strand-transfer inhibitors | | | | | |
| 10 | Elvitegravir | − | − | | − | − | | − | − |
| 11 | Raltegravir | 0.37 | 0.2 | | 0.35 | 0.25 | | − | − |
| 66 | Sigma PHR1174 | + | − | | − | − | | − | |
| 70 | Sigma N8878 | − | − | | − | − | | − | |
| | | | | Aminocyanothiophenes | | | | | |
| 6 | Chembridge 7929959 | − | − | | − | − | | + | |
| 24 | Chembridge-7933420 | − | − | | − | − | | − | |
| 27 | Chembridge-7698174 | − | − | | − | − | | − | |
| 28 | Chembridge-7570508 | 1.37 | 0.17 | | 0.61 | 0.08 | | − | − |
| | | | | Cyanopyrans | | | | | |
| 5 | Enamine T0506-3483 | − | − | | − | − | | + | |
| 19 | Sigma-586862 | − | − | | − | − | | − | |
| 21 | Sigma-S647632 | − | − | | − | − | | − | |
| | | | | Napthyridinones | | | | | |
| 12 | CWHM-000618 | 1.70 | 0.10 | | 2.07 | −0.08 | | | |
| 148 | CWHM-000613 | − | − | | − | − | | | |
| 149 | CWHM-000614 | 2.12 | − | | 1.97 | − | | | |
| 150 | CWHM-000615 | T | 0.16 | | T | 0.45 | | | |
| 151 | CWHM-000616 | T | 2.16 | | T | 2.26 | | | |
| 152 | CWHM-000617 | − | − | | − | − | | | |
| 153 | CWHM-000631 | 1.44 | 0.22 | | 0.73 | 0.07 | | | |
| 154 | CWHM-000632 | T | − | | T | − | | | |
| 155 | CWHM-000633 | T | 3.85 | | T | 3.88 | | | |
| | | | | Miscellaneous compounds | | | | | |
| 2 | Sigma 74540 | 3.21 | −0.19 | | 4.38 | −0.15 | | − | − |
| 3 | Sigma n8164 | −0.03 | 0.19 | | 0.39 | 0.06 | | − | |
| 4 | TimTec ST029023 | − | − | | − | − | | + | |
| 7 | Idofine 02030 | 0.48 | 0.44 | | 1.26 | 0.03 | | − | +++ |
| 9 | Sigma 70050 | 0.38 | 0.30 | | 0.67 | −0.04 | | ++ | ++ |
| 22 | Sigma-N8164 | − | − | | − | − | | − | |
| 38 | Vistas M Lab-STK317995 | 0.07 | −0.07 | | −0.05 | 0.11 | | +++ | |
| | | | | Nucleos(t)ide analogs | | | | | |
| ACV | Acyclovir | 5.85 | 4.49 | 0.16 | 5.25 | 3.91 | 1.44 | − | − |
| CID | Cidofovir | 2.67 | 0.77 | | 1.19 | 0.38 | | − | − |

[1] HSV screening: +, inhibition at 50 μM; T, not titered due to toxicity; −, no change in cytopathic effect.
[2] HBV and human RNaseH1 screening: +++, inhibition at 10 μM; ++, inhibition at 20 μM; +, inhibition at 60 μM; −, no inhibition at 60 μM.

TABLE 2

| | | Vero Cell Toxicity | | |
|---|---|---|---|---|
| | | | Vero cell toxicity | |
| Compound Number | Name | Qualitative[3] | MTT $CC_{50}$ (μM) | CTG $CC_{50}$ (μM) |
| Tropolones | | | | |
| 46 | Beta-thujaplicinol | | >100 | >100 |
| 47 | Beta-thujaplicin | | | |
| 48 | Gamma-thujaplicin | | | |
| 49 | Nootkatin | | >100 | >100 |
| 50 | 5-nitrosotropolone | T | | |
| 52 | NSC 79556 | | | |
| 53 | Tropolone | | | |
| 55 | NSC 282885 | | >100 | >100 |
| 56 | Manicol | | >100 | ~100 |
| 59 | Chembridge 5945310 | | ~100 | >100 |
| 61 | Chembridge 5940946 | T | | |
| 62 | Chembridge 5946384 | | | |
| Polyoxygenated heterocycles | | | | |
| 1 | TRC 939800 | T? | >100 | >100 |
| 41 | Ciclopirox | | >50 | >100 |
| 42 | Labotest 72543251 | | | |
| 43 | Sigma PH008969 | | | |
| 44 | Labotest 12243782 | | | |
| 45 | TCI America - H1040 | | | |
| Hydroxyxanthenones | | | | |
| 8 | Sigma S439274 | | | |
| 30 | Chembridge - 7248520 | | >100 | >100 |
| 31 | Chembridge - 5104346 | | >100 | >100 |
| 34 | Indofine - D-009 | | | |
| 35 | TCI America - D1118 | | | |
| 39 | Asinex - BAS0223612 | | | |
| Integrase strand-transfer inhibitors | | | | |
| 10 | Elvitegravir | T | | |
| 11 | Raltegravir | | | |
| 66 | Sigma PHR1174 | | | |
| 70 | Sigma N8878 | | | |
| Aminocyanothiophenes | | | | |
| 6 | Chembridge 7929959 | | | |
| 24 | Chembridge - 7933420 | | | |
| 27 | Chembridge - 7698174 | T | | |
| 28 | Chembridge - 7570508 | | | |
| Cyanopyrans | | | | |
| 5 | Enamine T0506-3483 | | | |
| 19 | Sigma - 586862 | | | |
| 21 | Sigma - S647632 | | | |
| Napthyridinones | | | | |
| 12 | CWHM-000618 | | | |
| 148 | CWHM-000613 | | | |
| 149 | CWHM-000614 | | | |
| 150 | CWHM-000615 | T | | |
| 151 | CWHM-000616 | T | | |
| 152 | CWHM-000617 | | | |
| 153 | CWHM-000631 | | | |
| 154 | CWHM-000632 | T | | |
| 155 | CWHM-000633 | T | | |
| Miscellaneous compounds | | | | |
| 2 | Sigma 74540 | | >100 | >100 |
| 3 | Sigma n8164 | | | |
| 4 | TimTec ST029023 | | | |
| 7 | Idofine 02030 | | | |
| 9 | Sigma 70050 | | | |
| 22 | Sigma - N8164 | | | |
| 38 | Vistas M Lab - STK317995 | | | |
| Nucleos(t)ide analogs | | | | |
| ACV | Acyclovir | | >100 | >100 |
| CID | Cidofovir | | | |

Qualitative toxicity assessment: T, visual evidence of toxicity at 50 μM.

TABLE 3

Relative effects of HSV-2 inhibitors on viral DNA replication and infectious virus accumulation.

| | Fold suppression | | |
|---|---|---|---|
| Compound | GE | PFU | PFU/GE |
| DMSO | 0 | 0 | 1 |
| #30 60 µM | 247 | 35500 | 143.7 |
| #30 20 µM | 150 | 676 | 4.5 |
| #41 10 µM | 551 | 34159 | 62.0 |
| #46 20 µM | 615 | 331000 | 538.2 |
| #46 10 µM | 470 | 254536 | 541.6 |
| #56 20 µM | 420 | 132000 | 314.3 |

TABLE 4

Inhibition of HSV-1 and HSV-2 replication in primary human foreskin fibroblasts

| | Replication inhibition[1] | | | | | | |
|---|---|---|---|---|---|---|---|
| Com- | HSV-1 | | | HSV-2 | | | |
| pound | 50 µM | 5 µM | $EC_{50}$[2] | 50 µM | 5 µM | $EC_{50}$ | Toxicity[3] |
| DMSO | 0 | 0 | | 0 | 0 | | NA |
| ACV | 6.69 | 5.25 | 0.12 | 6.27 | 4.01 | 0.12 | >100 |
| #30 | 5.23 | 3.22 | 0.32 | 6.68 | 2.04 | 0.52 | >100 |
| #41 | 5.57 | 5.06 | 0.14 | 4.97 | 5.21 | 1.00 | >100 |
| #46 | 6.39 | 5.83 | 0.97 | 5.83 | 5.17 | 0.38 | >100 |
| #47 | 5.06 | 0.02 | | 5.16 | 0.08 | | >100 |
| #48 | 5.99 | 0.05 | | 5.76 | 0.20 | | >100 |
| #49 | 6.27 | 5.79 | 0.74 | 5.98 | 5.47 | 1.23 | >100 |
| #50 | NQ[4] | 2.92 | | NQ | 2.88 | | 40.4 |
| #52 | NQ | 0.10 | | NQ | −0.01 | | >100 |
| #53 | 2.13 | −0.03 | | 1.22 | 0.29 | | >100 |
| #55 | 6.17 | 4.99 | 2.81 | 6.55 | 3.94 | 1.67 | >100 |
| #56 | 6.39 | 5.72 | 0.24 | 6.80 | 5.93 | 0.55 | >100 |
| #59 | 6.03 | 2.56 | 1.63 | 5.41 | 1.16 | 0.84 | >100 |
| #61 | NQ | −0.17 | | NQ | −0.05 | | 27.8 |
| #62 | 3.35 | 0.12 | | 2.32 | 0.02 | | >100 |

[1]Replication inhibition ($log_{10}$) relative to DMSO-treated control cultures.
[2]Values in µM.
[3]$CC_{50}$ by MTT assay, µM.
[4]NQ, Not quantified due to visible toxicity.

Figure 9A:
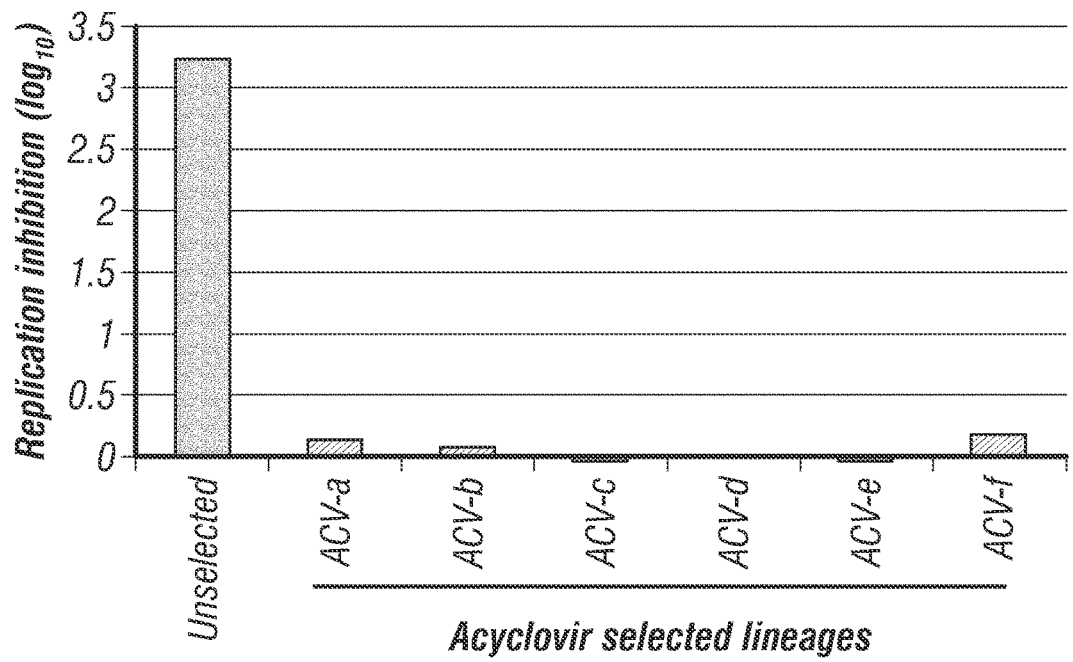
FIGS. 9A-C. Antiviral resistance to NTS inhibitors develops slowly. HSV-1 strain KOS was used to infect Vero cells in the presence of ACV or NTS inhibitors #41 or #46 for three rounds of growth. Multiple independent lineages were then compared to the unselected KOS strain for their sensitivity to the inhibitor.
Figure 9B:
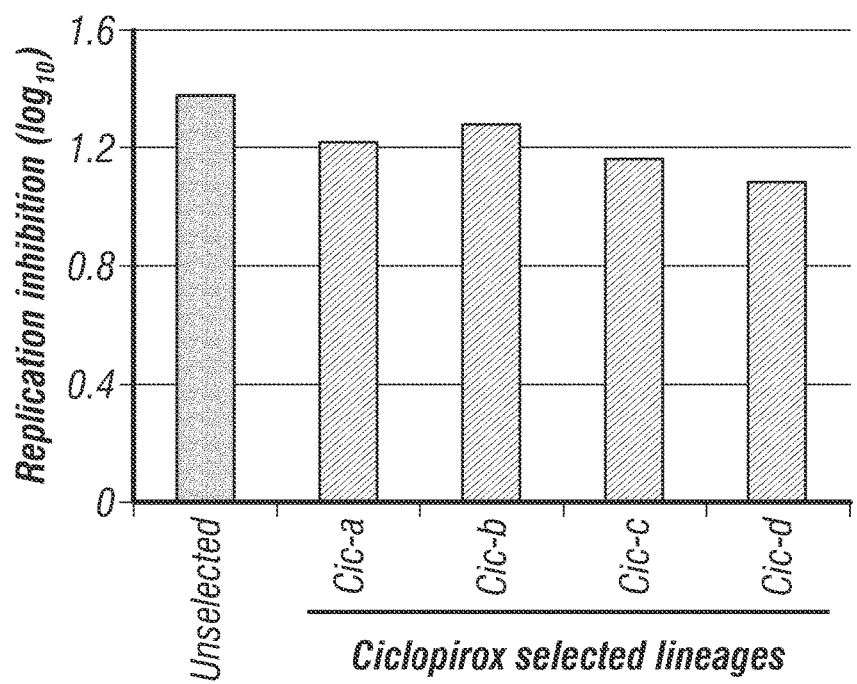
Figure 9C:
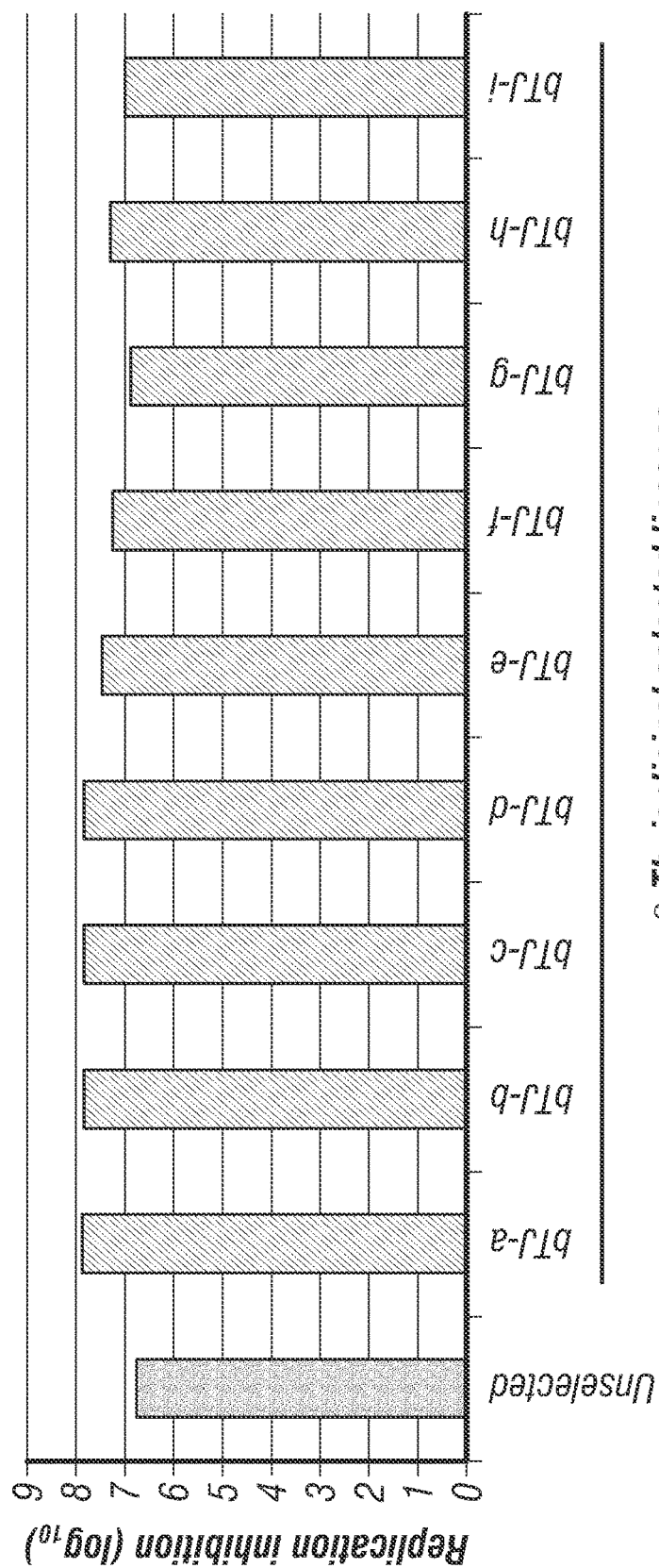

Resistance evolution against NTS inhibitors ciclopirox (#41) and β-thujaplicinol (#46) develops more slowly than against ACV. HSV-1 strain KOS was passaged three times in the presence of ACV, #41 or #46. Individual independent lineages collected after the third round were then compared with the original KOS strain for their capacity to replicate in the presence of the inhibitor on which they were selected (FIG. 9). After just 3 rounds of growth in the presence of ACV, all 6 independent lineages of ACV-selected virus no longer could be inhibited by ACV, whereas ACV treatment inhibited KOS replication more than 1700-fold (FIG. 9A). In marked contrast, 4 independent lineages of ciclopirox-selected virus (FIG. 9B) and 9 independent lineages of β-thujaplicinol-selected virus (FIG. 9C) remained as sensitive to inhibition by ciclopirox and β-thujaplicinol, respectively, as unselected KOS. Thus, resistance evolution in the presence of the nucleoside analog drug ACV consistently develops very rapidly in culture, but viral resistance to NTS inhibitors develops much more slowly. This explicitly demonstrates that both compound #41 and #46 apply a much higher barrier to evolution of resistance than does ACV.

3. Discussion

Together the studies described above lead to four primary observations. First, the herpesvirus inhibitors suppress viral DNA replication. Second, the inhibitors can suppress ongoing viral replication in a cell. Third, the compounds reduce the fraction of viral DNA associated with infectious virions. Finally, the inhibitors primarily block infectious virus accumulation by targeting a very early event in the infectious cycle, and they also can block DNA accumulation at later stages of the cycle.

The complex DNA replication mechanism employed by the herpesviruses uses enzymes with catalytic properties, that without being bound by theory, it is hypothesized that the enzymes would be highly sensitive to inhibitors of NTS enzymes. 42 compounds known or predicted to inhibit NTS enzymes based on their efficacy against HIV and/or HBV were screened for the ability to inhibit HSV-1 and HSV-2 replication. Eighteen of these compounds (43%) inhibited HSV-1 replication by >1 $log_{10}$ in short-term cell culture experiments in Vero cells at ≤50 µM, and 19 inhibited HSV-2 (Table 1). All inhibitors, which showed greater than 1.0 log 10 inhibition, identified in Vero cells were also active in HFF cells (FIG. 2 and Table 2), confirming their capacity to block HSV replication in a relevant cell type from their natural human host. The pattern of inhibition by the compound set against HSV-1 and HSV-2 was quite similar. This high hit rate for a small primary screening study provides strong support for the hypothesis that NTS enzymes are promising targets for anti-herpesvirus drug development.

Multiple compounds were assessed from six chemical families (hydroxylated tropolones; N-hydroxyisolinolinediones, HIV strand-transfer inhibitors, cyanopyrans; aminocyanothiophenes, and hydroxyxanthenones) in an initial effort to determine whether sets of related compounds had interpretable patterns of inhibition against HSV-1 and HSV-2. Six hydroxytropolones inhibited viral replication by >1 $log_{10}$ at 5 µM (#46, 49, 50, 55, 56, and 59), one inhibitor was found in the N-hydroxyisolinolinedione class (#41) and one in the hydroxyxanthenone class (#30). No hits were found among the other chemical families, each of which contains one or more compounds known to inhibit the HIV integrase or RNaseH, or the HBV RNaseH (Table 1 and FIG. 1). These data indicate that NTS antagonists from multiple distinct chemical families can inhibit both HSV-1 and HSV-2.

Sufficient data exist for the tropolone family to establish constraints on the structure-activity relationship for this compound class. Comparing the structures of compounds #46 with #47, 48, 50, and 53 (FIG. 1) indicates that efficient inhibition in the absence of extended R groups at the α, β, or γ positions of the tropolone ring requires three adjacent cation-chelating moieties (the contiguous hydroxyl and carbonyl groups). Of the six larger compounds (#49, 52, 55, 56, 59, 61, and 62), four were inhibitors (#49, 55, 56, and 59) showing greater than 1.0 log 10 inhibition. Three of these four compounds (#49, 52, and 55) had only two metal-chelating moieties on the tropolone ring, but the fourth compound (#56) had three chelating moieties and was the strongest inhibitor identified to date. The two larger compounds that were negligible inhibitors each had a side chain extending from the oxygen adjacent to the carbonyl on the tropolone ring which could interfere with metal ion chelation. These data imply that a carbonyl plus a modified hydroxyl is insufficient to support inhibition, and that three chelating moieties on the tropolone ring are superior to two. Finally, the three inhibitors (#49, 55, 56) showed greater than 3.0 log 10 inhibition and one inhibitor (#59), which showed inhibition from between 1.0 to 3.0 log 10 inhibition, had a wide variety of R groups on the face of the tropolone ring opposite from the metal-chelating motifs, indicating that significant structural diversity is permitted in these elements. The wide range of $EC_{50}$ values for these four robust inhibitors (0.24 to 1.09 µM for HSV-1 and 0.22 to 4.12 µM for HSV-2) implies that the chemical elements opposite the putative chelating moieties can significantly impact the efficacy of the compounds.

Little to no cytotoxicity was observed for these compounds in short-term (24 hr) cell culture experiments by either the MTT assay that measures mitochondrial function or by assessing cell rupture (Tables 1, 2, and 4). Compounds #50 and 61 caused some toxicity in HFF cells, but in all other cases the $CC_{50}$ values were higher than the 50 µM maximal concentration used during antiviral screening. In addition, we observed inhibition of purified human RNaseH 1 at <60 µM for only one compound (#30) that was an inhibitor of HSV replication (Table 1) showing inhibition greater than 1.0 log 10 inhibition. This indicates that cytotoxicity is not a confounding factor in our screening, and it is promising with regard to the drug potential of these compound classes. However, we do not wish to leave the impression that toxicity will not be a concern during subsequent drug development. Hydroxylated tropolones have been shown to induce varying degrees of mitochondrial toxicity in rats (Nakagawa and Tayama, 1998), and compound #46 has $CC_{50}$ values of 2 to 16 µM in CEM-SS, Huh7, and HepG2 cells (Hu et al., 2013; Chung et al., 2011). These observations suggest that further scrutiny of NTS compounds in a variety of cell types will be warranted.

Initial evidence concerning the stage(s) of viral infection targeted by the NTS inhibitors suggests that the NTS inhibitors block more than one event in the viral replication cycle. The pre-incubation experiment in FIG. 7 demonstrated that compound #46 is not directly virucidal. Furthermore, the time-of-addition experiment in FIG. 5 demonstrated that compounds #41 and 46 are equally effective when added after the 1 hour infection window as they are when added concurrently with infection. These results indicate that the NTS antagonists inhibit HSV replication at post-entry step(s). The time-of-addition experiment in FIG. 5 also revealed that compounds #41 and 46 interfere with events occurring between 1 and 12 hours post-infection. The partial loss of activity when addition of compounds #41 and 46 was delayed until 3 or 5 hours post-infection is in sharp contrast to the lack of effect that delaying ACV addition had during this time. The NTS inhibitors therefore suppress an activity important for viral replication that occurs prior to the onset of viral DNA replication. The continued gradual loss of activity if addition of compounds #41 and 46 was delayed more than 5 hours post-infection indicates that these inhibitors also inhibit events that transpire concurrently with viral DNA replication. Plausible events affected by the NTS inhibitors during this broad time period include genome circularization, DNA replication and primer removal, recombination of the viral genome to produce branched concatamers, and the early stages of genome maturation for packaging into capsids. More study will be required to identify the specific events in the viral replication cycle targeted by the compounds.

It is unknown whether the events suppressed by these NTS inhibitors represent a single target whose activity is needed at multiple stages of the viral replication cycle, or multiple targets that are each needed for viral replication. However, without being bound by theory, the extremely high hit rate in this small screen, the high efficacy of the inhibitors, and the gradual loss of activity in the time-of-addition experiments together favor the possibility that the NTS inhibitors act against multiple enzymes that function at different stages of the replication cycle. In this context, the gradual loss of activity with increasing time of addition would be due to adding the compounds after one or more of the targets had performed their functions. The events controlled by these enzymatic functions may also occur less abruptly than onset of viral DNA replication. Activity against multiple targets would have major implications for the utility of NTS inhibitors as anti-herpesvirus drugs because it would suggest an inherently high barrier for evolution of resistance to this class of drugs.

The inhibitors screened here function against HIV by binding to the viral RNaseH or integrase active sites and chelating the essential divalent cations within the active site (Chung, et al., 2011; Su, et al., 2010; Fuji, et al., 2009; Himmel, et al., 2009; Billamboz, et al., 2011; Kirschberg, et al., 2009). Therefore, their presumed mechanism of action against the HSVs is to inhibit one or more NTS enzymes essential for viral genomic replication by binding to their active site(s). This could explain why a compound (#56) with three chelating moieties on the tropolone ring was the strongest inhibitor of HSV-1 and HSV-2.

The absence of cytotoxicity in these assays suggests that at least some of the target(s) of the NTS inhibitors are viral enzyme(s). Candidate HSV genes include the RNaseH activity of the pUL30 DNA polymerase (Liu, et al., 2006), the 3'-5' exonuclease activity of pUL30 (Coen, 1996), or the 5'-3' exonuclease activity of the pUL12 polymerase accessory protein (Schumacher, et al., 2012) that are directly involved in virus DNA replication (Weller and Coen, 2012). The pUL15 terminase protein that cleaves the viral DNA concatamer produced by genomic replication into the mature linear monomers is known to be an NTS enzyme and is also a candidate (Selvarajan, et al., 2013). Cellular proteins used by HSVs during their replication are also plausible targets for the NTS inhibitors. Candidates include human RNaseH 1 and the Fen1 endonuclease that may remove RNA primers during DNA synthesis (Zhu, et al., 2010), the double-stranded break repair enzymes Mre11, Rad50, NBS1, Rad51 (Weizman and Weller, 2011) and Rad52 (Schumacher, et al., 2012), and the base-excision repair enzymes SSH2 and MHL1 (Mohni, et al., 2011). SSH2 and MHL1 are both known to form complexes that are recruited to viral replication sites and contribute to HSV genomic replication (Mohni, et al., 2011).

These data strongly imply that the NTS inhibitors identified here work by a different mechanism than the approved anti-herpesvirus drugs. The existing drugs are primarily nucleoside analogs that become incorporated into the growing DNA strands and terminate DNA elongation. Other inhibitors of DNA synthesis such as foscarnet block DNA synthesis by being non-hydrolysable pyrophosphate analogs (Marchand, et al., 2007; Derse, et al., 1982) HSV-2 strains resistant to ACV have been demonstrated to be sensitive to NTS inhibitors (FIGS. 8A-B), and none of the NTS antagonists employed are nucleos(t)ide analogs or pyrophosphate mimetics (FIG. 1). Furthermore, unlike most nucleos(t)ide analogs, it has been demonstrated that compounds #30, 41, and 46 do not require phosphorylation by the viral thymidine kinase gene to be active. The different mechanism of viral suppression by the NTS inhibitors has direct implications for their potential use as anti-herpesvirus drugs. First, it implies that NTS inhibitors could be used as salvage therapies for nucleoside analog-resistant infections. Second, it raises the possibility of additive or synergistic activity of NTS and nucleoside analog drugs that could significantly improve therapeutic efficacy. Finally, it suggests that combination therapy employing anti-NTS drugs and the nucleoside analogs could reduce the rate at which resistance would evolve to either drug class.

The high efficacy of the primary hits identified among three different chemical families of NTS inhibitors, coupled with their different mechanism(s) of action relative to the approved nucleoside analog inhibitors, make NTS antagonists attractive candidates for novel anti-herpesvirus therapies to complement the existing drugs.

4. In vitro Testing Against HCMV

Antiviral efficacy against HCMV. The ability of select HSV inhibitors to inhibit replication of another major human herpesvirus pathogen, human cytomegalovirus (HCMV) (65) was tested. This was based on the inhibitors strong suppression of HSV-1 and HSV-2 and the prediction that other members of the herpesvirus family would be sensitive to NTS inhibitors due to their shared DNA replication mechanism. Compounds #41, 46, 49, 55, 56, and 59 and the FDA-approved anti-HCMV drug ganciclovir were evaluated with crystal violet CPE and neutral red toxicity assays in HFFs. HFFs were infected with HCMV in the presence of serial dilutions of the compounds that were most inhibitory for HSVs. After 14 days the monolayers were stained and cell density was determined by OD reading. Compound cytotoxicity for uninfected cells was determined in the same manner except that neutral red uptake by viable cells was measured. Compounds #41, 46, 49, 56, and 59 inhibited HCMV replication with $EC_{50}$ values in the very low µM range (Table 5). In contrast to the 24 h HSV assays in HFF, compounds #41, 56, and 59 had measurable toxicity in this 14 day assay, most notably #41 with a $CC_{50}$ of 8.9 µM. The TI values for the four NTS inhibitors of HCMV ranged from 4 for compound #41 to 38 for #56. Therefore, NTS inhibitors can suppress HCMV replication in addition to inhibiting the HSVs.

Compounds #41, 46, 49, 55, 56, and 59 and the FDA-approved, anti-HCMV drug ganciclovir were subsequently evaluated with plaque reduction and toxicity assays in HFFs. HFFs were infected with HCMV in the presence of serial dilutions of the compounds. After 10 days the cultures were stained with neutral red and plaques were counted. Compound cytotoxicity for uninfected cells was determined in the same manner except that neutral red uptake by viable cells was measured by optical density. Compounds #41, 46, 49, 55, and 59 inhibited HCMV replication with $EC_{50}$ values of 0.33 to 1.94 µM (Table 6). In contrast to the 24 h HSV assays in HFFs, the NTS inhibitors had measurable toxicity in this 10 day assay, most notably #41 with a $CC_{50}$ of 2.9 µM. The TI values for the five NTS inhibitors of HCMV ranged from 5 for compound #46 to 17 for #55 and 59. Therefore, NTS inhibitors can suppress HCMV replication in addition to inhibiting the HSVs.

TABLE 5

Efficacy of select HSV inhibitors against HCMV using the CPE inhibition assay.

| Compound Number | $EC_{50}$ (µM) | $CC_{50}$ (µM) | TI |
|---|---|---|---|
| 41 | 2.1 | 8.9 | 4.2 |
| 46 | 1.4 | >60 | >43 |
| 49 | 1.7 | >60 | >35.3 |
| 55 | >60 | >60 | na[A] |
| 56 | 38.4 | 38.4 | 17.4 |
| 59 | 37.2 | 37.2 | 16.2 |
| Ganciclovir | 0.33 | >300 | >909 |

[A]na, not applicable

TABLE 6

Efficacy of select HSV inhibitors against HCMV using the plaque reduction assay.

| Compound Number | $EC_{50}$ (µM) | $CC_{50}$ (µM) | TI |
|---|---|---|---|
| 41 | 0.33 | 2.90 | 9 |
| 46 | 1.30 | 6.70 | 5 |
| 49 | 0.45 | 6.70 | 15 |
| 55 | 0.47 | 8.00 | 17 |
| 56 | 2.66 | 6.70 | 2 |
| 59 | 1.94 | 33.3 | 17 |
| Ganciclovir | 3.20 | >100 | >31 |

5. Efficacy in Mice

A. Ciclopirox (#41) and ciclopirox ethanolamine (#41-E).

Figure 14:
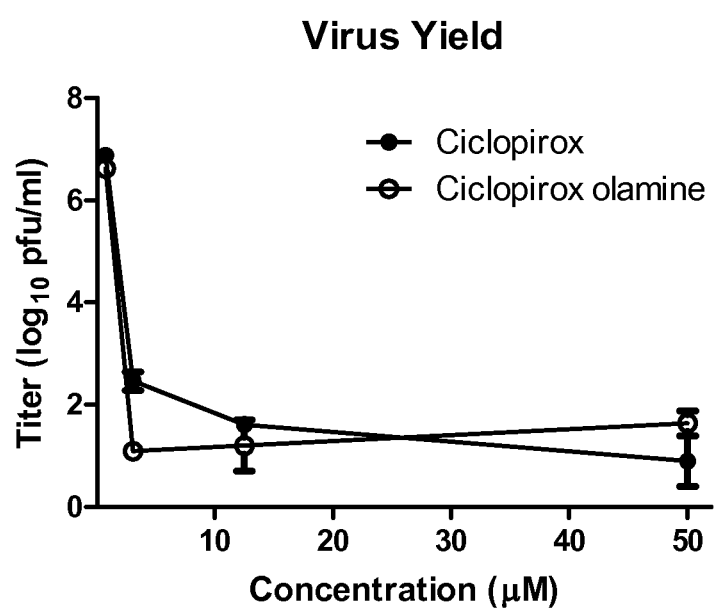
FIG. 14. Ciclopirox and its salt, ciclopirox olamine, suppress HSV-2 replication equivalently. HFF monolayers were infected with HSV-2 in the presence of various concentrations of ciclopirox or ciclopirox olamine. After 24 hours monolayers were collected and virus titer determined by plaque assay.

Ciclopirox ethanolamine (ciclopirox olamine; compound #41-E) is a pharmaceutically-acceptable salt form of ciclopirox (compound #41). Ciclopirox olamine is anti-angiogenic and anti-proliferative in cell cultures (Hoffman et al., 1991; Clement et al., 2002). Ciclopirox olamine therefore is preferentially cytotoxic to malignant cells, by a mechanism that involves chelation of intracellular iron (Eberhard et al., 2009). In HFFs, ciclopirox and its salt, ciclopirox olamine, are observed to suppress HSV-2 replication to an equivalent extent (FIG. 14).

Ciclopirox olamine is approved for topical use in humans as an antifungal (Sehgal, 1976). It has also been applied topically to mouse ear flaps at 1% (w/vol) in cream, which was shown to induce HIF-1 and VEGF expression and angiogenesis at wound margins but not on healthy skin (Linden et al., 2003) and applied in 10 µL volume of a 50 mM solution once per day to a wound on the dorsa of mice, which promotes healing (Ko et al., 2011). It is anti-inflammatory in other models (Hanel et al., 1991; Rosen et al., 1997).

Hanauske-Abel and colleagues treated female mice intravaginally for 4 consecutive days after medroxyprogesterone synchronization with 20 µL 1% Batrafen Vaginal Creme™ containing 28.8 mM total and 0.6 mM bioavailable ciclopirox (Hanauske-Abel et al., 2013). They observed no disruption of the mucinous cell layer or underlying squamous epithelium, and no increase in apoptosis in the epithelium or subepithelium compared with control mice. These researchers subsequently treated mice with Batrafen cream as above and subsequently infected the mice i.vag. with 10 $ID_{50}$ of HSV-2. The pre-treatment with this cream reportedly did not alter susceptibility to vaginal infection with HSV-2; the infection rate was 80% in both groups based on fluorescence-based assay of infectious virus in vaginal wash fluid 3 days post-infection. However, three elements make this data incomplete: First, the assay used to detect virus was non-quantitative. Second, only a single time point post-infection was assessed. Third, topical treatment of the mouse vaginal mucosa may not be the most beneficial route to achieve reduction of HSV titers.

Ciclopirox olamine has also been administered intragastrically (i.g.) to mice. Eberhard and colleagues (Eberhard et al., 2009) gave 25 mg/kg (~500 µg/mouse) daily in PBS and noted no gross organ damage or weight loss. The same dosing of ciclopirox olamine was also used by Zhou et al. (Zhou et al., 2010) without mention of deleterious effects. Lastly, ciclopirox olamine (800 µg/mouse) has been administered perorally daily for up to 60 days with no side effects observed (Kim et al., 2011). In each of these systemic applications, ciclopirox olamine improved outcomes in various tumor models.

B. Beta-Thujaplicinol (#46)

Beta-thujaplicinol inhibits hepatitis B virus replication by blocking the viral RNase H activity (Hu et al., 2013), and inhibits HIV reverse transcriptase by blocking the viral RNase H activity through chelation of divalent cations in the active site (Budihas et al., 2005; Chung et al., 2011). Inhibition of the divalent cation-dependent strand transfer reaction catalyzed by the viral integrase has also been demonstrated for beta-thujaplicinol (Semenova et al., 2006). However, only weak inhibition of HIV-1 replication was observed in cell-based assays.

C. Results

Figure 10:
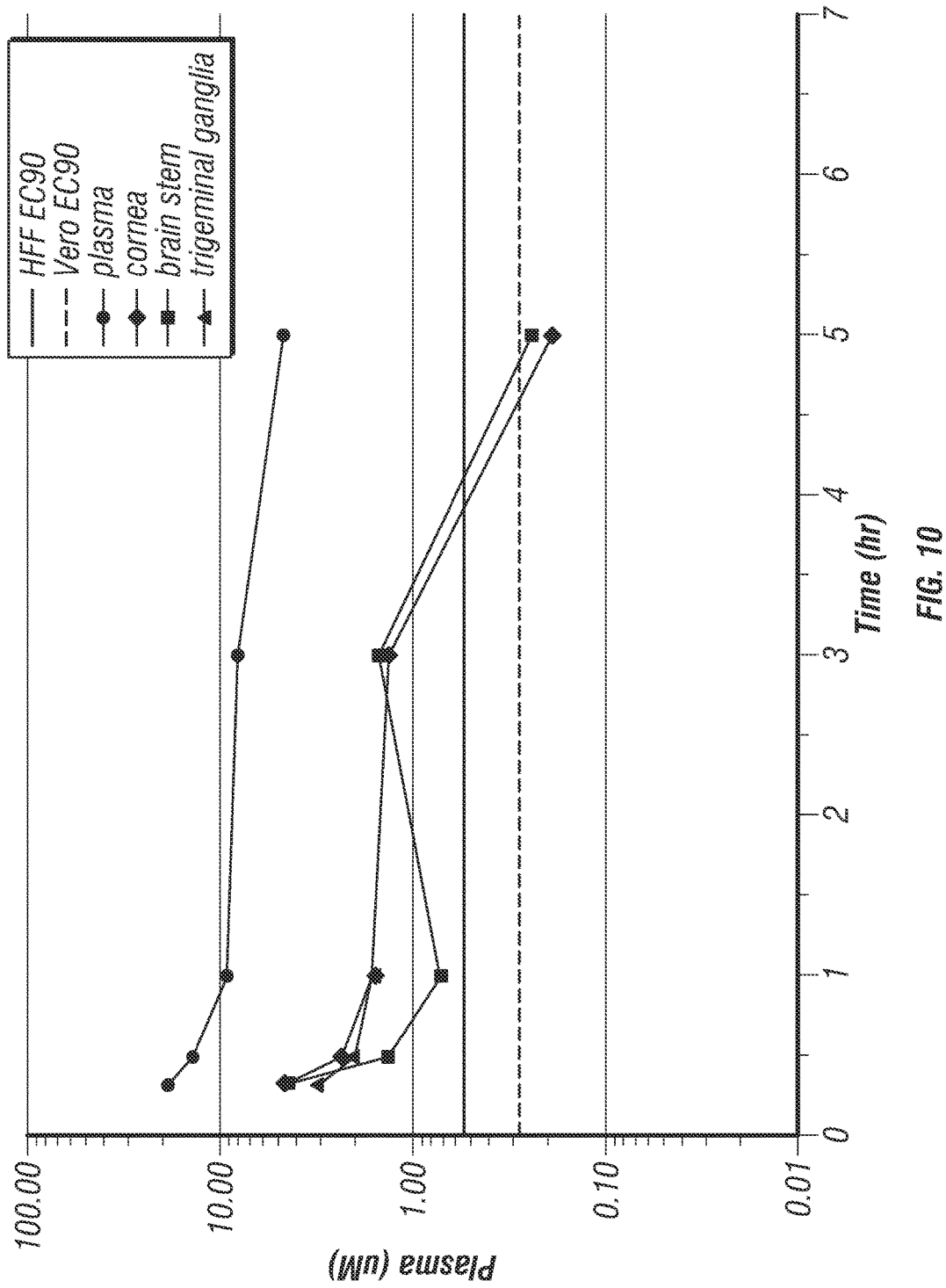
FIG. 10. Ciclopirox olamine tissue concentrations (µM) after oral gavage. BALB/c mice were treated with 100 mg/kg ciclopirox olamine by oral gavage. Pairs were euthanized at 15 min, 30 min, 1 hr, 3 hr and 5 hr post-treatment. Ciclopirox olamine concentrations in plasma, corneas, trigeminal ganglia and brainstems were determined by mass spectroscopy, with standardization to ciclopirox olamine spiked into a matrix of relevant tissue homogenate from untreated mice.

Ciclopirox olamine tissue concentrations (μM) after oral gavage. Ciclopirox olamine has previously been used to treat mice by oral gavage (25 to 40 mg/kg) for up to 60 days, but, assessment of penetration into the cornea and nervous system after oral gavage needed to be evaluated as well as tissue concentration over time to estimate appropriate dosing. In a single dose pharmacokinetic study, mice were treated with 100 mg/kg ciclopirox olamine by oral gavage. Pairs of mice were euthanized at various times post-treatment. Ciclopirox olamine concentrations in plasma, corneas, trigeminal ganglia and brainstems were determined by mass spectroscopy (FIG. 10). The plasma concentration at time of uptake was ~30 μM with decay of free plasma concentration over 5 hours to a level still 10-fold above the estimated $EC_{90}$ against HSV-1 (based on data in Vero cells and HFFs). Ciclopirox olamine concentrations in cornea and nervous system tissues were only ~5-fold lower than that in the plasma and remained above the estimated $EC_{90}$ until 5 hours post-treatment. These preliminary results indicate that ciclopirox olamine can be sustained in the cornea and nervous system for at least 4 h above the estimated $EC_{90}$ against HSV-1 after parenteral administration, and suggested dosing three times per day would help sustain tissue concentrations.

Compounds #41 and 46 reduce HSV-1 replication after topical application to the cornea. ACV has been used successfully to curtail HSV-1 shedding and nervous system invasion when given dropwise to the corneal epithelium (Higaki et al., 2006; Aoki et al., 1995). Three preliminary experiments were performed to determine if an NTS inhibitor could likewise reduce virus replication in the periphery or nervous system of mice infected via the corneal route with HSV-1.

Figure 11:
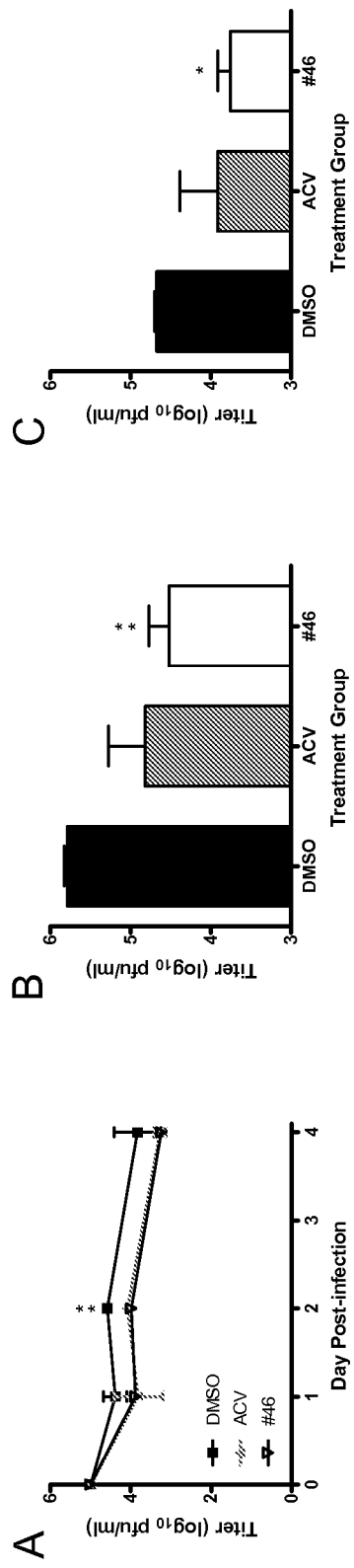
FIGS. 11A-C. Topical application of compound #46 reduces HSV-1 replication in vivo. Mice infected on the corneal surface with $1\times10^5$ pfu of HSV-1 per eye were treated once daily with the indicated compound (1 µg/eye) and virus titer in (FIG. 11A) the tear film over time post-infection.

In the first experiment, mice were infected on the cornea with HSV-1 and treated daily for 5 days with compound #46 (β-thujaplicinol) at 1 μg concentration in 10% DMSO. Control groups were treated with equivalent amounts of ACV or DMSO. Compared with DMSO control, compound #46 and ACV both transiently reduced the amount of virus shed in the tear film (FIG. 11A), and significantly reduced the amount of virus in the TG (FIG. 11B) and brainstem (FIG. 11C) at 5 days post-infection.

Figure 12:
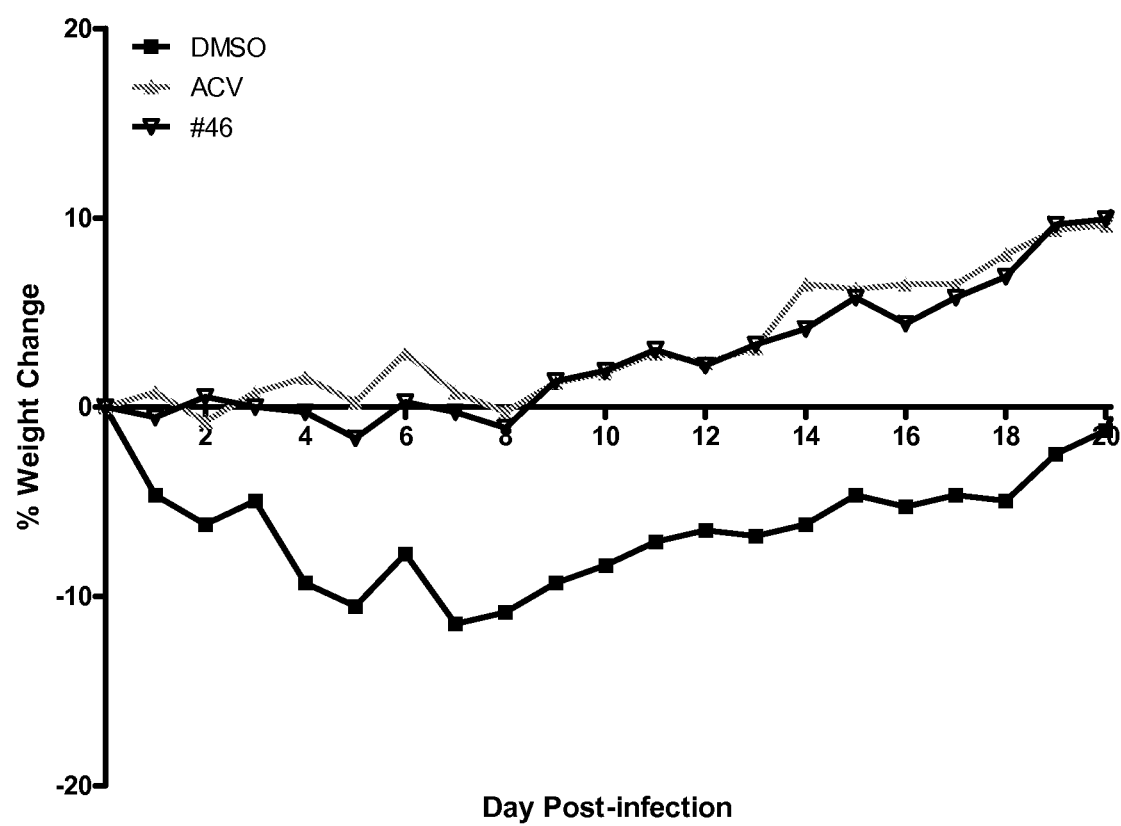
FIG. 12. Topical application of compound #46 prevents weight loss in mice infected with HSV-1. Mice infected on the corneal surface with $8\times10^4$ pfu of HSV-1 per eye were treated thrice daily with the indicated compound (1 µg/eye). Body weight of individual mice was determined daily post-infection. Data are expressed as mean percent change from starting weight. N=two mice per group. P<0.001 for DMSO v. #46.

In a second experiment, mice were infected on the cornea with HSV-1 and treated three times daily for 5 days with compound #46 (β-thujaplicinol) at 1 μg concentration in 10% DMSO. Control groups were treated with equivalent amounts of ACV or DMSO. Body weight was monitored daily post-infection as a sensitive indicator of overall health (FIG. 12). Mice treated with ACV or compound #46 maintained their weight through 8 days post-infection and then gained weight thereafter. In marked contrast, mice treated with DMSO lost more than 10% of their body weight before beginning to recover, but did not return to their starting weight until 3 week post-infection. Together, these preliminary data suggest that topical treatment of mice with compound #46 permits mice to resist HSV-1 infection of the nervous system and maintain their overall health to a similar extent as ACV, and to a much greater extent than mice treated with diluent alone.

Figure 13:
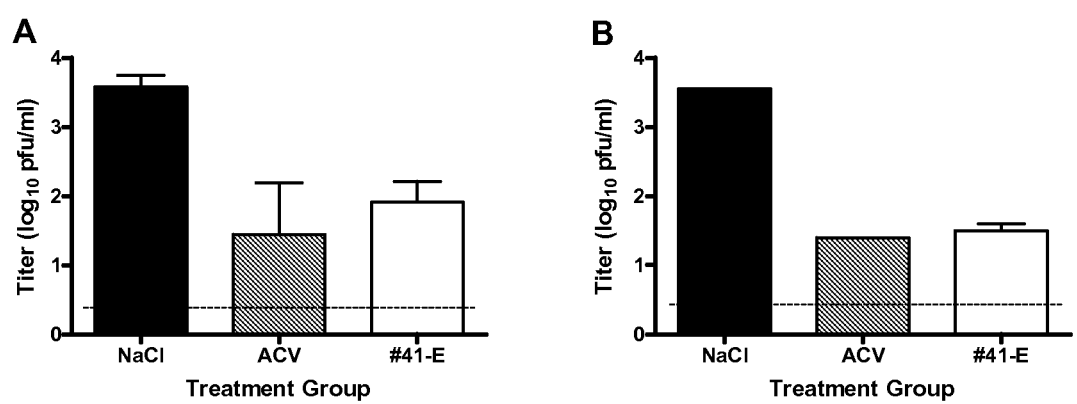
FIGS. 13A-B. Topical treatment with compound #41-E reduces HSV-1 infection of the nervous system. BALB/c mice infected on the corneal surface with $2\times10^4$ pfu of HSV-1 were topically treated thrice daily with ACV (two mice) or ciclopirox olamine (#41-E; two mice). Each appeared to reduce viral titer compared with saline control (one mouse). Dashed line shows limit of detection in the assay. P=0.0075 for DMSO v. #41-E TG.

In a third experiment, mice were infected with HSV-1 and treated with 7.5 μg/eye of ciclopirox olamine (#41-E) or ACV in saline dropwise three times per day for 5 days. Infected mice treated with saline served as a negative control. Titers of virus in the TG (FIG. 13A) and brainstem (FIG. 13B) on day 5 post-infection were lower in mice treated with compound #41 compared to the saline control, and were reduced to a similar extent as ACV.

Together, these preliminary experiments in mice demonstrate that compound #46 (beta-thujaplicinol) and compound #41-E (ciclopirox olamine) are effective in reducing HSV-1 replication in the cornea, trigeminal ganglia and brainstem after ocular infection compared with diluent alone, and to a similar extent as acyclovir. Ciclopirox olamine also significantly improved the overall health of the mice as shown by maintenance of body weight.

* * *

All of the compositions and methods disclosed and claimed herein can be made and executed without undue experimentation in light of the present disclosure. While the compositions and methods of this invention have been described in terms of preferred embodiments, it will be apparent to those of skill in the art that variations may be applied to the compositions and methods, and in the steps or in the sequence of steps of the methods described herein without departing from the concept, spirit and scope of the invention. More specifically, it will be apparent that certain agents which are both chemically and physiologically related may be substituted for the agents described herein while the same or similar results would be achieved. All such similar substitutes and modifications apparent to those skilled in the art are deemed to be within the spirit, scope and concept of the invention as defined by the appended claims.

F. References

The following references, to the extent that they provide exemplary procedural or other details supplementary to those set forth herein, are specifically incorporated herein by reference:

Alba et al., *Genome Res.*, 11:43-54, 2001.
Andrei and Snoeck, *Curr Opin Infect Dis.* 26:551-560, 2013.
Aoki et al., *Antimicrob Agents Chemother.* 39:846-849, 1995.
Ariyoshi et al., *Cell* 78:1063-1072, 1994.
Arvin & Gilden, *Varicella-Zoster Virus*, 2015-2057, 2013.
Balzarini et al., *PLoS Pathog.* 9:e1003456, 2013.
Bernstein et al., *Antiviral Res* 92:386-388, 2011.
Billamboz et al., *J. Med. Chem.* 54:1812-1824, 2011.
Bogner et al., *J Virol.*, 72:2259-2264, 1998.
Bogner, *Rev Med Virol.*, 12:115-127, 2002.
Bokesch et al., *J. Nat. Prod.* 71, 1634-1636, 2008.
Bortner et al., *J Mol Biol.* 231:241-250, 1993.
Budihas et al., *Nucleic Acids Res.* 33, 1249-1256, 2005.
Chen et al., *J. Neurovirology* 8:204-210, 2002.
Choi et al., *Antiviral Res.* 55: 279-290, 2002.
Chung et al., *J. Med. Chem.* 54, 4462-4473, 2011.
Chung et al., *Antimicrob. Agents Chemother.* 54, 3913-3921, 2010.
Clement et al., *Int J Cancer* 100:491-498, 2002.
Coen, *Antiviral Res*, 15:287-300, 1991.
Coen, *Viral DNA polymerases*, p. 495-523, 1996.
Cohen, *The New England journal of medicine* 369:255-263, 2013.
Damania & Cesarman, *Kaposi's Sarcoma-Associated Herpesvirus*, 2080-2128, 2013.
Decaro et al., *The Veterinary clinics of North America. Small animal practice* 38:799-814, viii, 2008.
Derse et al., *J Biol Chem*, 257:10251-10260, 1982.
Di et al., *Bioorg. Med. Chem. Lett.* 20, 398-402, 2010.
Didierjean et al., *Antimicrob. Agents Chemother.* 49, 4884-4894, 2005.

Drew et al., *Clin Diagn Virol.* 1:179-185, 1993.
Drew et al., *J Infect Dis.* 179:1352-1355, 1999.
Drew et al., *Am J Transplant* 1:307-312, 2001.
Dolan et al., *J Virol* 72:2010-2021, 1998.
Duan et al., *J Infect Dis,* 200:1402-1414, 2009.
Duan, et al., *J Infect Dis,* 198:659-663, 2008.
Dyda et al., *Science* 266:1981-1986, 1994.
Eberhard et al., *Blood* 114:3064-3073, 2009.
Elion et al., *Proc Natl Acad Sci USA,* 74:5716-5720, 1977
Fenner et al., *Veterinary Virology,* 2 ed. Academic Press, 1993.
Field and Biron, *Clin Microbiol Rev,* 7:1-13, 1994.
Field and Vere Hodge, *Br Med Bull.* 106:213-249, 2013.
Fortier et al., *Veterinary J.*186:148-156, 2010.
Frank et al., *Biol. Chem.* 379:1407-1412, 1998.
Frank et al., *Proc. Natl. Acad. Sci. USA* 95:12872-12877, 1998.
Freed et al., "HIVs and their replication," in: Knipe, D. M., Howley, P. M., Griffin, D. E., Lamb, R. A., Martin, M. A., Roizman, B., Straus, S. E. (Eds.), FIELDS VIROLOGY. Lippincott Williams & Wilkins, Philadelphia, pp. 2107-2185, 2007.
Fuji et al., *J. Med. Chem.* 52, 1380-1387, 2009.
Gao et al., *Virology* 249:460-470, 1998.
Gaskell et al., *Feline herpesvirus. Veterinary research* 38:337-354, 2007.
Gerelsaikhan et al., *J. Virol.* 70, 4269-4274, 1996.
Gilbert et al., *Canadian journal of public health=Revue canadienne de sante publique,* 2011.
Gilbert, et al., *Drug Resist Updat,* 5:88-114, 2002.
Gimeno, *Vaccine* 26 Suppl 3:C31-41, 2008.
Goedken et al., *J. Biol. Chem.* 276, 7266-7271, 2001.
Hanauske-Abel et al., *PloS One* 8:e74414. doi: 10.1371, 2013.
Hanel et al., *Mycoses* 34 Suppl 1:91-93, 1991.
Hanson et al., *Viruses* 3(11): 2160-2191, 2011.
Higaki et al., *Cornea* 25(10 Suppl 1):564-67, 2006.
Himmel et al., *ACS Chem. Biol.* 1:702-712, 2006.
Himmel et al., *Structure* 17: 1625-1635, 2009.
Hirari, *Current Topics in Microbiology and Immunology: Marek's Disease,* 2001.
Hoffman et al., *Cytometry* 12:26-32, 1991.
Horowitz et al., *Journal of American college health: J of ACH* 59:69-74, 2011.
Hostomsky et al., *Nulceases,* vol. 2, 1993b.
Hostomsky et al., "Ribonuclease H," in: Linn, S. M., Lloyd, R. S., Roberts, R. J. (Eds.), Nulceases. Cold Spring Harbor Laboratory Press, Plainview, N.Y., pp. 341-376, 1993a.
Hostomsky et al., *Structure* 3:131-134, 1993c.
Hu et al., *Antiviral Res* 99:221-229, 2013.
Hwang and Bogner, *J Biol Chem.,* 277:6943-6948, 2002.
Imai et al., *J Infect Dis.* 189:611-615, 2004.
James et al., *Antiviral Res* 83:207-213, 2009.
Johnston et al., *Lancet* 379:641-647, 2012.
Kamali et al., *Sexually transmitted infections* 75:98-102, 1999.
Katayanagi et al., *Nature* 347: 306-309, 1990.
Keck et al., *J. Biol. Chem.* 273, 34128-34133, 1998.
Kim et al., In *Vivo* 25:887-893, 2011.
Kimberlin, *Seminars in perinatology* 31:19-25, 2007.
Kirschberg et al., *J. Med. Chem.* 52:5781-5784, 2009.
Klarmann et al., *AIDS Rev* 4: 183-194, 2002.
Klumpp et al., *Nucleic Acids Res.* 31, 6852-6859, 2004.
Klumpp and Mirzadegan, *Curr. Pharm. Des* 12:1909-1922, 2006.
Knipe and Spang *J Virol,* 43:314-324, 1982.
Ko et al., *PLoS One* 6:e27844. doi: 10.1371, 2011.
Komatsu et al., *Antiviral Res* 101:12-25, 2014.
Korom et al., *J Virol,* 87:5882-5894, 2013.
Kwun et al., *J. Gen. Virol.* 82, 2235-2241, 2001.
Lai et al., *Structure* 8:897-904, 2000.
Levin et al., *Clin Infect Dis,* 39 Suppl 5:S248-257, 2004.
Li et al., *Mol. Biol. Eva* 12:657-670, 1999.
Lima et al., *Methods Enzymol.* 341:430-440, 2001.
Linden et al., *Faseb J.,* 17:761-763, 2003.
Liu et al., *J. Biol. Chem.* 281:18193-18200, 2006.
Longnecker et al., *Epstein-Barr Virus,* 1898-1959, 2013.
Luzuriaga & Sullivan, *N Eng J Med.* 362:1993-2000, 2010.
Manicklal et al., *Clinical Microbiology Rev.* 26:86-102, 2013.
Marcellin et al., *N Engl. J. Med.* 359: 2442-2455, 2008.
Marchand, Tchesnokov, and Gotte. *J Biol Chem* 282: 3337-3346, 2007.
Marfori et al., *J Clin* Virol. 38:120-5, 2007.
McDermott et al., *J Virol,* 51:747-753, 1984.
Mettenleiter et al., *Virus Res.* 143:222-234, 2009.
Mohni et al., *J. Virol.* 85:12241-12253, 2011.
Morfin and Thouvenot, *J Clin Virol.,* 26:29-37, 2003.
Morrison and Knipe, *Virology,* 220:402-413, 1996.
Nakagawa and Tayama, *Chem Biol Interact,* 116:45-60, 1998.
Nandi et al., *Animal health research reviews/Conference of Research Workers in Animal,* 2009.
Nauwynck et al., *Veterinary Res.* 38:229-241, 2007.
Nimonkar and Boehmer, *J Biol Chem.* 278:9678-9682, 2003.
Nowotny et al., *Cell* 121: 1005-1016, 2005.
Nowotny, *EMBO Rep.* 10:144-151, 2009.
Obasi et al., *J. Infectious Dis.* 179:16-24, 1999.
Parker et al., *EMBO J.*23: 4727-4737, 2004.
Pellet & Roizman, *Herpesviridae* 1802-1822, 2013.
Pelosi et al., *Adv Exp Med Biol,* 312:151-158, 1992.
Pena et al., *J. Clin.* Microbiol. 48:150-153, 2010.
Popovic et al., *J. Thrombosis Thrombolysis* 33:160-172, 2012.
Potenza et al., *Protein Expr. Purif.* 55: 93-99, 2007.
Quenelle et al., *Antivir Chem* Chemother 22:131-137, 2011.
Quinlan et al., *Cell* 36:857-868, 1984.
Reyes et al., *Arch Intern Med,* 163:76-80, 2003.
Roizman et al., *Herpes Simplex Viruses,* 1823-1897, 2013.
Rosen et al., *Int J Dermatol.,* 36:788-792, 1997.
Scheffczik et al., *Nucleic Acids Res.,* 30:1695-1703, 2002.
Schmit and Boivin, *J Infect Dis,* 180:487-490, 1999.
Scholz et al., *Nucleic Acids Res.,* 31:1426-1433, 2003.
Schumacher et al., *PLoS Pathog.* 8:e1002862, 2012.
Sehgal, *Br J Dermatol.* 95:83-88, 1976.
Selvarajan et al., *J. Virol.* 87:7140-7148, 2013.
Semenova et al., *Mol. Pharmacol.* 69:1454-1460, 2006.
Shaw-Reid et al., *J Biol. Chem.* 278, 2777-2780, 2003.
Smith & Roberts, *J. ACH* 57:389-394, 2009.
Smith et al., *J. Virol.* 68, 5721-5729, 1994.
Smith, *Veterinary J.* 153:253-268, 1997.
Snydman, *Clin Infect Dis.* 47:883-884, 2008.
Song et al., *Science* 305: 1434-1437, 2004.
Su et al., *J. Virol.* 84:7625-7633, 2010.
Takada et al., *J. Nat. Prod.* 70, 1647-1649, 2007.
Tavis et al., *PLoS Pathogens* 9:e1003125, 2013.
Wald et al., *N Engl J Med.* 370:201-210, 2014.
Wang et al., *J. Virol.* 79:14079-14087, 2005.
Wang et al., *J Clin Virol,* 52:107-112, 2011.
Weizman & Weller, *Interactions between HSV-1 and the DNA damage response,* p. 257-268, 2011.

Weller & Coen, *Cold Spring Harbor Perspectives in Biology* 4:a013011, 2012.
Weller and Kuchta, *Expert Opin Ther Targets*, 17:1119-1132, 2013.
Wendeler et al., *ACS Chem. Biol.* 3, 635-644, 2008.
Williams et al., *Bioorg. Med. Chem. Lett.* 20:6754-6757, 2010.
Xu et al., *JAMA* 296:964-973, 2006.
Yamanishi et al., *Human Herpesviruses* 6 and 7, p. 2058-2079, 2013.
Yan et al., *MBio* 5:e01318-14, 2014.
Yang et al., *Science* 249: 1398-1405, 1990.
Yang and Steitz, *Structure*, 3, 131-134, 1995.
Yao et al., *Antimicrob Agents Chemother.* 58:2807-2815, 2014.
Zhou et al., *Int J Cancer* 127:2467-2477, 2010.
Zhou et al, *J. Viral.* 88:11121-11129, 2014.
Zhu et al., *J. Virol.* 84:7459-7472, 2010.

five groups, or when taken together with $R_2$ is alkanediyl$_{(C \leq 12)}$, alkenediyl$_{(C \leq 12)}$, or a substituted version of either of these groups;

$R_2$ and $R_3$ when taken together have a formula:

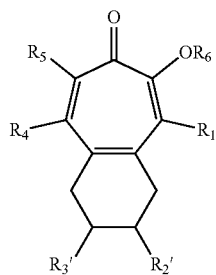

(Ib)

What is claimed:

1. A method of inhibiting herpesvirus replication comprising contacting a herpesvirus nucleic acid metabolism enzyme with a compound having the formula:

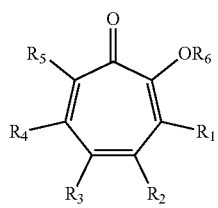

(I)

wherein:
$R_1$ is hydrogen, hydroxyl, alkyl$_{(C \leq 6)}$, or substituted alkyl$_{(C \leq 6)}$;
$R_2$ is hydrogen, alkyl$_{(C \leq 6)}$, substituted alkyl$_{(C \leq 6)}$, or when taken together with $R_3$ is alkanediyl$_{(C \leq 12)}$, alkenediyl$_{(C \leq 12)}$, or a substituted version of either of these groups;
$R_3$ is hydrogen, alkyl$_{(C \leq 8)}$, alkenyl$_{(C \leq 8)}$, alkynyl$_{(C \leq 8)}$, acyloxy$_{(C \leq 12)}$, or a substituted version of any of the last wherein:
$R_2'$ and $R_3'$ are each independently hydrogen, alkyl$_{(C \leq 4)}$, substituted alkyl$_{(C \leq 4)}$, alkenyl$_{(C \leq 4)}$, or substituted alkenyl$_{(C \leq 4)}$;
$R_4$ is hydrogen, alkyl$_{(C \leq 8)}$, alkenyl$_{(C \leq 8)}$, alkynyl$_{(C \leq 8)}$, aryl$_{(C \leq 8)}$, aralkyl$_{(C \leq 12)}$, or a substituted version of any of the last five groups;
$R_5$ is hydrogen, alkyl$_{(C \leq 6)}$, or a substituted alkyl$_{(C \leq 6)}$; and
$R_6$ is hydrogen, acyl$_{(C \leq 12)}$, or substituted acyl$_{(C \leq 12)}$,
or a pharmaceutically acceptable salt thereof.

2. The method of claim 1, wherein the compound is further defined by the formula:

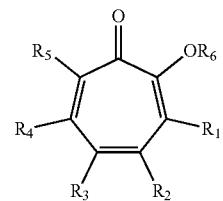

(I)

wherein:
R$_1$ is hydrogen, hydroxyl, or alkyl$_{(C \leq 6)}$;
R$_2$ is hydrogen, alkyl$_{(C \leq 6)}$, or when taken together with R$_3$ is as defined below in Formula Ib;
R$_3$ is hydrogen, alkyl$_{(C \leq 8)}$, alkenyl$_{(C \leq 8)}$, or when taken together with R$_2$ is as defined below in Formula Ib;
R$_2$ and R$_3$ when taken together have a formula:

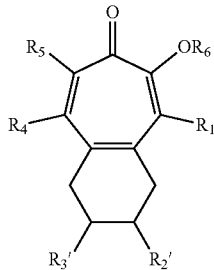 (Ib)

wherein:
R$_2$' and R$_3$' are each independently hydrogen or alkenyl$_{(C \leq 4)}$;
R$_4$ is hydrogen, alkyl$_{(C \leq 8)}$, aralkyl$_{(C \leq 12)}$, or substituted aralkyl$_{(C \leq 12)}$;
R$_5$ is hydrogen or alkyl$_{(C \leq 6)}$; and
R$_6$ is hydrogen or substituted acyl$_{(C \leq 12)}$,
or a pharmaceutically acceptable salt thereof.

3. The method of claim 1, wherein R$_1$ is hydrogen or hydroxyl.

4. The method of claim 1, wherein R$_2$ and R$_3$ are taken together and have formula Ib.

5. The method of claim 1, wherein R$_3$' is alkenyl$_{(C \leq 4)}$.

6. The method of claim 1, wherein R$_4$ is hydrogen, alkyl$_{(C \leq 4)}$, or substituted aralkyl$_{(C \leq 12)}$.

7. The method of claim 1, wherein R$_6$ is hydrogen.

8. The method of claim 1, wherein the pharmaceutically acceptable salt is an ethanolamine salt.

9. The method of claim 1, further comprising contacting said enzyme with a second inhibitor of said enzyme.

10. The method of claim 9, wherein said enzyme is located in a cell.

11. The method of claim 10, wherein said cell is located in vitro.

12. The method of claim 10, wherein said cell is located in a living subject.

13. The method of claim 12, wherein said subject is a vertebrate infected with a herpesvirus.

14. The method of claim 13, wherein said compound is administered intravenously, intra-arterially, orally, buccally, nasally, rectally, vaginally, topically, intramuscularly, intradermally, cutaneously or subcutaneously.

15. The method of claim 13, wherein said subject is further administered a second anti-herpesvirus therapy.

* * * * *

SEQUENCE LISTING

<160> NUMBER OF SEQ ID NOS: 2

<210> SEQ ID NO 1
<211> LENGTH: 20
<212> TYPE: DNA
<213> ORGANISM: Artificial Sequence
<220> FEATURE:
<223> OTHER INFORMATION: Synthetic Primer

<400> SEQUENCE: 1
gagctaacac tcggcttgct                                            20

<210> SEQ ID NO 2
<211> LENGTH: 18
<212> TYPE: DNA
<213> ORGANISM: Artificial Sequence
<220> FEATURE:
<223> OTHER INFORMATION: Synthetic Primer

<400> SEQUENCE: 2
tctcctcccc gtctttcc                                              18